United States Patent
Debelak et al.

(10) Patent No.: US 9,382,545 B2
(45) Date of Patent: Jul. 5, 2016

(54) CPG OLIGONUCLEOTIDE ANALOGS CONTAINING HYDROPHOBIC T ANALOGS WITH ENHANCED IMMUNOSTIMULATORY ACTIVITY

(71) Applicant: COLEY PHARMACEUTICAL GMBH, Dusseldorf (DE)

(72) Inventors: Harald Debelak, Hilden (DE); Eugen Uhlmann, Glashuetten (DE); Marion Jurk, Dormagen (DE)

(73) Assignee: COLEY PHARMACEUTICAL GMBH, Dusseldorf (DE)

(*) Notice: Subject to any disclaimer, the term of this patent is extended or adjusted under 35 U.S.C. 154(b) by 71 days.

(21) Appl. No.: 14/046,044

(22) Filed: Oct. 4, 2013

(65) Prior Publication Data

US 2014/0163213 A1    Jun. 12, 2014

Related U.S. Application Data

(63) Continuation of application No. 12/442,295, filed as application No. PCT/IB2007/004389 on Sep. 25, 2007, now Pat. No. 8,580,268.

(60) Provisional application No. 60/847,811, filed on Sep. 27, 2006.

(51) Int. Cl.
  C12N 15/117    (2010.01)
  C07H 21/00    (2006.01)

(52) U.S. Cl.
  CPC ............. *C12N 15/117* (2013.01); *C07H 21/00* (2013.01); *C12N 2310/17* (2013.01); *C12N 2310/33* (2013.01); *C12N 2310/332* (2013.01); *C12N 2310/335* (2013.01)

(58) Field of Classification Search
  CPC ........... C12N 15/117; C12N 2310/335; C12N 2310/33; C12N 2310/332; C12N 2310/17; C07H 21/00
  USPC ............................................... 536/23.1, 25.6
  See application file for complete search history.

(56) References Cited

U.S. PATENT DOCUMENTS

| | | |
|---|---|---|
| 5,416,203 A | 5/1995 | Letsinger |
| 5,527,899 A | 6/1996 | Froehler |
| 5,646,126 A | 7/1997 | Cheng et al. |
| 5,663,153 A | 9/1997 | Hutcherson et al. |
| 5,696,248 A | 12/1997 | Peyman et al. |
| 5,723,335 A | 3/1998 | Hutcherson et al. |
| 5,929,226 A | 7/1999 | Padmapriya et al. |
| 5,968,909 A | 10/1999 | Agrawal et al. |
| 6,030,955 A | 2/2000 | Stein et al. |
| 6,031,086 A | 2/2000 | Switzer |
| 6,121,434 A | 9/2000 | Peyman et al. |
| 6,194,388 B1 | 2/2001 | Krieg et al. |
| 6,207,646 B1 | 3/2001 | Krieg et al. |
| 6,207,819 B1 | 3/2001 | Manoharan et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,348,312 B1 | 2/2002 | Peyman et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,476,000 B1 | 11/2002 | Agrawal et al. |
| 6,479,504 B1 | 11/2002 | Macfarlane et al. |
| 6,521,637 B2 | 2/2003 | Macfarlane |
| 6,558,670 B1 | 5/2003 | Friede et al. |
| 6,562,798 B1 | 5/2003 | Schwartz |
| 6,589,940 B1 | 7/2003 | Raz et al. |
| 6,605,708 B1 | 8/2003 | Habus et al. |
| 6,610,308 B1 | 8/2003 | Haensler |
| 6,610,661 B1 | 8/2003 | Carson et al. |
| 6,653,292 B1 | 11/2003 | Krieg et al. |
| 6,727,230 B1 | 4/2004 | Hutcherson et al. |
| 6,815,429 B2 | 11/2004 | Agrawal |
| 6,821,957 B2 | 11/2004 | Krieg et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,038,029 B2 | 5/2006 | Lopez |
| 7,105,495 B2 | 9/2006 | Agrawal et al. |
| 7,176,296 B2 | 2/2007 | Agrawal et al. |
| 7,223,741 B2 | 5/2007 | Krieg |
| 7,255,868 B2 | 8/2007 | Fearon et al. |
| 7,262,286 B2 | 8/2007 | Kandimalla et al. |
| 7,271,156 B2 | 9/2007 | Krieg et al. |
| 7,276,489 B2 | 10/2007 | Agrawal et al. |
| 7,354,711 B2 | 4/2008 | Macfarlane |
| 7,402,572 B2 | 7/2008 | Krieg et al. |
| 7,405,285 B2 | 7/2008 | Agrawal et al. |
| 7,407,944 B2 | 8/2008 | Agrawal et al. |

(Continued)

FOREIGN PATENT DOCUMENTS

| | | |
|---|---|---|
| EP | 0302758 | 2/1989 |
| EP | 0468520 | 1/1992 |

(Continued)

OTHER PUBLICATIONS

Tam et al., Liposomal encapsulation enhances the activity of immunostimulatory oligonucleotides. Future Lipidology. Feb. 2006; 1(1): 35-46.

(Continued)

*Primary Examiner* — Clinton Brooks
*Assistant Examiner* — Yih-Horng Shiao
(74) *Attorney, Agent, or Firm* — Keith D. Hutchinson; Matthew J. Pugmire

(57) ABSTRACT

The invention relates to oligonucleotides including at least one lipophilic substituted nucleotide analog and a pyrimidine-purine dinucleotide. The invention also relates to pharmaceutical compositions and methods of use thereof.

8 Claims, 32 Drawing Sheets

(56) References Cited

U.S. PATENT DOCUMENTS

| | | |
|---|---|---|
| 7,410,975 B2 | 8/2008 | Lipford et al. |
| 7,488,490 B2 | 2/2009 | Davis et al. |
| 7,517,861 B2 | 4/2009 | Krieg et al. |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Krieg |
| 7,576,066 B2 | 8/2009 | Kreig |
| 7,585,847 B2 | 9/2009 | Bratzler et al. |
| 7,605,138 B2 | 10/2009 | Krieg |
| 7,615,539 B2 | 11/2009 | Krieg et al. |
| 7,674,777 B2 | 3/2010 | Krieg |
| 7,713,529 B2 | 5/2010 | Krieg et al. |
| 7,723,022 B2 | 5/2010 | Krieg et al. |
| 7,723,500 B2 | 5/2010 | Krieg et al. |
| 7,776,344 B2 | 8/2010 | Hartmann et al. |
| 7,795,235 B2 | 9/2010 | Krieg et al. |
| 7,807,803 B2 | 10/2010 | Krieg et al. |
| 7,820,379 B2 | 10/2010 | Bauer et al. |
| 7,879,810 B2 | 2/2011 | Krieg et al. |
| 7,888,327 B2 | 2/2011 | Krieg et al. |
| 7,935,675 B1 | 5/2011 | Krieg et al. |
| 7,956,043 B2 | 6/2011 | Krieg et al. |
| 7,998,492 B2 | 8/2011 | Ahluwalia et al. |
| 8,008,266 B2 | 8/2011 | Krieg et al. |
| 8,058,249 B2 | 11/2011 | Krieg et al. |
| 8,114,419 B2 | 2/2012 | Krieg |
| 8,114,848 B2 | 2/2012 | Krieg et al. |
| 8,129,351 B2 | 3/2012 | Krieg et al. |
| 8,148,340 B2 | 4/2012 | Krieg et al. |
| 8,153,141 B2 | 4/2012 | Lipford et al. |
| 8,158,592 B2 | 4/2012 | Krieg et al. |
| 8,580,268 B2 * | 11/2013 | Debelak et al. ............ 424/184.1 |
| 2001/0044416 A1 | 11/2001 | McCluskie et al. |
| 2002/0091097 A1 | 7/2002 | Bratzler et al. |
| 2002/0137714 A1 | 9/2002 | Kandamalla et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0059773 A1 * | 3/2003 | Van Nest et al. ................. 435/6 |
| 2003/0091599 A1 | 5/2003 | Davis et al. |
| 2003/0100527 A1 | 5/2003 | Krieg et al. |
| 2003/0119773 A1 | 6/2003 | Raz et al. |
| 2003/0129605 A1 | 7/2003 | Yu et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0224010 A1 | 12/2003 | Davis et al. |
| 2003/0232074 A1 | 12/2003 | Lipford et al. |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0047869 A1 | 3/2004 | Garcon et al. |
| 2004/0053880 A1 | 3/2004 | Krieg |
| 2004/0058883 A1 | 3/2004 | Phillips et al. |
| 2004/0087534 A1 | 5/2004 | Krieg et al. |
| 2004/0092468 A1 | 5/2004 | Schwartz et al. |
| 2004/0106568 A1 | 6/2004 | Krieg et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0171150 A1 | 9/2004 | Krieg et al. |
| 2004/0181045 A1 | 9/2004 | Krieg et al. |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0004144 A1 | 1/2005 | Carson et al. |
| 2005/0009773 A1 | 1/2005 | Kandimalla et al. |
| 2005/0009774 A1 | 1/2005 | Krieg et al. |
| 2005/0013812 A1 | 1/2005 | Dow et al. |
| 2005/0026861 A1 | 2/2005 | Kandimalla et al. |
| 2005/0032734 A1 | 2/2005 | Davis et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0148537 A1 | 7/2005 | Krieg et al. |
| 2005/0169888 A1 | 8/2005 | Hartmann et al. |
| 2005/0182017 A1 | 8/2005 | Krieg |
| 2005/0197314 A1 | 9/2005 | Krieg et al. |
| 2005/0209184 A1 | 9/2005 | Klinman et al. |
| 2005/0215501 A1 | 9/2005 | Lipford et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0266015 A1 | 12/2005 | Clerici et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0019916 A1 | 1/2006 | Krieg et al. |
| 2006/0019918 A1 | 1/2006 | Agrawal et al. |
| 2006/0019923 A1 | 1/2006 | Davis et al. |
| 2006/0058251 A1 | 3/2006 | Krieg et al. |
| 2006/0074040 A1 | 4/2006 | Kandimalla et al. |
| 2006/0089326 A1 | 4/2006 | Krieg et al. |
| 2006/0094683 A1 | 5/2006 | Krieg et al. |
| 2006/0140875 A1 * | 6/2006 | Krieg ................... A61K 9/0043 424/46 |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0189550 A1 | 8/2006 | Jiang et al. |
| 2006/0211639 A1 | 9/2006 | Bratzler et al. |
| 2006/0211644 A1 | 9/2006 | Krieg et al. |
| 2006/0217328 A1 | 9/2006 | Kandimalla et al. |
| 2006/0229271 A1 | 10/2006 | Krieg et al. |
| 2006/0241076 A1 | 10/2006 | Uhlmann et al. |
| 2006/0287262 A1 | 12/2006 | Agrawal et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |

(56) References Cited

U.S. PATENT DOCUMENTS

| | | |
|---|---|---|
| 2007/0065467 A1 | 3/2007 | Krieg et al. |
| 2007/0066554 A1 | 3/2007 | Krieg et al. |
| 2007/0078104 A1 | 4/2007 | Krieg et al. |
| 2007/0093439 A1 | 4/2007 | Agrawal et al. |
| 2007/0105800 A1 | 5/2007 | Agrawal et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0219153 A1 | 9/2007 | Kandimalla et al. |
| 2007/0224210 A1 | 9/2007 | Krieg et al. |
| 2007/0232622 A1 | 10/2007 | Lipford et al. |
| 2007/0280929 A1 | 12/2007 | Hoerr et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |
| 2009/0060927 A1 | 3/2009 | Wagner et al. |
| 2009/0117132 A1 | 5/2009 | Readett et al. |
| 2009/0142362 A1 | 6/2009 | Krieg et al. |
| 2009/0155212 A1 | 6/2009 | Bratzler et al. |
| 2009/0155307 A1 | 6/2009 | Davis et al. |
| 2009/0191188 A1 | 7/2009 | Krieg et al. |
| 2009/0202575 A1 | 8/2009 | Krieg et al. |
| 2009/0214578 A1 | 8/2009 | Bauer |
| 2009/0297540 A1 | 12/2009 | Mellor et al. |
| 2009/0306177 A1 | 12/2009 | Uhlmann et al. |
| 2009/0311277 A1 | 12/2009 | Krieg |
| 2010/0125101 A1 | 5/2010 | Krieg et al. |
| 2010/0144846 A1 | 6/2010 | Jurk et al. |
| 2010/0183639 A1 | 7/2010 | Uhlmann et al. |
| 2010/0285041 A1 | 11/2010 | Uhlmann et al. |
| 2011/0033421 A1 | 2/2011 | Hartmann et al. |
| 2011/0081366 A1 | 4/2011 | Krieg |
| 2011/0098456 A1 | 4/2011 | Uhlmann et al. |
| 2011/0135605 A1 | 6/2011 | Ahluwalia et al. |
| 2011/0201672 A1 | 8/2011 | Krieg et al. |
| 2011/0244025 A1 | 10/2011 | Uhlmann et al. |

FOREIGN PATENT DOCUMENTS

| | | |
|---|---|---|
| WO | WO9014822 | 12/1990 |
| WO | WO9202258 | 2/1992 |
| WO | WO9811211 | 3/1998 |
| WO | WO9849288 | 11/1998 |
| WO | WO9852962 | 11/1998 |
| WO | WO9956755 | 11/1999 |
| WO | WO0006588 | 2/2000 |
| WO | WO0014217 | 3/2000 |
| WO | WO0015256 | 3/2000 |
| WO | WO0054803 | 9/2000 |
| WO | WO0061151 | 10/2000 |
| WO | WO0067023 | 11/2000 |
| WO | WO0067787 | 11/2000 |
| WO | WO0135991 | 5/2001 |
| WO | WO0145750 | 6/2001 |
| WO | WO0183503 | 11/2001 |
| WO | WO0185751 | 11/2001 |
| WO | WO0193902 | 12/2001 |
| WO | WO0228428 | 4/2002 |
| WO | WO03014316 | 2/2003 |
| WO | WO03015711 | 2/2003 |
| WO | WO03035836 | 5/2003 |
| WO | WO03057822 | 7/2003 |
| WO | WO03094963 | 11/2003 |
| WO | WO2004007743 | 1/2004 |
| WO | WO2004026888 | 4/2004 |
| WO | WO2004094671 | 11/2004 |
| WO | WO2005004910 | 1/2005 |
| WO | WO2005023289 | 3/2005 |
| WO | WO2005030259 | 4/2005 |
| WO | WO2005042018 | 5/2005 |

OTHER PUBLICATIONS

Threadgill et al., Mitogenic synthetic polynucleotides suppress the antibody response to a bacterial polysaccharide. Vaccine. Jan. 1998; 16(1):76-82.

Tokunaga, Response of the organism to DNA—With a focus on immunostimulatory DNA. Yes Kansen Ensho Meneki. 2001 Autumn; 31 (3): 1-12. Japanese.

Uhlmann et al., Recent advances in the development of immunostimulatory oligonucleotides. Curr Opin Drug Discov Devel. Mar. 2003;6(2):204-17.

Uhlmann et al., Use of minimally modified antisense oligonucleotides for specific inhibition of gene expression. Methods EnzvmoL 2000;313:268-84.

Uhlmann, Oligonucleotide technologies: synthesis, production, regulations and applications. Nov. 29-30, 2000, Hamburg, Germany. Expert Opin Biol Ther. Mar. 2001; 1(2):319-28.

Verthelyi et al., Human peripheral blood cells differentially recognize and respond to two distinct CPG motifs. J ImmunoL Feb. 15, 2001; 166(4):2372-7.

Vollmer et al., Characterization of three CpG oligodeoxynucleotide classes with distinct immunostimulatory activities. Eur J ImmunoL Jan. 2004;34(1):251-62.

Vollmer et al., Highly immunostimulatory CpG-free oligodeoxynucleotides for activation of human leukocytes. Antisense Nucleic Acid Drug Dev. Jun. 2002; 12(3): 165-75.

Vollmer et al., Identification of a new class of CpG oligonucleotides capable of inducing both B cell proliferation and high IFN-alpha secretion from PBMC of HCV chronic carriers. Antiv Ther. 2002;7:L 115.

Vollmer et al., Impact of modifications of heterocyclic bases in CpG dinucleotides on their immune-modulatory activity. J Leukoc Biol. Sep. 2004;76(3):585-93. Epub Jun. 24, 2004.

Vollmer et al., Modulation of CpG oligodeoxynucleotide-mediated immune stimulation by locked nucleic acid (LNA). Oligonucleotides. 2004 Spring; 14(1):23-31.

Vollmer, Progress in drug development of immunostimulatory CpG oligodeoxynucleotide ligands for TLR9. Expert Opin Bioi Ther. May 2005;5(5):673-82. Review.

Vollmer, TLR9 in health and disease. Int Rev ImmunoL May-Aug. 2006;25(3-4): 155-81.

Wagner, Interactions between bacterial CpG-DNA and TLR9 bridge innate and adaptive immunity. CUIT Opin Microbiol. Feb. 2002;5(1):62-9.

Wang et al., Immunomodulatory oligonucleotides as novel therapy for breast cancer: pharmacokinetics, in vitro and in vivo anticancer activity, and potentiation of antibody therapy. Mol Cancer Ther. Aug. 2006;5(8):2106-14.

Weiner et al., The immunobiology and clinical potential of immunostimulatory CpG oligodeoxynucleotides. J Leukoc Biol. Oct. 2000;68(4):455-63.

Whitmore et al., LPD lipopolyplex initiates a potent cytokine response and inhibits tumor growth. Gene Ther. 1999;6:1867-75.

Whitmore et al., Systemic administration of LPD prepared with CpG oligonucleotides inhibits the growth of established pulmonary metastases by stimulating innate and acquired antitumor immune responses. Canc Immun Immunother. 200 I;50:503-14.

Wilson et al., Immune mechanisms and therapeutic potential of CpG oligodeoxynucleotides. Int Rev Immunol. May-Aug. 2006;25(3-4):183-213. Review.

Yamamoto et al., Ability of oligonucleotides with certain palindromes to induce interferon production and augment natural killer cell activity is associated with their base length. Antisense Res Dev. 1994 Summer;4(2): 119-22.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

(56) References Cited

OTHER PUBLICATIONS

Yamamoto et al., Synthetic oligonucleotides with certain palindromes stimulate interferon production of human peripheral blood lymphocytes in vitro. Jpn J Cancer Res. Aug. 1994;85(8):775-9.
Yu et al., Accessible 5'-end of CpG-containing phosphorothioate oligodeoxynucleotides is essential for immunostimulatory activity. Bioorg Med Chern Lett. Dec. 4, 2000; 10(23):2585-8.
Yu et al., 'Immunomers'—novel 3'-3'—linked CpG oligodeoxyribonucleotides as potent immunomodulatory agents. Nucleic Acids Res. Oct. 15, 2002;30(20):4460-9.
Yu et al., Immunostimulatory activity ofCpG oligonucleotides containing non-ionic methylphosphonate linkages. Bioorg Med Chern. Nov. 2001;9(11):2803-8.
Yu et al., Modulation of immunostimulatory activity of CpG oligonucleotides by site-specific deletion of nucleobases. Bioorg Med Chern Lett. Sep. 3, 2001; 11 (17):2263-7.
Yu et al., Potent CpG oligonucleotides containing phosphodiester linkages: in vitro and in vivo immunostimulatory properties. Biochem Biophys Res Commun. Sep. 13, 2002;297(1):83-90.
Zhao et al., Immunostimulatory activity ofCpG containing phosphorothioate oligodeoxynucleotide is modulated by modification of a single deoxynucleoside. Bioorg Med Chern Lett. May 15, 2000;10(10):1051-4. Abstract Only.
Zhao et al., Site of chemical modifications in CpG containing phosphorothioate oligodeoxynucleotide modulates its immunostimulatory activity. Bioorg Med Chern Lett. Dec. 20, 1999;9(24):3453-8.
Press Release, Hybridon, Inc. Hybridon shows immonumodulatory activity of synthetic oligonucleotides. Cambrige, MA. May 7, 2001.
Agrawal et al., Absorption, tissue distribution and in vivo stability in rats of a hybrid antisense oligonucleotide following oral administration. Biochem Pharmacol. Aug. 8, 1995;50(4):571-6.
Agrawal et al., Novel immunomodulatory oligonucleotides prevent development of allergic airway inflammation and airway hyperresponsiveness in asthma. Int Immunopharmacol. Jan. 2004;4(1): 127-38.
Agrawal et al., Pharmacokinetics of antisense oligonucleotides. Clin Pharrnacokinet. Jan. 1995;28(1):7-16.
Agrawal et al., Pharmacokinetics of oligonucleotides. Ciba Found Symp. 1997;209:60-75; discussion 75-8.
Agrawal et al., Pharmacokinetics, biodistribution, and stability of oligodeoxynucleotide phosphorothioates in mice. Proc Natl Acad Sci USA. Sep. 1, 1991;88(17):7595-9.
Agrawal, Importance of nucleotide sequence and chemical modifications of antisense oligonucleotides. Biochim Biophys Acta. Dec. 10, 1999;1489(1):53-68. Review.
Ahluwalia et al., Immunostimulatory profiles from two classes of CpG ODN administered subcutaneously to healthy subjects. ICI FOCIS 2004. Poster.
Bauer et al., Human TLR9 confers responsiveness to bacterial DNA via species-specific CpG motif recognition. Proc Natl Acad Sci USA. Jul. 31, 2001;98(16):9237-42.
Bhagat et al., CpG penta- and hexadeoxyribonucleotides as potent immunomodulatory agents. Biochem Biophys Res Commun. Jan. 24, 2003;300(4):853-61.
Boggs et al., Characterization and modulation of immune stimulation by modified oligonucleotides. Antisense Nucleic Acid Drug Dev. Oct. 1997;7(5):461-71.
Boujrad et al., Inhibition of hormone-stimulated steroidogenesis in cultured Leydig tumor cells by a cholesterol-linked phosphorothioate oligodeoxynucleotide antisense to diazepam-binding inhibitor. Proc Natl Acad Sci USA. Jun. 15, 1993;90(12):5728-31.
Cooper et al., Safety and immunogenicity of CPG 7909 injection as an adjuvant to Fluarix influenza vaccine. Vaccine. Aug. 13, 2004;22(23-24):3136-43.
Crooke et al., Phosphorothioate Oligonucleotides. Therapeut Apps. 1995;ch5:63-84.
Dalpke et al., CpG-DNA as immune response modifier. Int J Med Microbiol. Oct. 2004;294(5):345-54.

Fathi et al., Oligonucleotides with novel, cationic backbone substituents: aminoethylphosphonates.Nucleic Acids Res. Dec. 11, 1994;22(24):5416-24.
Ferrari et al., Characterization of antisense oligonucleotides comprising 2'-deoxy-2'-fluoro-BD-arabinonucleic acid (FANA). Acad Sci. 2006; 1082:91-1 02.
Ferrer et al., Preparation and properties of oligodeoxynucleotides containing 5-iodouracil and 5-bromo- and 5-iodocytosine. Bioconjug Chern. Sep.-Oct. 1997;8(5):757-61.
Goldberg et al., Beyond danger: unmethylated CpG dinucleotides and the immunopathogenesis of disease. Immunol Lett. Jul. 3, 2000;73(1):13-8.
Gouttefangeas et al., Problem solving for tumor immunotherapy. Nat Biotechnol. May 2000; 18(5):491-2.
Hafner et al., Antimetastatic effect ofCpG DNA mediated by type I IFN. Cancer Res. Jul. 15, 2001;61(14):5523-8.
Hartmann et al., Delineation of a CpG phosphorothioate oligodeoxynucleotide for activating primate immune responses in vitro and in vivo. J Immunol. Feb. 1, 2000; 164(3): 1617-24.
Heeg et al., CpG DNA as a Thl trigger. Int Arch Allergy Immunol. Feb. 2000;121(2):87-97.
Hoheisel et al., Quantitative measurements on the duplex stability of 2,6-diaminopurine and 5-chloro-uracil nucleotides using enzymatically synthesized oligomers. FEBS Lett. Nov. 12, 1990;274(1-2): 103-6.
Iho et al., Oligodeoxynucleotides containing palindrome sequences with internal5'-CpG-3' act directly on human NK and activated T cells to induce IFN-gamma production in vitro. J Immunol. Oct. 1, 1990; 163(7):3642-52.
Jiang et al., Enhancing immunogenicity by CpG DNA. Curr Opin Mol Ther. Apr. 2003;5(2): 180-5.
Kalota et al., 2'-deoxy-2'-fluoro-beta-D-arabinonucleic acid (2'F-ANA) modified oligonucleotides (ON) effect highly efficient, and persistent, gene silencing. Nucleic Acids Res. Jan. 18, 2006;34(2):451-61. Print 2006.
Kandimalla et al., A dinucleotide motif in oligonucleotides shows potent immunomodulatory activity and overrides species-specific recognition observed with CpG motif. Proc Natl Acad Sci USA. Nov. 25, 2003; 100(24): 14303-8. Epub Nov. 10, 2003.
Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31 (9):2393-400.
Kandimalla et al., Effect of chemical modifications of cytosine and guanine in a CpG-motif of oligonucleotides: structure-immunostimulatory activity relationships. Bioorg Med Chem. Mar. 2001;9(3):807-13.
Kandimalla et al., Immunomodulatory oligonucleotides containing a cytosine-phosphate-2'-deoxy-7-deazaguanosine motif as potent toll-like receptor 9 agonists. Proc Natl Acad Sci USA. May 10, 2005;102(19):6925-30. Epub Apr. 28, 2005.
Kandimalla et al., Secondary structures in CpG oligonucleotides affect immunostimulatory activity. Biochem Biophys Res Commun. Jul. 2003;306(4):948-53.
Kandimalla et al., Towards optimal design of second-generation immunomodulatory oligonucleotides. Curr Opin Mol Ther. Apr. 2002;4(2): 122-9.
Kim et al., A series of nonpolar thymidine analogues of increasing size: DNA base pairing and stacking properties. J Org Chem. Mar. 18, 2005;70(6):2048-53.
Kimura et al., Binding of oligoguanylate to scavenger receptors is required for oligonucleotides to augment NK cell activity and induce IFN. J Biochem (Tokyo). Nov. 1994; 116(5):991-4.
Klinman et al., CpG motifs present in bacterial DNA rapidly induce lymphocytes to secrete interleukin 6, interleukin 12, and interferon gamma. Proc Natl Acad Sci USA. Apr. 2, 1996;93(7):2879-83.
Klinman et al., Immune recognition of foreign DNA: a cure for bioterrorism? Immunity. Aug. 1999; 11 (2): 123-9.
Klinman et al., Immunotherapeutic applications of CpG-containing oligodeoxynucleotides. Drug News Perspect. Jun. 2000;13(5):289-96.
Klinman et al., Immunotherapeutic uses ofCpG oligodeoxynucleotides. Nat Rev Immunol. Apr. 2004;4(4):1-10.

(56) References Cited

OTHER PUBLICATIONS

Klinman et al., Synthetic oligonucleotides as modulators of intlammation. J Leukoc Biol. Oct. 2008;84(4): 1-7. Epub Apr. 22, 2008.
Krieg et al., Applications of immune stimulatory CpG DNA for antigen-specific and antigen-nonspecific cancer immunotherapy. Eur J Canc. Oct. 1999; 35/Suppl4:S10. Abstract #14.
Krieg et al., Bacterial DNA or oligonucleotides containing CpG motifs protect mice from lethal L. monocytogenes challenge. 1996 Meeting on Molecular Approaches to the Control of Infectious Diseases. Cold Spring Harbor Laboratory, Sep. 9-13, 1996: 116.
Krieg et al., Causing a commotion in the blood: immunotherapy progresses from bacteria to bacterial DNA. Immunol Today. Oct. 2000;21(10):521-6.
Krieg, Chapter 17:Immune stimulation by oligonucleotides. In Antisense Drug Tech. 2001; 1394:471-515.
Krieg et al., CpG DNA induces sustained IL-12 expression in vivo and resistance to Listeria monocytogenes challenge. J Immunol. Sep. 1, 1998; 161 (5):2428-34.
Krieg, CpG motifs in bacterial DNA and their immune effects. Annu Rev Immunol. 2002;20:709-60.
Krieg et al., Enhancing vaccines with immune stimulatory CpG DNA. Curr Opin Mol Ther. Feb. 2001;3( 1): 15-24.
Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec 2004.;27(6):460-71.
Krieg et al., Mechanism of action of CpG DNA. CUIT Top Microbiol Immunol. 2000;247: 1-21.
Krieg et al., Mechanisms and applications of immune stimulatory CpG oligodeoxynucleotides. Biochim Biophys Acta. Dec. 10, 1999;1489(1)107-16.
Krieg et al., Mechanisms and therapeutic applications of immune stimulatory CpG DNA. Pharmacol Ther. Nov. 1999;84(2): 113-20.
Krieg et al., P-chirality-dependent immune activation by phosphorothioate CpG oligodeoxynucleotides. Oligonucleotides. 2003; 13(6):491-9.
Krieg et al., The role of CpG dinucleotides in DNA vaccines. Trends Microbiol. Jan. 1998;6(1):23-7.
Krieg, An innate immune defense mechanism based on the recognition of CpG motifs in microbial DNA. J Lab Clin Med. Aug. 1996;128(2):128-33.
Krieg, Chapter 7: CpG oligonucleotides as immune adjuvants. Ernst Schering Research Found Workshop 2001; 30: 105-18.
Krieg, Chapter 8: Immune Stimulation by Oligonucleotides. In: Antisense Research and Application. Crooke, Ed. 1998:243-62.
Krieg, CpG DNA: a novel immunomodulator. Trends Microbiol. Feb. 1999;7(2):64-5.
Krieg, Immune effects and mechanisms of action of CpG motifs. Vaccine. Nov. 8, 2001;19(6):618-22.
Krieg, Infection. In: McGraw Hill Book. 1996:242-3.
Krieg, Lymphocyte activation by CpG dinucleotide motifs in prokaryotic DNA. Trends Microbiol. Feb. 1996;4(2):73-6.
Krieg, Now I know my CpGs.Trends Microbiol. Jun. 2001;9(6):249-52.
Krieg, Signal transduction induced by immunostimulatory CpG DNA. Springer Semin Immunopathol. 2000;22(1-2):97-105.
Krieg, The CpG motif: Implications for clinical immunology. BioDrugs. Nov. I 1998; I0(5):341-6.
Krieg, The role of CpG motifs in innate immunity. CUIT Opin Immunol. Feb. 2000;12(I):35-43.
Krieg, Therapeutic potential of Toll-like receptor 9 activation. Nat Rev Drug Discov. Jun. 2006;5(6):471-84.
Letsinger et al., Cholesteryl-conjugated oligonucleotides: synthesis, properties, and activity as inhibitors of replication of human immunodeficiency virus in cell culture. Prec Nat! Acad Sci USA. Sep. 1989;86(17):6553-6.
Letsinger et al., Synthesis and properties of modified oligonucleotides. Nucleic Acids Symp Ser. 1991;(24):75-8.

Lipford et al., Immunostimulatory DNA: sequence-dependent production of potentially harmful or useful cytokines. Eur J Immunol. Dec. 1997;27(12):3420-6.
Lipford et al., CpG-containing synthetic oligonucleotides promote B and cytotoxic T cell responses to protein antigen: a new class of vaccine adjuvants. Eur J Immunol. Sep. 1997;27(9):2340-4.
Liu et al., CpG ODN is an effective adjuvant in immunization with tumor antigen. J Invest Med. Sep. 7, 1997;45(7):333A.
Martin-Orozco et al., Enhancement of antigen-presenting cell surface molecules involved in cognate interactions by immunostimulatory DNA sequences. Int Immuno!. Jul. 1999; II (7): 1111-8.
McCluskie et al., The role of CpG in DNA vaccines. Springer Semin Immunopathoi. 2000;22(1-2): 125-32.
Messina et al., The influence of DNA structure on the in vitro stimulation of murine lymphocytes by natural and synthetic polynucleotide antigens. Cell Immunoi. Mar. 1993; 147(1): 148-57.
Moran et al., A thymidine triphosphate shape analog lacking Watson-Crick pairing ability is replicated with high sequence selectivity. Proc Natl Acad Sci USA. Sep. 30, 1997;94(20): 10506-11.
Mutwiri et al., Biological activity of immunostimulatory CpG DNA motifs in domestic animals. Vet Immunol Immunopathol. Jan. 30, 2003;91 (2):89-103.
Mutwiri et al., Strategies for enhancing the immunostimulatory effects ofepG oligodeoxynucleotides. J Control Release. May 31, 2004 ;97(1): 1-17.
Pavlick et al., Novel therapeutic agents under investigation for malignant melanoma. Expert Opin Investig Drugs. Sep. 2003; 12(9): 1545-58.
Payette et al., History of vaccines and positioning of current trends. Curr Drug Targets Infect. Disord. Nov. 2001;I(3):241-7.
Peng et al., G-quadruplex induced stabilization by 2'-deoxy-2'-fluoro-D-arabinonucleic acids (2'FANA). Nucleic Acids Res. 2007;35(15):4977-88. Epub Jul. 17, 2007.
Pisetsky et al., Stimulation of in vitro proliferation of murine lymphocytes by synthetic oligodeoxynucleotides. Mol Biol Rep. Oct. 1993; 18(3):217-21.
Pisetsky et al., The influence of base sequence on the immunological properties of defined oligonucleotides. Immunopharmacology. Nov. 1998;40(3): 199-208.
Pisetsky, Immunologic consequences of nucleic acid therapy. Antisense Res Dev. 1995 Fall;5(3):219-25.
Pisetsky, The influence of base sequence on the immunostimulatory properties of DNA. Immunol Res. 1999;19(1):35-46.
Polanczyk et al., Immunostimulatory effects of DNA and CpG motifs. Cent Eur J of Immunoi. 2000;25(3): 160-6.
Rankin et al., CpG motif identification for veterinary and laboratory species demonstrates that sequence recognition is highly conserved. Antisense Nucleic Acid Drug Dev. Oct. 2001; 11(5):333-40.
Ray et al., Oral pretreatment of mice with immunostimulatory CpG DNA induces reduced susceptibility to Listeria monocytogenes. Experimental Biology 2001. Orlando, Florida, USA. Mar. 31-Apr. 4, 2001. Abstracts, part II. FASEB 1. Mar. 8, 2001; 15(5):A I007.
Readett et al., PF-35 12676 (CPG7909) a Toll-like receptor 9 agonist—status of development for non-small cell lung cancer (NSCLC). Abstract PD3-1-6. Pfizer. Aug. 24, 2007. Poster.
Reddy et al., Design of synthetic immunostimulatory motifs as agonists of Toll-like receptor 9: Use of N3-methyl-dC and NI-methyl-dG. 231 51 ACS National Meeting. Atlanta, GA, United States. Mar. 26-30, 2006. Meeting Abstract.
Rothenfusser et al., Recent advances in immunostimulatory CpG oligonucleotides. Curr Opin Mol Ther. Apr. 2003;5(2):98-106.
Rudginsky et al., Antitumor activity of cationic lipid complexed with immunostimulatory DNA. Mol Ther. Oct. 2001;4(4):347-55.
Sato et al., Immunostimulatory DNA sequences necessary for effective intradermal gene immunization. Science. Jul. 19, 1996;273(5273):352-4.
Satoh et al., The study of mechanisms in CpG oligodeoxynucleotides-induced aggravation in murine allergic contact ermatitis to 2,4-dinitrofluorobenzene. Fukushima Igaku Zasshi. 2002;52(3):237-50. Abstract.

(56) References Cited

OTHER PUBLICATIONS

Schwartz et al., Bacterial DNA or oligonucleotides containing unmethylated CpG motifs can minimize lipopolysaccharide-induced inflammation in the lower respiratory tract through an IL-12-dependent pathway. J ImmunoL Jul. 1, 1999; 163(1):224-31.
Schweitzer et al., Hydrophobic, Non-Hydrogen-Bonding Bases and Base Pairs in DNA. J Am Chem Soc. Feb. 22, 1995; 117(7): 1863-1872.
Shao et al., CpG-containing oligodeoxynucleotide 1826 converts the weak uveitogenic rat interphotoreceptor retinoid-binding protein peptide 1181-1191 into a strong uveitogen. J ImmunoL Nov. 1, 2003;171(9):4780-5.
Sonehara et al., Hexamer palindromic oligonucleotides with 5'-CG-3' motif(s) induce production of interferon. J Interferon Cytokine Res. Oct. 1996; 16(10):799-803.
Stein et al., Non-antisense effects of oligodeoxynucleotides. Antisense Technology. 1997; chII: 241-64.
Stunz et al., Inhibitory oligonucleotides specifically block effects of stimulatory CpG oligonucleotides in B cells. Eur J ImmunoL May 2002;32(5): 1212-22.
Tokunaga et al., "A Synthetic Single-Stranded DNA, Poly(dG,dC), Induces Interferon-alpha/beta and -gamma, Augments Natural Killer Activity, and Suppresses Tumor Growth", Jpn. J. Cancer Res. (Gann), 79:682-686, 1988.
Tokunaga et al., "Antitumor Activity of Deoxyribonucleic Acid Fraction From Mycobacterium bovis BCG. I. Isolation, Physicochemical Characterization, and Antitumor Activity", JNCI, 72(4):955-962, 1984.
Messina et al., "Stimulation of in Vitro Murine Lymphocyte Proliferation by Bacterial DNA", The Journal of Immunology, 147(6):1759-1764, 1991.
Krieg, "Leukocyte Stimulation by Oligodeoxynecleotides", Applied Antisense Oligonucleotide Technology, Edited by CA Stein and Arthur M Krieg, Wiley-Liss, Inc., pp. 431-448,1998.
Krieg et al., "CpG motifs in bacterial DNA trigger direct B-cell activation", Nature, 374.
Krieg, "Mechanisms and applications of immune stimulatory CpG oligodeoxynucleotides", Biochimica et Biophysica Acta, 1489:107-116, 1999.
Hartmann et al., "CpG DNA: A potent signal for growth, activation, and maturation of human dendritic cells", Proc. Natl. Acad. Sci. USA, 96:9305-9310, 1999.
Pisetsky, "The Immunologic Properties of DNA", J. Immunol., 156:421-423, 1996.
Haecker et al., "CpG-DNA-specific activation of antigen-presenting cells requires stress kinase activity and is preceded by non-specific endocylosis and endosomal maturation", The EMBO Journal, 17(21):6230-6240, 1998.
Lipford et al., "Bacterial DNA as immune cell activator", Trends in Microbiol., 6:496-500, 1998.
Yi et al., CpG Oligodeoxyribonucleotides Rescue Mature Spleen B Cells from Spontaneous Apoptosis and Promote Cell Cycle Entry, The Journal of Immunology, 160:5898-5906, 1998.
Liang et al., "Activation of Human B Cells by Phosphorothioate Oligodeoxynucleotides", J. Clin. Invest., 98 (5):1119-1129,1996.
Tsao and Maki, "Optically Detected Magnetic Resonance Study of the Interaction of an Arsenic(III) Derivative of Cacodylic Acid with EcoRI Methyl Transferase", Biochemistry, 30(18):4565-4572, 1991.
Agrawal and Kandimalla, "Medicinal chemistry and therapeutic potential of CpG DNA", Trends in Molecular Medicine, 8(3):114-121, 2002.
Uhlmann & Vollmer, "Recent advances in the development of immunostimulatory oligonucleotides", Current Opinion in Drug Discovery & Development, 6(2):204-217, 2003.
Iyer et al., "Modified oligonucleotides—synthesis, properties and applications", Current Opinion in Molecular Therapeutics, 1(3):344-358, 1999.

CAS Registry File RN 123491-88-3, STN Entry Date Nov. 3, 1989.
CAS Registry File RN 124209-40-1, STN Entry Date Dec. 8, 1989.
CAS Registry File RN 129000-20-0, STN Entry Date Aug. 24, 1990.
CAS Registry File RN 129000-23-3, STN Entry Date Aug. 24, 1990.
CAS Registry File RN 148802-34-0, STN Entry Date Jul. 21, 1993.
CAS Registry File RN 148802-36-2, STN Entry Date Jul. 21, 1993.
CAS Registry File RN 148823-80-7, STN Entry Date Jul. 22, 1993.
Abrescia et al., X-ray and NMR studies of the DNA oligomer d(ATATAT): Hoogsteen base pairing in duplex DNA. Biochemistry. Apr. 13, 2004;43(14):4092-100.
Chen et al., Probing the DNA kink structure induced by the hyperthermophilic chromosomal protein Sac7d. NucleicAcids Res. Jan. 14, 2005;33(1):430-8.
Golden et al., Crystal structure of a phage Twort group I ribozyme-product complex. Nat Struct Mol Biol. Jan. 2005; 12(1):82-9. Epub Dec. 5, 2004. Abstract.
Gruenberger et al., Effect of substitution of halogen or N3-methy derivatives of uridine for uridine in trinucleotide codons on their recognition by aminoacyl-14C-tRNA. Collection of Czechoslovak Chemical Communications. 1968;33(11):3858-65. Abstract.
Holz et al., Identification of the binding site for the extrahelical target base in N6-adenine DNA methyltransferases by photo-cross-linking with duplex oligodeoxyribonucleotides containing 5-iodouracil at the target position. J Biol Chem. May 21, 1991;274(21): 15066-72.
Jensen et al., Using in vitro selection to direct the covalent attachment of human immunodeficiency virus type 1 Rev protein to high-affinity RNA ligands. Proc Nat! Acad Sci U SA. Dec. 19, 1995;92(26):12220-4.
Kuramoto et al., Oligonucleotide sequences required for natural killer cell activation. Jpn J Cancer Res. Nov. 1992;83(11):1128-31.
Manetto et al., Complex sequence dependence by excess-electron transfer through DNA with different strength electron acceptors. Angew Chem Int Ed Engl. Dec. 23, 2006;45(2):318-21.
Ovchinnikov et al., Covalent binding of *Escherichia coli* RNA polymerase photosensitive analogs or decathymidylic acid. Bioorganicheskaya Khimiya. 1979;5(9):1410-21. Abstract.
Oyoshi et al., Efficient C2'alpha-hydroxylation of deoxyribose in protein-induced Z-form DNA. J Am Chem Soc. Feb. 12, 2003;125(6):1526-31.
Oyoshi et al., Photoreactivity of 5-iodouracil-containing DNA-Z alpha complex. Nucleic Acids Res Suppl. 2001;(1):123-4.
Panasenko et al., Synthesis of triuridylyl triphosphate modified with 2'-deoxyuridine—a model codon in a study of translation processes. Metody Molekul Biol 1986: 47-52. Abstract.
Schuerman et al., Exploration of the influence of 5-iodo-2'-deoxyuridine incorporation on the structure of d[CACG(IDU)G]. Acta Crystallogr D Biol Crystallogr. Aug. 2003;59(Pt 8):1525-8. Epub Jul. 23, 2003. Abstract.
Shevchenko et al., Solid-phase triester synthesis of modified triuridylates by using an efficient condensing reagent. Inst. Biol. Mol. Genet. 1988;3:416-21. Abstract.
Stawinski et al., Arylsulfonyltetrazoles, new coupling reagents and further improvements in the triester method for the synthesis of deoxyribooligonucleotides. Nucleic Acids Res. Feb. 1997;4(2):353-71. Abstract.
Tomari et al., A protein sensor for siRNA asymmetry. Science. Nov. 19, 2004;306(5700):1377-80. Supplemental Materials Included.
Watanabe et al., Efficient generation of 2'-deoxyuridin-5-yl at 5'-(G/C)AA(X)U(X)U-3' (X = Br, I) sequences in duplex DNA under UV irradiation. J Am Chem Soc. Jan. 12, 2005;127(1):44-5.
Watanabe et al., Efficient generation of 2'-deoxyuridin-5-yl at 5'-(G/C)AA(X)U(X)U-3' (X = Br, I) sequences in duplex DNA under UV-irradiation. Nucleic Acids Symp Ser (Oxf). 2004;(48): 19-20.
Xu et al., Highly efficient photochemical 2'-deoxyribonolactone formation at the diagonal loop of a 5-iodouracil-containing antiparallel G-quartet. J Am Chem Soc. May 26, 2004;126(20):6274-9.
Xu et al., Photoreactivity of 5-iodouracil-containing telomeric DNA. Nucleic Acids Res Suppl. 2003;(3):71-2.

\* cited by examiner

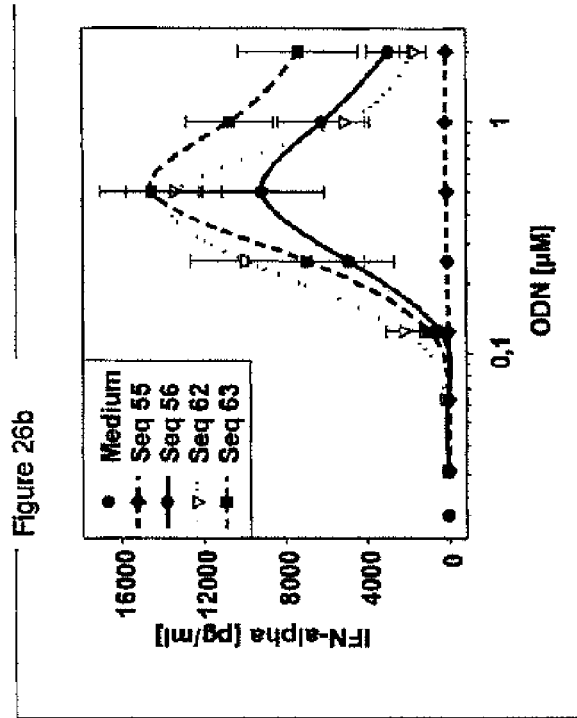
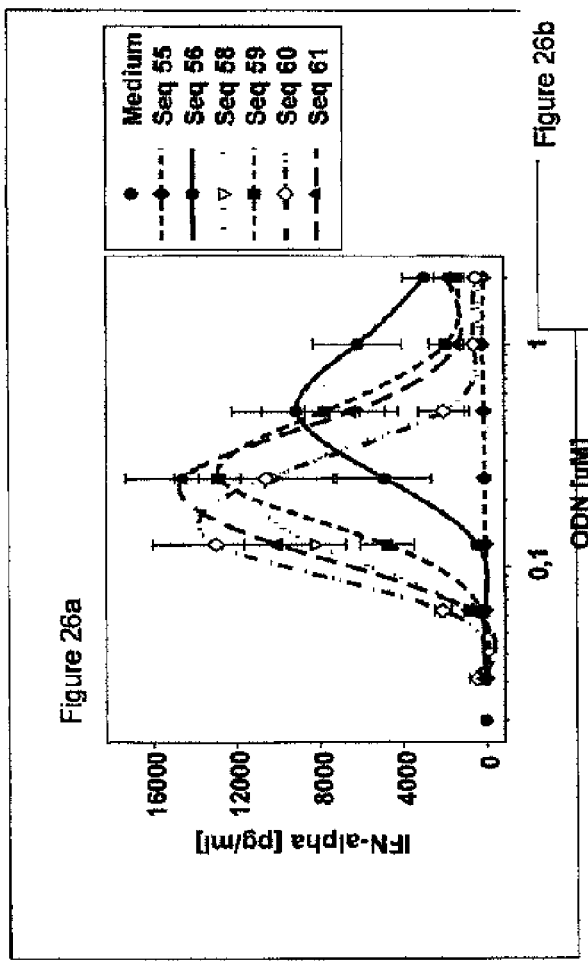

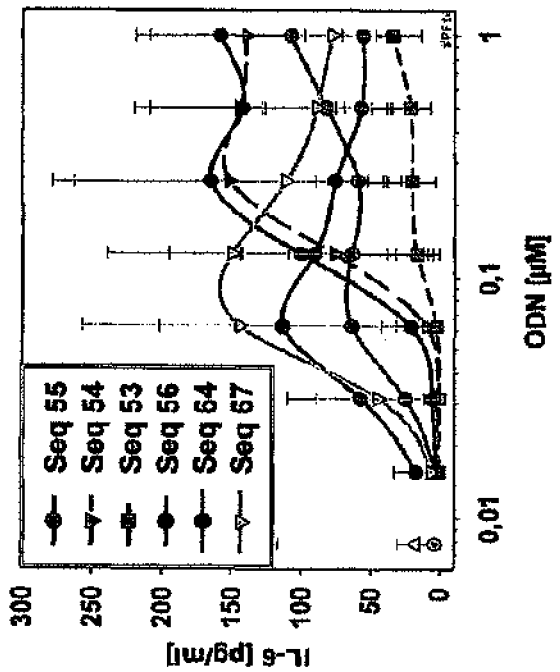
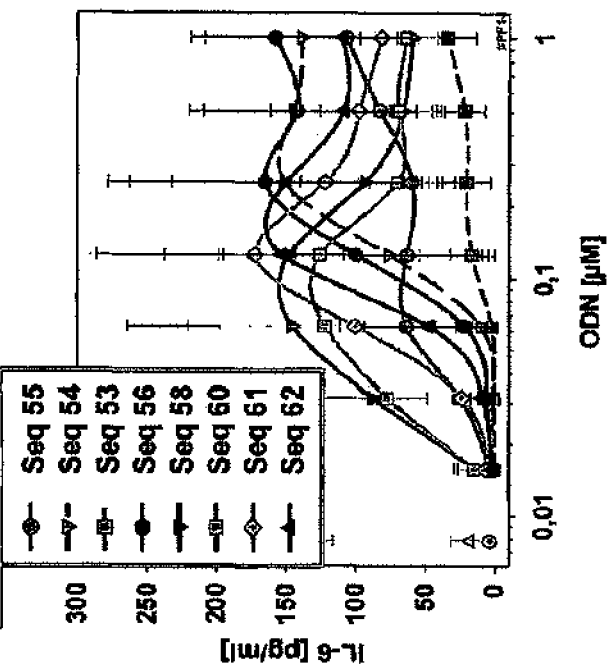
Figure 28

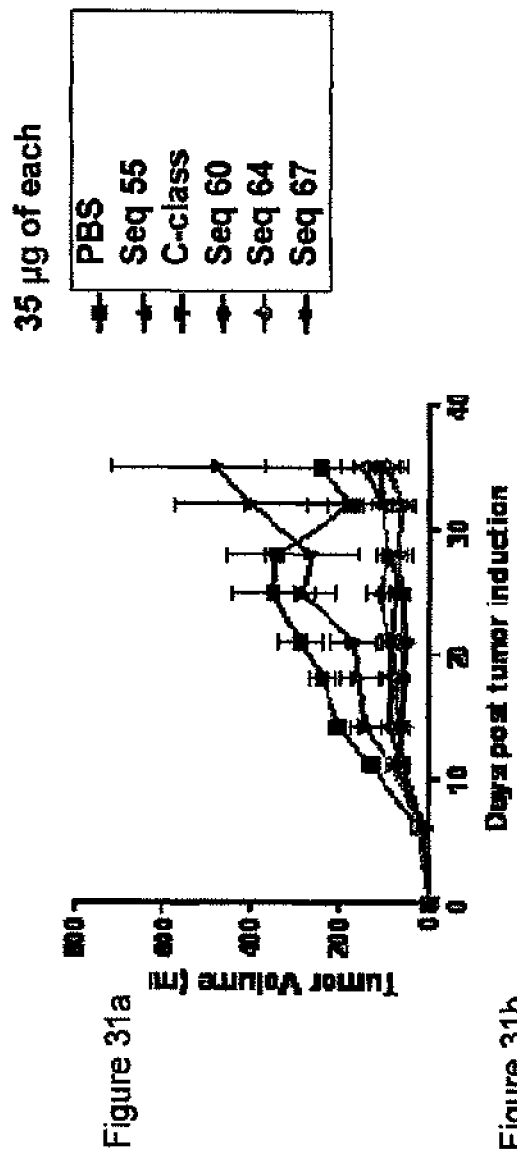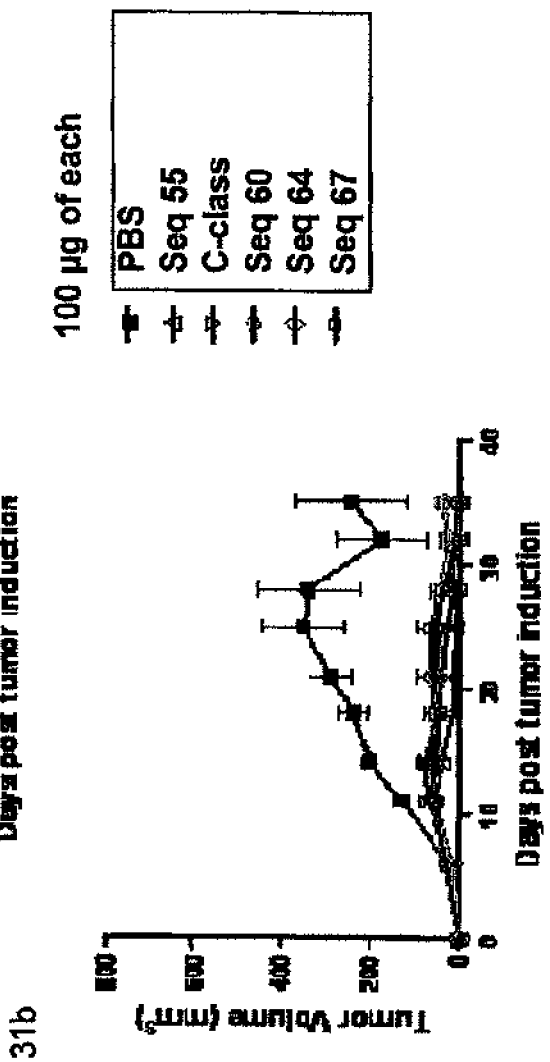
Figure 31a
Figure 31b

SEQUENCE LISTING

```
<160> NUMBER OF SEQ ID NOS: 198

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 1
tgtcgttttt tttttttttt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
tgtcgttttt tttttttttt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 2,4-difluorotoluene

<400> SEQUENCE: 3
tgncgttttt tttttttttt                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 2,4-difluorotoluene

<400> SEQUENCE: 4
tgtcgntttt tttttttttt                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 2,4-difluorotoluene
<220> FEATURE:
<221> NAME/KEY: misc_feature
<222> LOCATION: (6)..(6)
<223> OTHER INFORMATION: wherein n is 2,4-difluorotoluene

<400> SEQUENCE: 5
tgncgntttt tttttttttt                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 2,4-difluorotoluene
```

```
<400> SEQUENCE: 6
tgtngttttt tttttttttt                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: wherein n is 2,4-difluorotoluene

<400> SEQUENCE: 7
tgtcnttttt tttttttttt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 2,4-difluorotoluene

<400> SEQUENCE: 8 tncgttttt tttttttttt                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: wherein n is 2,4-difluorotoluene

<400> SEQUENCE: 9
tgtcgtnttt tttttttttt                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-bromo-2 prime-deoxyuridine

<400> SEQUENCE: 10 tgncttttt tttttttttt                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
```

-continued

<223> OTHER INFORMATION: wherein n is 5-bromo-2prime-deoxyuridine

<400> SEQUENCE: 11
tgtcgntttt tttttttttt                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-bromo-2 prime-deoxyuridine
<220> FEATURE:
<221> NAME/KEY: misc_feature
<222> LOCATION: (6)..(6)
<223> OTHER INFORMATION: wherein n is 5-bromo-2 prime-deoxyuridine

<400> SEQUENCE: 12
tgncgntttt tttttttttt                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 13
tgncgttttt tttttttttt                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 5-iodo-2 prime-deoxyuridine

<400> SEQUENCE: 14
tgtcgntttt tttttttttt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (6)..(6)
<223> OTHER INFORMATION: wherein n is 5-iodo-2 prime-deoxyuridine

<400> SEQUENCE: 15
tgncgntttt tttttttttt                                              20

-continued

```
<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is uridine

<400> SEQUENCE: 16
tgncgttttt tttttttttt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is uridine

<400> SEQUENCE: 17
tgtcgntttt tttttttttt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is uridine
<220> FEATURE:
<221> NAME/KEY: misc_feature
<222> LOCATION: (6)..(6)
<223> OTHER INFORMATION: wherein n is uridine

<400> SEQUENCE: 18
tgncgntttt tttttttttt                                               20

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 19
ncgtcgtttt tcggtcgttt t                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine
```

```
<400> SEQUENCE: 20
tcgncgtttt tcggtcgttt t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: wherein n is 5-iodo-2 prime-deoxyuridine

<400> SEQUENCE: 21
tcgtcgtttt tcggncgttt t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 22
ncgncgtttt tcggtcgttt t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine
<220> FEATURE:
<221> NAME/KEY: misc_feature
<222> LOCATION: (7)..(7)
<223> OTHER INFORMATION: wherein n is 5-iodo-2 prime-deoxyuridine

<400> SEQUENCE: 23
tcgncgnttt tcggtcgttt t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: wherein n is 5-iodo-2 prime-deoxyuridine
<220> FEATURE:
<221> NAME/KEY: misc_feature
<222> LOCATION: (18)..(18)
<223> OTHER INFORMATION: wherein n is 5-iodo-2 prime-deoxyuridine

<400> SEQUENCE: 24
tcgtcgtttt tcggncgntt t                                              21
```

-continued

```
<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
tcttttttgt cgtttttttt tt                                              22

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 26
tgctgctttt gtgcttttgt gctt                                            24

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 27
ncgtcgtttt acggcgccgt gccg                                            24

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 28
tcgncgtttt acggcgccgt gccg                                            24

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 5-ethyl-2 prime-deoxyuridine

<400> SEQUENCE: 29
tgtcgntttt tttttttttt                                                 20

<210> SEQ ID NO 30
<211> LENGTH: 20
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-ethyl-2 prime-deoxyuridine
<220> FEATURE:
<221> NAME/KEY: misc_feature
<222> LOCATION: (6)..(6)
<223> OTHER INFORMATION: wherein n is 5-ethyl-2 prime-deoxyuridine

<400> SEQUENCE: 30
tgncgntttt tttttttttt                                                    20

<210> SEQ ID NO 31
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 31
ncgtcgacga tcggcgcgcg ccg                                                23

<210> SEQ ID NO 32
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 32
tcgncgacga tcggcgcgcg ccg                                                23

<210> SEQ ID NO 33
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: n is a, c, g, or t

<400> SEQUENCE: 33
ncgncgacga tcggcgcgcg ccg                                                23

<210> SEQ ID NO 34
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(1)
<223> OTHER INFORMATION: wherein n is 5-iodo-2 prime-deoxyuridine

<400> SEQUENCE: 34
ncgacgtcgt ggggg                                                     15

<210> SEQ ID NO 35
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: wherein n is 5-iodo-2 prime-deoxyuridine

<400> SEQUENCE: 35
tcgacgncgt ggggg                                                     15

<210> SEQ ID NO 36
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: wherein n is 5-iodo-2 prime-deoxyuridine
<220> FEATURE:
<221> NAME/KEY: misc_feature
<222> LOCATION: (10)..(10)
<223> OTHER INFORMATION: wherein n is 5-iodo-2 prime-deoxyuridine

<400> SEQUENCE: 36
tcgacgncgn ggggg                                                     15

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 37
tcgtcgtttt tcggtcgttt t                                              21

<210> SEQ ID NO 38
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 38 gtcgtt                                                                6

<210> SEQ ID NO 39
<211> LENGTH: 6
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine
```

```
<400> SEQUENCE: 39 gncgtt                                                                    6

<210> SEQ ID NO 40
<211> LENGTH: 6
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine
<220> FEATURE:
<221> NAME/KEY: misc_feature
<222> LOCATION: (5)..(5)
<223> OTHER INFORMATION: wherein n is 5-iodo-2 prime-deoxyuridine

<400> SEQUENCE: 40 gncgnt                                                                    6

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-chloro-2 prime-deoxyuridine

<400> SEQUENCE: 41
tgncgttttt tttttttttt                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-ethyl-2 prime-deoxyuridine

<400> SEQUENCE: 42
tgncgttttt tttttttttt                                                    20

<210> SEQ ID NO 43
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 43
tcgacgtcgt ggggg                                                         15

<210> SEQ ID NO 44
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
```

```
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: n is a, c, g, or t

<400> SEQUENCE: 44
ncgncgtttt acggcgccgt gccg                                              24

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine
<220> FEATURE:
<221> NAME/KEY: misc_feature
<222> LOCATION: (7)..(7)
<223> OTHER INFORMATION: wherein n is 5-iodo-2 prime-deoxyuridine

<400> SEQUENCE: 45
tcgncgnttt acggcgccgt gccg                                              24

<210> SEQ ID NO 46
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
tcgtcgtttt acggcgccgt gccg                                              24

<210> SEQ ID NO 47
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is 5-iodo-2 prime-deoxyuridine

<400> SEQUENCE: 47
tcttttttgn cgttttttttt tt                                               22

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is 5-iodo-2 prime-deoxyuridine
<220> FEATURE:
<221> NAME/KEY: misc_feature
<222> LOCATION: (13)..(13)
<223> OTHER INFORMATION: wherein n is 5-iodo-2 prime-deoxyuridine

<400> SEQUENCE: 48
```
tcttttttgn cgnttttttt tt                                22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 49
ncttttttgt cgtttttttt tt                                22

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 50
ncttttttgt cgtttttttt tt                                22

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is uridine

<400> SEQUENCE: 51
tcttttttgn cgtttttttt tt                                22

<210> SEQ ID NO 52
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 52
tcgtcgacga tcggcgcgcg ccg                               23

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
tccaggactt ctctcaggtt                                   20

<210> SEQ ID NO 54
<211> LENGTH: 22
<212> TYPE: DNA
<213> ORGANISM: Artificial Sequence

```
<220> FEATURE:
<223> OTHER INFORMATION: Synthetic Oligonucleotide

<400> SEQUENCE: 54
tcgtcgtttt cggcgcgcgc cg                                              22

<210> SEQ ID NO 55
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 55
tcgtcgtttt gtcgttttgt cgtt                                            24

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 56
tcgacgtcga tcggcgcgcg ccg                                             23

<210> SEQ ID NO 57
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 57
tcgtcgacga tcggcggccg ccg                                             23

<210> SEQ ID NO 58
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 58
ncgacgtcga tcggcgcgcg ccg                                             23

<210> SEQ ID NO 59
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (1)..(23)
<223> OTHER INFORMATION: wherein all the internucleotide linkages are
      phosphorothioate linkages

<400> SEQUENCE: 59
ncgacgtcga tcggcgcgcg ccg                                             23
```

<210> SEQ ID NO 60
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 60
ncgacgtcga tcggcgcgcg ccgt                                           24

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (1)..(24)
<223> OTHER INFORMATION: wherein all the internucleotide linkages are
      phosphorothioate linkages

<400> SEQUENCE: 61
ncgacgtcga tcggcgcgcg ccgt                                           24

<210> SEQ ID NO 62
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 62
ncgacgtcga tcggcgcgcg ccg                                            23

<210> SEQ ID NO 63
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 63
ncgacgtcga tcggcgcgcg ccg                                            23

<210> SEQ ID NO 64
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature

```
<222> LOCATION: (1)..(1)
<223> OTHER INFORMATION: wherein n is 5-ethyl-2 prime-deoxyuridine

<400> SEQUENCE: 64
ncgacgtcga tcggcgcgcg ccg                                              23

<210> SEQ ID NO 65
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(23)
<223> OTHER INFORMATION: wherein all the internucleotide linkages are
      phosphorothioate linkages
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 65
ncgacgtcga tcggcgcgcg ccg                                              23

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 66
ncgtcgacga tcggcggccg ccgt                                             24

<210> SEQ ID NO 67
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 67
ncgtcgacga tcggcggccg ccgt                                             24

<210> SEQ ID NO 68
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 68
tcgcgtcgtt cggcgcgcgc cg                                               22

<210> SEQ ID NO 69
<211> LENGTH: 23
<212> TYPE: DNA
<213> ORGANISM: Artificial Sequence
<220> FEATURE:
<223> OTHER INFORMATION: Synthetic Oligonucleotide
```

```
<400> SEQUENCE: 69
tcgtcgacgt tcggcgcgcg ccg                                               23

<210> SEQ ID NO 70
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 70
tcggacgttc ggcgcgcgcc g                                                 21

<210> SEQ ID NO 71
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 71
tcggacgttc ggcgcgccg                                                    19

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tcgcgtcgtt cggcgcgccg                                                   20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
tcgacgttcg gcgcgcgccg                                                   20

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 74
tcgacgttcg gcgcgccg                                                     18

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 75
tcgcgtcgtt cggcgccg                                                     18

<210> SEQ ID NO 76
```

```
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 76
tcgcgacgtt cggcgcgcgc cg                                              22

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-fluoro-dU

<400> SEQUENCE: 77
tgncgttttt tttttttttt                                                 20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 5-fluoro-dU

<400> SEQUENCE: 78
tgtcgntttt tttttttttt                                                 20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-fluoro-dU
<220> FEATURE:
<221> NAME/KEY: misc_feature
<222> LOCATION: (6)..(6)
<223> OTHER INFORMATION: wherein n is 5-fluoro-dU

<400> SEQUENCE: 79
tgncgntttt tttttttttt                                                 20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is uridine
<220> FEATURE:
<221> NAME/KEY: misc_feature
<222> LOCATION: (6)..(6)
<223> OTHER INFORMATION: wherein n is uridine

<400> SEQUENCE: 80
```
tgncgntttt tttttttttt                                              20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: wherein n is 6-nitro-benzimidazol

<400> SEQUENCE: 81 tgtcntttt tttttttttt                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 6-nitro-benzimidazol
<220> FEATURE:
<221> NAME/KEY: misc_feature
<222> LOCATION: (4)..(5)
<223> OTHER INFORMATION: wherein the linkages is a phosphdiester linkage

<400> SEQUENCE: 82
tgtngttttt tttttttttt                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 6-nitro-benzimidazol
<220> FEATURE:
<221> NAME/KEY: misc_feature
<222> LOCATION: (4)..(6)
<223> OTHER INFORMATION: wherein the linkages are phosphodiester
      linkages

<400> SEQUENCE: 83
tgtngttttt tttttttttt                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 84
ngtcgttttt tttttttttt                                              20

<210> SEQ ID NO 85
<211> LENGTH: 20

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 85
ngncgttttt ttttttttt                                          20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: wherein n is 5-iodo-2 prime-deoxyuridine

<400> SEQUENCE: 86
tgtcgtnttt ttttttttt                                          20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is a,a,a-trifluoro-dT

<400> SEQUENCE: 87
tgncgttttt ttttttttt                                          20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is a,a,a-trifluoro-dT

<400> SEQUENCE: 88 tgtcgnttttt ttttttttt                                         20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is a,a,a-trifluoro-dT
<220> FEATURE:
<221> NAME/KEY: misc_feature
<222> LOCATION: (6)..(6)
```

<223> OTHER INFORMATION: wherein n is a,a,a-trifluoro-dT

<400> SEQUENCE: 89
tgncgntttt tttttttttt                                          20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-chloro-2 prime-deoxyuridine

<400> SEQUENCE: 90
tgncgttttt tttttttttt                                          20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 5-chloro-2 prime-deoxyuridine

<400> SEQUENCE: 91
tgtcgntttt tttttttttt                                          20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-chloro-2 prime-deoxyuridine
<220> FEATURE:
<221> NAME/KEY: misc_feature
<222> LOCATION: (6)..(6)
<223> OTHER INFORMATION: wherein n is 5-chloro-2 prime-deoxyuridine

<400> SEQUENCE: 92
tgncgntttt tttttttttt                                          20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine

<400> SEQUENCE: 93 tncgttttt tttttttttt                                           20

<210> SEQ ID NO 94
<211> LENGTH: 9
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 94 tgncgtttt                                                                    9

<210> SEQ ID NO 95
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 95
tgncgttttg tcgtt                                                            15

<210> SEQ ID NO 96
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (8)..(8)
<223> OTHER INFORMATION: wherein n is hexaethylenglycol phosphate
<220> FEATURE:
<221> NAME/KEY: misc_feature
<222> LOCATION: (9)..(9)
<223> OTHER INFORMATION: wherein n is Doubler2
<220> FEATURE:
<221> NAME/KEY: misc_feature
<222> LOCATION: (10)..(10)
<223> OTHER INFORMATION: wherein n is 3 prime-O-Methyl-rG

<400> SEQUENCE: 96 tgncgttnnn                                                                  10

<210> SEQ ID NO 97
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (8)..(8)
<223> OTHER INFORMATION: wherein n is hexaethylenglycol phosphate
<220> FEATURE:
<221> NAME/KEY: misc_feature
<222> LOCATION: (9)..(9)
<223> OTHER INFORMATION: wherein n is Doubler2
<220> FEATURE:
```

```
<221> NAME/KEY: misc_feature
<222> LOCATION: (10)..(10)
<223> OTHER INFORMATION: wherein n is 3 prime-O-Methyl-rG

<400> SEQUENCE: 97 ncgttcgnnn                                                              10

<210> SEQ ID NO 98
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 98
ttncgtcgtt tcgtcgtt                                                     18

<210> SEQ ID NO 99
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-bromo-2 prime-deoxyuridine

<400> SEQUENCE: 99
ncgacgtcgt ggggg                                                        15

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 100 tgngctttt tttttttttt                                                    20

<210> SEQ ID NO 101
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (8)..(8)
<223> OTHER INFORMATION: wherein n is hexaethylenglycol phosphate
<220> FEATURE:
<221> NAME/KEY: misc_feature
<222> LOCATION: (9)..(9)
<223> OTHER INFORMATION: wherein n is Doubler2
<220> FEATURE:
<221> NAME/KEY: misc_feature
<222> LOCATION: (10)..(10)
<223> OTHER INFORMATION: wherein n is triethylenglycol phosphate
```

<400> SEQUENCE: 101 tgncgttnnn					10

<210> SEQ ID NO 102
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (8)..(8)
<223> OTHER INFORMATION: wherein n is hexaethylenglycol phosphate
<220> FEATURE:
<221> NAME/KEY: misc_feature
<222> LOCATION: (9)..(9)
<223> OTHER INFORMATION: wherein n is Doubler2
<220> FEATURE:
<221> NAME/KEY: misc_feature
<222> LOCATION: (10)..(10)
<223> OTHER INFORMATION: wherein n is triethylenglycol phosphate

<400> SEQUENCE: 102 ncgttcgnnn					10

<210> SEQ ID NO 103
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 103
ncgtcgtttt cggcgcgcgc cg					22

<210> SEQ ID NO 104
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 104
tcgncgtttt cggcgcgcgc cg					22

<210> SEQ ID NO 105
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)

<223> OTHER INFORMATION: wherein n is 5-iodo-2 prime-deoxyuridine

<400> SEQUENCE: 105
tcgtcgtttn cggcgcgcgc cg                                              22

<210> SEQ ID NO 106
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (15)..(15)
<223> OTHER INFORMATION: wherein n is 5-iodo-2 prime-deoxyuridine

<400> SEQUENCE: 106
ncgtcgtttt tcggncgttt t                                               21

<210> SEQ ID NO 107
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-iodo-2 prime-deoxyuridine
<220> FEATURE:
<221> NAME/KEY: misc_feature
<222> LOCATION: (15)..(15)
<223> OTHER INFORMATION: wherein n is 5-iodo-2 prime-deoxyuridine

<400> SEQUENCE: 107
tcgncgtttt tcggncgttt t                                               21

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (16)..(16)
<223> OTHER INFORMATION: wherein n is 5-iodo-2 prime-deoxyuridine

<400> SEQUENCE: 108
tgncgttttt ttttgncgtt                                                 20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 109
tgncgttttt ttttttttttt					20

<210> SEQ ID NO 110
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (13)..(13)
<223> OTHER INFORMATION: wherein n is 7-deaza-dG

<400> SEQUENCE: 110
ncgacgtcgt ggngg					15

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 3 prime-O-Methyl-rG
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 111
tnncgttttt ttttttttt					20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (5)..(5)
<223> OTHER INFORMATION: wherein n is 3 prime-O-Methyl-rG

<400> SEQUENCE: 112
tgncnttttt ttttttttt					20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 3 prime-O-Methyl-rG
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:

```
<221> NAME/KEY: misc_feature
<222> LOCATION: (5)..(5)
<223> OTHER INFORMATION: wherein n is 3 prime-O-Methyl-rG

<400> SEQUENCE: 113 tnncntttt tttttttttt                                                    20

<210> SEQ ID NO 114
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 114
ncgncgtttt tcggtcgttt t                                                 21

<210> SEQ ID NO 115
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (1)..(21)
<223> OTHER INFORMATION: wherein all internucleotide linkages are
      phosphorothioate internucleotide linkages
<220> FEATURE:
<221> NAME/KEY: misc_feature
<222> LOCATION: (4)..(4)
<223> OTHER INFORMATION: wherein n is 5-iodo-2 prime-deoxyuridine

<400> SEQUENCE: 115
ncgncgtttt tcggtcgttt t                                                 21

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-proynyl-dU

<400> SEQUENCE: 116
tgncgttttt tttttttttt                                                   20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
```

```
<223> OTHER INFORMATION: wherein n is 5-proynyl-dU

<400> SEQUENCE: 117
tgtcgntttt tttttttttt                                          20

<210> SEQ ID NO 118
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-bromo-2 prime-deoxyuridine

<400> SEQUENCE: 118
ncgacgtcgt ggggg                                               15

<210> SEQ ID NO 119
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine

<400> SEQUENCE: 119
tgncgttttc ggcgcgcgcc g                                        21

<210> SEQ ID NO 120
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine

<400> SEQUENCE: 120
tncgttttcg gcgcgcgccg t                                        21

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-ethyl-2 prime-deoxyuridine

<400> SEQUENCE: 121
tncgtttttt tttttttttt                                          20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (3)..(3)
<223> OTHER INFORMATION: wherein n is 5-ethyl-2 prime-deoxyuridine

<400> SEQUENCE: 122 tgngctttt tttttttttt                                                20

<210> SEQ ID NO 123
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 123
ncgtcgtttt tcggtcgttt t                                             21

<210> SEQ ID NO 124
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 124
ncgtcgtttt tcggtcgttt t                                             21

<210> SEQ ID NO 125
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine
<220> FEATURE:
<221> NAME/KEY: misc_feature
<222> LOCATION: (7)..(7)
<223> OTHER INFORMATION: wherein n is hexadecylglyceryl

<400> SEQUENCE: 125 gncgttn                                                              7

<210> SEQ ID NO 126
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine
<220> FEATURE:
<221> NAME/KEY: misc_feature
<222> LOCATION: (5)..(5)
<223> OTHER INFORMATION: wherein n is 5-iodo-2 prime-deoxyuridine
<220> FEATURE:
<221> NAME/KEY: misc_feature
<222> LOCATION: (7)..(7)
<223> OTHER INFORMATION: wherein n is hexadecylglyceryl
```

<400> SEQUENCE: 126 gncgntn                                                                                      7

<210> SEQ ID NO 127
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-ethyl-2 prime-deoxyuridine
<220> FEATURE:
<221> NAME/KEY: misc_feature
<222> LOCATION: (5)..(5)
<223> OTHER INFORMATION: wherein n is 5-ethyl-2 prime-deoxyuridine
<220> FEATURE:
<221> NAME/KEY: misc_feature
<222> LOCATION: (7)..(7)
<223> OTHER INFORMATION: wherein n is hexadecylglyceryl

<400> SEQUENCE: 127 gncgntn                                                                                      7

<210> SEQ ID NO 128
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 128
ncgtcgtttt acggcgccgt gccg                                                                  24

<210> SEQ ID NO 129
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-ethyl-2 prime-deoxyuridine

<400> SEQUENCE: 129
tcgncgtttt acggcgccgt gccg                                                                  24

<210> SEQ ID NO 130
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 130
ncgtcgacga tcggcgcgcg ccg                                                                   23

<210> SEQ ID NO 131
<211> LENGTH: 17

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 131 ncttttttt tttttt                                                     17

<210> SEQ ID NO 132
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 132
nctttttttt cgttttttttt tt                                            22

<210> SEQ ID NO 133
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is 5-iodo-2 prime-deoxyuridine

<400> SEQUENCE: 133
tctttttttn cgttttttttt tt                                            22

<210> SEQ ID NO 134
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (10)..(10)
<223> OTHER INFORMATION: wherein n is 5-iodo-2 prime-deoxyuridine

<400> SEQUENCE: 134 ncttttttn cgttttttttt tt                                             22

<210> SEQ ID NO 135
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 135
```
ncgtcgtttc gtcgttttgt cgtt                                          24

<210> SEQ ID NO 136
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(20)
<223> OTHER INFORMATION: wherein n is 5-iodo-2 prime-deoxyuridine

<400> SEQUENCE: 136
tcgtcgtttc gtcgttttgn cgtt                                          24

<210> SEQ ID NO 137
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (20)..(20)
<223> OTHER INFORMATION: wherein n is 5-iodo-2 prime-deoxyuridine

<400> SEQUENCE: 137
ncgtcgtttc gtcgttttgn cgtt                                          24

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (5)..(5)
<223> OTHER INFORMATION: wherein n is 7-deaza-dG

<400> SEQUENCE: 138
tgncnttttt tttttttttt                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (5)..(5)
<223> OTHER INFORMATION: wherein n is inosine

<400> SEQUENCE: 139
tgncnttttt tttttttttt                                               20

```
<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: wherein n is 5-methyl-dC

<400> SEQUENCE: 140
tgnngttttt tttttttttt                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: wherein n is 5-iodo-2 prime-deoxyuridine

<400> SEQUENCE: 141
tgtcgttntt tttttttttt                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: wherein n is 5-iodo-2 prime-deoxyuridine

<400> SEQUENCE: 142
tgtcgtttnt tttttttttt                                              20

<210> SEQ ID NO 143
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 143
ncgtcgtttt cggcgcgcgc cgt                                          23

<210> SEQ ID NO 144
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
```

```
<400> SEQUENCE: 144
ncgtcgtttt cggcgcgcgc cgt                                              23

<210> SEQ ID NO 145
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: wherein n is 5-ethyl-2 prime-deoxyuridine

<400> SEQUENCE: 145
tcgncgtttt cggcgcgcgc cgt                                              23

<210> SEQ ID NO 146
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is 5-iodo-2 prime-deoxyuridine

<400> SEQUENCE: 146
tcgtcgtttn cggcgcgcgc cgt                                              23

<210> SEQ ID NO 147
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: wherein n is 5-ethyl-2 prime-deoxyuridine

<400> SEQUENCE: 147
tcgtcgtttn cggcgcgcgc cgt                                              23

<210> SEQ ID NO 148
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (10)..(10)
<223> OTHER INFORMATION: wherein n is 5-ethyl-2 prime-deoxyuridine

<400> SEQUENCE: 148
ncgtcgtttn cggcgcgcgc cgt                                              23

<210> SEQ ID NO 149
<211> LENGTH: 23
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine

<400> SEQUENCE: 149
ncgncgtttt cggcgcgcgc cgt                                             23

<210> SEQ ID NO 150
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine

<400> SEQUENCE: 150
ncgncgtttt cggcgcgcgc cgt                                             23

<210> SEQ ID NO 151
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 151
ncgtcgtttt gtcgttttgt cgtt                                            24

<210> SEQ ID NO 152
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 152
ncgtcgtttt gtcgttttgt cgtt                                            24

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 5-d-bromo-vinyl-uridine

<400> SEQUENCE: 153
```
tgncgttttt tttttttttt                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is 5-d-bromo-vinyl-uridine

<400> SEQUENCE: 154
tgtcgntttt tttttttttt                                              20

<210> SEQ ID NO 155
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 155
ncggcggccg ccg                                                     13

<210> SEQ ID NO 156
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 156
ncgtcgtttt acggcgccgt gccn                                         24

<210> SEQ ID NO 157
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 157
ncgtcgtttt acggcgccgt gccn                                         24

<210> SEQ ID NO 158
<211> LENGTH: 24
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<222> LOCATION: (1)..(24)
<223> OTHER INFORMATION: wherein all internucleotide linkages are
      phosphorothioate linkages
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 158
ncgncgtttt acggcgccgt gccn                                            24

<210> SEQ ID NO 159
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 159
ncgncgtttt acggcgccgt gccn                                            24

<210> SEQ ID NO 160
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (25)..(25)
<223> OTHER INFORMATION: wherein n is a 5 prime to 5 prime linked
      thymidine

<400> SEQUENCE: 160
ncgtcgtttt acggcgccgt gccgn                                           25

<210> SEQ ID NO 161
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
```

```
<223> OTHER INFORMATION: wherein n is 5-iodo-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 161
ncgtcgtttt cggcgcgcgc cn                                              22

<210> SEQ ID NO 162
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 162
ncgtcgtttt cggcgcgcgc cn                                              22

<210> SEQ ID NO 163
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 163
ncgtcgtttt cggcgcgcgc cn                                              22

<210> SEQ ID NO 164
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(22)
<223> OTHER INFORMATION: wherein all internucleotide linkages are
      phosphorothioate linkages
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 164
ncgncgtttt cggcgcgcgc cn                                              22
```

```
<210> SEQ ID NO 165
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (4)..(4)
<223> OTHER INFORMATION: wherein n is 5-ethyl-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 165
ncgncgtttt cggcgcgcgc cn                                              22

<210> SEQ ID NO 166
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (10)..(10)
<223> OTHER INFORMATION: wherein n is 5-ethyl-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 166
ncgtcgtttn cggcgcgcgc cn                                              22

<210> SEQ ID NO 167
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (10)..(10)
<223> OTHER INFORMATION: wherein n is 5-iodo-2 prime-deoxyuridine
<220> FEATURE:
<221> NAME/KEY: misc_feature
<222> LOCATION: (22)..(22)
<223> OTHER INFORMATION: wherein n is 3 prime-O-Methyl-rG

<400> SEQUENCE: 167
ncgtcgtttn cggcgcgcgc cn                                              22

<210> SEQ ID NO 168
<211> LENGTH: 23
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (23)..(23)
<223> OTHER INFORMATION: wherein n is a 5 prime to 5 prime linked
      thymidine

<400> SEQUENCE: 168
ncgtcgtttt cggcgcgcgc cgn                                              23

<210> SEQ ID NO 169
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (23)..(23)
<223> OTHER INFORMATION: wherein n is a 5 prime to 5 prime linked
      thymidine

<400> SEQUENCE: 169
ncgtcgtttt cggcgcgcgc cgn                                              23

<210> SEQ ID NO 170
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 170
ncgtcgacgt tcggcgccgt gccn                                             24

<210> SEQ ID NO 171
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (24)..(24)
<223> OTHER INFORMATION: wherein n is 3 prime-O-Methyl-rG

<400> SEQUENCE: 171
ncgtcgacgt tcggcgccgt gccn                                             24

<210> SEQ ID NO 172
<211> LENGTH: 23
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (23)..(23)
<223> OTHER INFORMATION: n is a, c, g, or t

<400> SEQUENCE: 172
ncgtcgacga tcggcgcgcg ccn                                              23

<210> SEQ ID NO 173
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (23)..(23)
<223> OTHER INFORMATION: wherein n is 3 prime-O-Methyl-rG

<400> SEQUENCE: 173
ncgtcgacga tcggcgcgcg ccn                                              23

<210> SEQ ID NO 174
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (25)..(25)
<223> OTHER INFORMATION: wherein n is a 5 prime to 5 prime linked
      thymidine

<400> SEQUENCE: 174
ncgtcgacgt tcggcgccgt gccgn                                            25

<210> SEQ ID NO 175
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine
<220> FEATURE:
<221> NAME/KEY: misc_feature
<222> LOCATION: (24)..(24)
<223> OTHER INFORMATION: wherein n is a 5 prime to 5 prime linked
      thymidine

<400> SEQUENCE: 175
ncgtcgacga tcggcgcgcg ccgn                                             24
```

```
<210> SEQ ID NO 176
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is nitroindol

<400> SEQUENCE: 176
tgncgttttt tttttttttt                                          20

<210> SEQ ID NO 177
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is nitropyrrol

<400> SEQUENCE: 177
tgncgttttt tttttttttt                                          20

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: wherein n is 6-nitro-benzimidazol

<400> SEQUENCE: 178
tgncgttttt tttttttttt                                          20

<210> SEQ ID NO 179
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 179
ncgtcgtttt tcggtcgttt t                                        21

<210> SEQ ID NO 180
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 180
ncgtcgacga tggcggcgcc gcc                                      23
```

<210> SEQ ID NO 181
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 181
ncgtcgacga tggcggcgcc gcc                                              23

<210> SEQ ID NO 182
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 182
ttcgttttcg gcgcgcgccg t                                                21

<210> SEQ ID NO 183
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-ethyl-2 prime-deoxyuridine

<400> SEQUENCE: 183
tncgttttcg gcgcgcgccg t                                                21

<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-iodo-2 prime-deoxyuridine

<400> SEQUENCE: 184
ncgttttcgg cgcgcgccgt                                                  20

<210> SEQ ID NO 185
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: wherein n is 5-iodo-2 prime-deoxyuridine

<400> SEQUENCE: 185
nncgttttcg gcgcgcgccg t                                                21

<210> SEQ ID NO 186
<211> LENGTH: 21

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine

<400> SEQUENCE: 186
tncgttttcg gcgcgcgccg t                                            21

<210> SEQ ID NO 187
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 187
ncgtcgtttt acggcgccgt gccgt                                        25

<210> SEQ ID NO 188
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-ethyl-2 prime-deoxyuridine

<400> SEQUENCE: 188
tncgttttac ggcgccgtgc cgt                                          23

<210> SEQ ID NO 189
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: wherein n is 5-iodo-2 prime-deoxyuridine

<400> SEQUENCE: 189
tncgttttac ggcgccgtgc cgt                                          23

<210> SEQ ID NO 190
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(10)
<223> OTHER INFORMATION: wherein residues are deoxyribonucleotides
<220> FEATURE:
<221> NAME/KEY: misc_feature
<222> LOCATION: (1)..(1)
<223> OTHER INFORMATION: wherein n is 5-iodo-2 prime-deoxyuridine
<220> FEATURE:
<221> NAME/KEY: misc_feature
<222> LOCATION: (11)..(17)
```

```
<223> OTHER INFORMATION: wherein residues are ribonucleotides

<400> SEQUENCE: 190
ncgtcgtttt guugugu                                                          17

<210> SEQ ID NO 191
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 191
ncgtcgacga tcggcggccg ccgt                                                  24

<210> SEQ ID NO 192
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 192
ncgtcgacga tcggcggccg ccgt                                                  24

<210> SEQ ID NO 193
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 193
ncgacgtcga tcggcgcgcg ccg                                                   23

<210> SEQ ID NO 194
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: wherein n is 5-ethyl-2 prime-deoxyuridine

<400> SEQUENCE: 194
ncgacgtcga tcggcgcgcg ccg                                                   23

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (3)..(3)
<223> OTHER INFORMATION: wherein n is uridine

<400> SEQUENCE: 195
tgncgttttt ttttttttt                                              20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: wherein n is uridine

<400> SEQUENCE: 196
tgtcgntttt ttttttttt                                              20

<210> SEQ ID NO 197
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 197 tcttttttt cgtttttttt tt                                           22

<210> SEQ ID NO 198
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 198
cggcgccgtg ccg                                                    13
```

CPG OLIGONUCLEOTIDE ANALOGS CONTAINING HYDROPHOBIC T ANALOGS WITH ENHANCED IMMUNOSTIMULATORY ACTIVITY

CROSS REFERENCE TO RELATED APPLICATIONS

This application is a Continuation Application of U.S. application Ser. No. 12/442,295, filed Dec. 7, 2009 (U.S. Pat. 8,580,268), which is the National Stage of International Application No. PCT/IB2007/004389, filed Sep. 25, 2007, which claims the benefit under 35 U.S.C. §119(e) of U.S. Provisional Application Ser. No. 60/847,811, filed Sep. 27, 2006, all of which are incorporated by reference in their entirety.

FIELD OF THE INVENTION

The present invention relates generally to the field of immunology. More specifically the invention relates to therapeutic oligonucleotides with enhanced immunostimulatory capacity.

BACKGROUND OF THE INVENTION

Bacterial DNA has immune stimulatory effects to activate B cells and natural killer cells, but vertebrate DNA does not (Tokunaga, T., at al., 1988. *Jpn. J. Cancer Res.* 79:682-686; Tokumaga, T., et. al., 1984, *JNCI* 72:955-962; Messina, J. P., at al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg at al, 1995 Nature 374:546-549; Krieg, 1999 Biochim. Biophys. Act 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci. USA 96:9305-10).

In early studies, it was thought that the immune stimulatory CpG motif followed the formula purine-puine-CpG-pyrimidine-pyimidine (Krieg et al, 1995 Nature 374:546-549; Pisetaky, 1996 J. Immunol. 156:421-423; Hacker et al., 1998 EMBO J. 17:6230-6240; Lipford at al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmmann et al, 1999 Pro. Natl. Acad. Sci USA 96:9305-10; Liang, 1996 J. Clin. Invest. 98:1119-1129).

Several different classes of CpG nucleic acids has recently been described. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class of CpG nuclei acids activates B cells and NK cells and induces IFN-α; this class has been termed the C-class. The C-class CpG nucleic acids, as first characterized, typically are fully stabilized, include a B class-type sequence and a GC-rich palindrome or near-palindrome. This class has been described in co-pending U.S. provisional patent application 60/313,273, filed Aug. 17, 2001 and U.S. Ser. No. 10/224,523 flied on Aug. 19, 2002 and related PCT Patent Application PCT/US02/26468 published under International Publication Number WO 03/015711.

SUMMARY OF THE INVENTION

The invention relates to an oligonucleotide which comprises one or more modifications that elicits enhanced immunostimulatory capacity. In particular, the invention is based on the finding that specific sub-classes of oligonucleotides having at least one lipophilic substituted nucleotide analog are highly effective in mediating immune response. These oligonucleotides are useful therapeutically and prophylactically for inducing an immune response and for treating disease and disorders such as cancer and viral infections.

In one aspect, the invention is a composition comprising the sequence: $R_1YZR_2$, wherein $R_1$ and $R_2$ represent a lipophilic substituted nucleotide analog (L), a nucleotide, and a linkage, wherein at least one of $R_1$ and $R_2$ is a lipophilic substituted nucleotide analog (L), wherein Y is a pyrimidine nucleotide ad wherein Z is a purine, a pyrimidine, or an abasic residue.

In same embodiments, L comprises a 5- or 6-membered ring nucleobase analog.

In other embodiments of the aspect of the invention, L is a group of formula I.

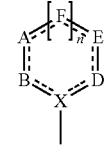

Formula I having the following elements: A, B, X, D, E, and F are C (carbon) or N (nitrogen) optionally bearing hydrogen or a substituent; n is 0 or 1; the dotted lines indicate optional double bonds; wherein at least one substituent is not chosen from the group consisting of oxo, thio, hydroxy, mercapto, imino, amino, methyl and hydrogen, and that the total of A, B, X, D, E and F atoms is not more than 3 nitrogens (N). In some cases, n is 1, and in other cases n is 0. In sane embodiments, all atoms A, B, X, D, E, F are carbon (C). In some embodiments, one, two or three of the atoms A, B, X, D, E, F are nitrogen (N). According to some embodiments, at leat one of the atoms A, B, X, D, B, F is substituted by one of the following: F, Cl, Br, I, alkyl, alkenyl, alkinyl, halogenated alkyl, halogenated alkenyl, cycloalkyl, O-alkyl, O-alkenyl, —NH-alkyl, —N(alkyl)$_2$; —S-alkyl, —SO-alkyl, —SO$_2$-alkyl, nitro, cyano, carboxylester, phenyl, thiophenyl, benzyl, oxo, thio, hydroxy, mercapto, and imino, wherein at least one substituent is not oxo, thio, hydroxy, mercapto, imino, amino or methyl. According to yet other embodiments, one of the two atoms A or B is substituted by one of the following: F, Cl, Br, I, $C_2$-$C_6$-alkyl, alkenyl, alkinyl, halogenated alkyl, halogenated alkanyl, cycloalkyl, O-alkyl, O-alkenyl, —N-alkyl, —N(alkyl)$_2$; —S-alkyl, —SO-alkyl, —SO$_2$-alkyl, nitro, cyano, carboxylester, phenyl, thiophenyl, benzyl, or methyl, provided that if methyl then A, B, X, D, E, and F are all C.

In some embodiments formula I comprises a substituted pyrimidine, uracil, toluene, imidazole or pyrazole or triazole. According to other embodiments, formula I is selected from the following: 5-cloro-uracil, 5-bromo-uracil, 5-iodo-uracil, 5-ethyl-uracil, 5-propyl-uracil, S-propinyl-uracil, (B)-5-(2-bromovinyl)-uracil, and 2.4-difluoro-toluene. According to one embodiment of the invention, formula I is fused with a 3-to-6-membered aromatic or aliphatic ring system. According to other embodiments, formula I is linked to a 5- to 6-membered sugar moiety, including a pentose or hexose. In some cases, the pentose is a furanose and hexose is a pyranose, which can optionally be substituted by F, amino, alkoxy, alkoxy-ethoxy, amonipropyl, alkenyl, alkinyl, or a O2,C4-alkylene bridge In other cases, the furanose is ribose or deoxyribose.

According to some embodiments of the invention, $R_1$ and $R_2$ are both L. In some embodiments, $R_1$ is L and $R_2$ is a nucleotide. Alternatively, in some cases $R_1$ is a L and $R_2$ is a linkage, such that the oligonucleotide comprises a structure 5' $R_1$CG 3'. Other embodiments include oligonucleotide wherein $R_1$ is L and $R_2$ is a linkage, and wherein a $R_3$ is 5' to $R_1$YZ, such that the oligonucleotide comprises a structure 5' $R_3R_1$YZ 3'. In some embodiments, $R_1$ is L and $R_2$ is a linkage, and wherein a second $R_1$ is 5' to $R_1$YZ spaced by one nucleotide N, such that the oligonucleotide comprises a structure 5' $R_1NR_1$YZ 3'. In some cases, the oligonucleotide may include two 5' $R_1NR_1$YZ 3' motifs.

According to some embodiments, The oligonucleotide includes Y that is one of the following pyrimidines: cytosine. S-methyl-cytosine, 5-hydroxy-cytosine, 5-hydroxymethyl-cytosine, 5-halogeno-cytosine, 2-thio-cytosine, 4-thio-cytosine, N3-methyl-cytosine, N4-alkyl-cytosine or a 6-substituted cytosine.

According to some embodiments, the oligonucleotide includes Z that is a purine nucleotide including guanine, 7-deaza-guanine, hypoxanthine, 7-deaza-hypoxanthine, 2-amino-purine, 4-thio-purine, 2.6-diamino-purine, 8-oxo-7.8-dihydroguanine, 7-thia-8-oxo-7.8-dihydroguanine, 7-allyl-8-oxo-7.8-dihydroguanine, 7-deaza-aza-8-aza-anine, 8-aza-guanine, N1-methyl-guanine or purine. In other embodiments, Z is a pyrimidine nucleotide, including T.

According to some embodiments of the invention, $R_2$ is L and $R_1$ is a nucleotide.

According to some embodiments, the oligonucleotide is between 3-100 nucleotides in length; for example, the oligonucleotide is 3-6 nucleotides in length, 3-100 nucleotides in length, or 7-100 nucleotides in length. In some circumstances, the oligonucleotide is T-rich, such that at least 80% of the nucleotides are T.

The invention includes embodiments comprising at least one palindromic sequence. For example, in some cases, the oligonucleotide includes two palindromic sequences.

According to the invention, some embodiments include one to four unmethylated CG dinucleotides. In some embodiments, the oligonucleotide may include at least one (G)m sequence, wherein m is 4 to 10. In some cases, at least one but up to all CG dinucleotides are unmethylated. According to some embodiments, the oligonucleotide may additionally comprise a non-nucleotidic modification. The non-nucleotidic modifications include but are not limited to: $C_6$-$C_{48}$-polyethyleneglycol, $C_3$-$C_{20}$-alkane-diol, $C_3$-$C_{18}$-alkylamino linker, $C_3$-$C_{18}$-alkylthiol linker, cholesterol, bile acid, saturated or unsaturated fatty acid, folate, a hexadecyl-glycerol or dihexadecyl-glycerol group, an octadecyl-glycerol or dioctadecyl-glycerol group, a vitamin B group. In other embodiments, the oligonucleotide of the invention further comprises a non-nucleotidic brancher moiety or a nucleotidic brancher moiety. In some embodiments, the oligonucleotide includes a brancher moiety, wherein the oligonucleotides has at least two 5'-ends.

According to the invention, same embodiments include at least two nucleotides of the oligonucleotide have a stabilized linkage, including: phosphorothioate, phosphorodithioate, methylphosphonate, methylphosphonothioate phosphoramidate, or a dephospho linkage, either as enantiomeric mixture or as enantiomeric pure S- or R-configuration.

Yet in some embodiments, the YZ of $R_1YZR_2$ has a phosphodiester linkage or a phosphorothioate linkage. In some cases, the $R_1Y$ and or the $ZR_2$ of $R_1YZR_3$ has a phosphorothioate linkage. In some embodiments, all other nucleotides have a phosphorthioate linkage.

According to some embodiments of the invention, the oligonucleotide is free of a microcarrier, including a lipid carrier.

According to the invention, the oligonucleotides may be an A class olignucleotide, a B class oligonucleotide, a C class oligonucleotide, a P class oligonucleotide or a T class oligonucleotide. For the B class oligonucleotide of the invention, some embodiments include the sequence 5' $TCN_1TX_1X_2CGX_3X_4$ 3', wherein $X_1$ is G or A; X is T, G, or A; $X_3$ is T or C ad X is T or C; and N is any nucleotide, and $N_1$ and $N_2$ are nucleic acid sequences of about 0-25 N's each.

According to some embodiments of the invention, the oligonucleotide comprises at least one 3'-3' linkage and or at least one 5'-5' linkage.

In another aspect the invention is a composition of the oligonucleotides described herein in combination with an antigen or other therapeutic compound, such as an anti-microbial agent. The anti-microbial agent may be, for instance, an anti-viral agent, an anti-parasitic agent, an anti-bacterial agent or an anti-fungal agent.

A composition of a sustained release device including the oligonucleotides described herein is provided according to another aspect of the invention.

The composition may optionally include a pharmaceutical carrier and/or be formulated in a delivery device. In some embodiments the delivery device is selected from the group consisting of cationic lipids, cell permeating proteins, and sustained release devices. In one embodiment the sustained release device is a biodegradable polymer or a microparticle.

According to another aspect of the invention a method of stimulating an immune response is provided. The method involves administering an oligonucleotide to a subject in an amount effective to induce an immune response in the subject. Preferably the oligonucleotide is administered orally, locally, in a sustained release device, mucosally, systemically, parenterally, or intramuscularly. When the oligonucleotide is administered to the mucosal surface it may be delivered in an amount effective for inducing a mucosal immune response or a systemic immune response. In preferred embodiments the mucosal surface is selected from the group consisting of an oral, nasal, rectal, vaginal, and ocular surface.

In some embodiments the method includes exposing the subject to an antigen wherein the immune response is an antigen-specific immune response. In some embodiments the antigen is selected from the group consisting of a tumor antigen, a viral antigen, a bacterial antigen, a parasitic antigen and a peptide antigen.

The oligonucleotides are useful for treating cancer in a subject having cancer or in a subject at risk of developing a cancer (e.g., reducing a risk of developing cancer). The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

The oligonucleotides may also be used for increasing the responsiveness of a cancer cell to a cancer therapy (e.g., an anti-cancer therapy), optionally when the CpG immunostimulatory oligonucleotide is administered in conjunction with an anti-cancer therapy. The anti-cancer therapy may be a chemotherapy, a vaccine (e.g., an in vitro primed dendritic cell vaccine or a cancer antigen vaccine) or an antibody based therapy. This latter therapy may also involve administering an antibody specific for a cell surface antigen of; for example, a cancer cell, wherein the immune response results in antibody dependent cellular cytotoxicity (ADCC). In one embodiment, the antibody may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260. ANA Ab, SMART 1D10 Ab, SMART ABL 364 Ab and ImmuRAIT-CEA.

Thus, according to some aspects of the invention, a subject having cancer or at risk of having a cancer is administered an oligonucleotide and an anti-cancer therapy. In some embodiments, the anti-cancer therapy is selected from the group consisting of a chemotherapeutic agent, an immunotherapeutic agent and a cancer vaccine.

The invention in other aspects relates to methods for preventing disease in a subject. The method involves administering to the subject an oligonucleotide on a regular basis to promote immune system responsiveness to prevent disease in the subject. Examples of diseases or conditions sought to be prevented using the prophylactic methods of the invention include microbial infections (e.g., sexually transmitted disease) and anaphylactic shock from food allergies.

In other aspects, the invention is a method for inducing an innate immune response by administering to the subject an oligonucleotide in an amount effective for activating an innate immune response.

According to another aspect of the invention a method for treating a viral or retroviral infection is provided. The method involves administering to a subject having or at risk of having a viral or retroviral infection, an effective amount for treating the viral or retroviral infection of any of the compositions of the invention. In some embodiments the virus is caused by a hepatitis virus e.g., hepatitis B, hepatitis C, HIV, herpes virus, or papillomavirus.

A method for treating a bacterial infection is provided according to another aspect of the invention. The method involves administering to a subject having or at risk of having a bacterial infection, an effective amount for treating the bacterial infection of any of the compositions of the invention. In one embodiment the bacterial infection is due to an intracellular bacteria.

In another aspect the invention is a method for treating a parasite infection by administering to a subject having or at risk of having a parasite infection, an effective amount for treating the parasite infection of any of the composition of the invention. In one embodiment the parasite infection is due to an intracellular parasite. In another embodiment the parasite infection is due to a non-helminthic parasite.

In some embodiments the subject is a human and in other embodiments the subject is a non-human vertebrate selected from the group consisting of a dog, cat, horse, cow, pig, turkey, goat, fish, monkey, chicken, rat, mouse and sheep.

In mother aspect, the invention relates to a method for treating autoimmune disease by administering to a subject having or at risk of having an autoimmune disease an effective amount for treating or preventing the autoimmune disease of any of the compositions of the invention.

The invention in some aspects is a method for treating airway remodeling, asthma or allergy comprising: administering to a subject my of the compositions of the invention, in an effective amount to treat airway remodeling asthma or allergy in the subject. In one embodiment the subject has asthma, chronic obstructive pulmonary disease, or is a smoker. In other embodiments the subject is free of symptoms of asthma.

Use of an oligonucleotide of the invention for stimulating an immune response is also provided as an aspect of the invention.

A method for manufacturing a medicament of an oligonucleotide of the invention for stimulating an immune response is also provided.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

FIG. 1a shows a section of a CpG hexamer motif (GTCGTT). FIG. 1b shows the incorporated hydrophobic shape analogs of 2'-deoxythymidine: 2,4-Difluorotoluene (FF), 5-bromouridine (BU) and 5-iodouridine (JU).

FIG. 5 is two graphs demonstrating the results of a luciferase may and a PBMC may with modified B class ODN. The relative activity of an ODN with 5-Ethyl-2'-deoxyuridine (EU) (SEQ ID NO:42), 2'-deoxyuridine (U) (SEQ ID NO:16), 5-iodo-2'-deoxyuridine (JU) (SEQ ID NO:13), 5-bromo-2'-deoxyuridine (BU) (SEQ ID NO:10), and 5-Chloro-2'-deoxyuridine (CU) (SEQ ID NO:41) was compared to that of the parent sequence (SEQ ID NO:1).

FIG. 8 is two graphs demonstrating the results of a luciferase assay and a PBMC assay with modified A class ODN. The activity of JU-modified SEQ ID NO:35-37 was compared to that of the unmodified parent sequence (SEQ ID NO:43) and to unmodified B-class ODN SEQ ID NO: 1.

FIGS. 13a-d show TNF-alpha, IL-6, IL-10, and IL-12 concentration, respectively. The x-axes are ODN concentration in g/ml and the y-axes are cytokine concentration in pg/ml.

FIG. 15 is two graphs showing in vivo cytokine production as measured by EISA. BALB/c mice (5 per group) were injected SC with 10, 50 or 100 μg of ODN. Control group received 100 μl of PBS alone. Animals were bled by cardiac puncture at 1 hour (for TNF-alpha) or 3 hour (for IP-10) post injection and plasma assayed for TNF-alpha and IP-10 by ELISA. The activities of a JU-modified B-class ODN (SEQ ID NO:13) and an unmodified B-class ODN (SEQ ID NO:37) were compared.

FIG. 24a shows the activity of SEQ ID NO:58-61 compared to that of a B-class positive control (SEQ ID NO:55) and an unmodified P-class ODN (SEQ ID NO:56). FIG. 24b shows the activity of SEQ ID NO:62-63 compared to that of the same positive and negative controls. hTLR9-LUC-293 cells were incubated with indicated amounts of nucleic acids and NF-κB activation was determined 16 h later by measuring luciferase activity. The x-axis is log of ODN concentration in μM and the y-axis is the relative stimulation index.

FIG. 26 is two graphs showing induction of IFN-α by P-class ODN with a lipophilic substituted nucleotide analog (SEQ ID NO:58-63). FIG. 26a shows the activity of SEQ ID NO:58-61 compared to that of a B-class positive control (SEQ ID NO:55) and an unmodified P-class ODN (SEQ ID NO:56). FIG. 26b shows the activity of SEQ ID NO:62-63 compared to that of the same positive and negative controls. Human PBMC were incubated with the indicated ODN for 48 hours. IFN-α was then determined in the cell culture supernatants by ELISA. The x-axes are ODN concentration in μM and the y-axes are IFN-α concentration in pg/ml.

FIG. 28 is two graphs showing IL-6 induction by P-class ODN with a lipophilic substituted nucleotide analog (SEQ ID NO:58, 60-62, FIG. 28a) (SEQ ID NO:64 and 67, FIG. 28b). The activity was compared to that of an unmodified B-class ODN (SEQ ID NO:55), and unmodified C-class ODN (SEQ ID NO:54), a negative control ODN (SEQ ID NO:53), and an unmodified P-class ODN (SEQ ID NO:56). PBMC from three donors were incubated with the ODN for 24 hours and the supernatants were analyzed by luminex. Shown is the mean+/−SEM. The x-axes are ODN concentration in μM and the y-axes are IL-6 concentration in pg/ml.

FIG. 31 is two graphs showing the effect of ODN on tumor volume in the mouse SAIN tumor model. Female A/J mice(10 per group) were injected SC with $5\times10^5$ SaI/N tumor cells on day 0. Mice were treated with 35 μg (FIG. 31a) or 100 μg (FIG. 31b) P-class ODN with a lipophilic substituted nucleotide analog (SEQ ID NO:60, 64, and 67), an unmodified C-class ODN, an unmodified B-class ODN (SEQ ID NO:55), or PBS alone given SC once weekly starting on day 8 post tumor induction. Animals were monitored for survival and tumor volume. Tumor size (the length and the width) was measured using a digital vernier caliper. Tumor volume was calculated by using the formula: Tumor volume=(0.4)(ab2), where a=large diameter and b=smaller diameter. The x-axes show days post tumor induction and the y-axa show tumor volume in $mm^3$.

DETAILED DESCRIPTION

Figure 1:
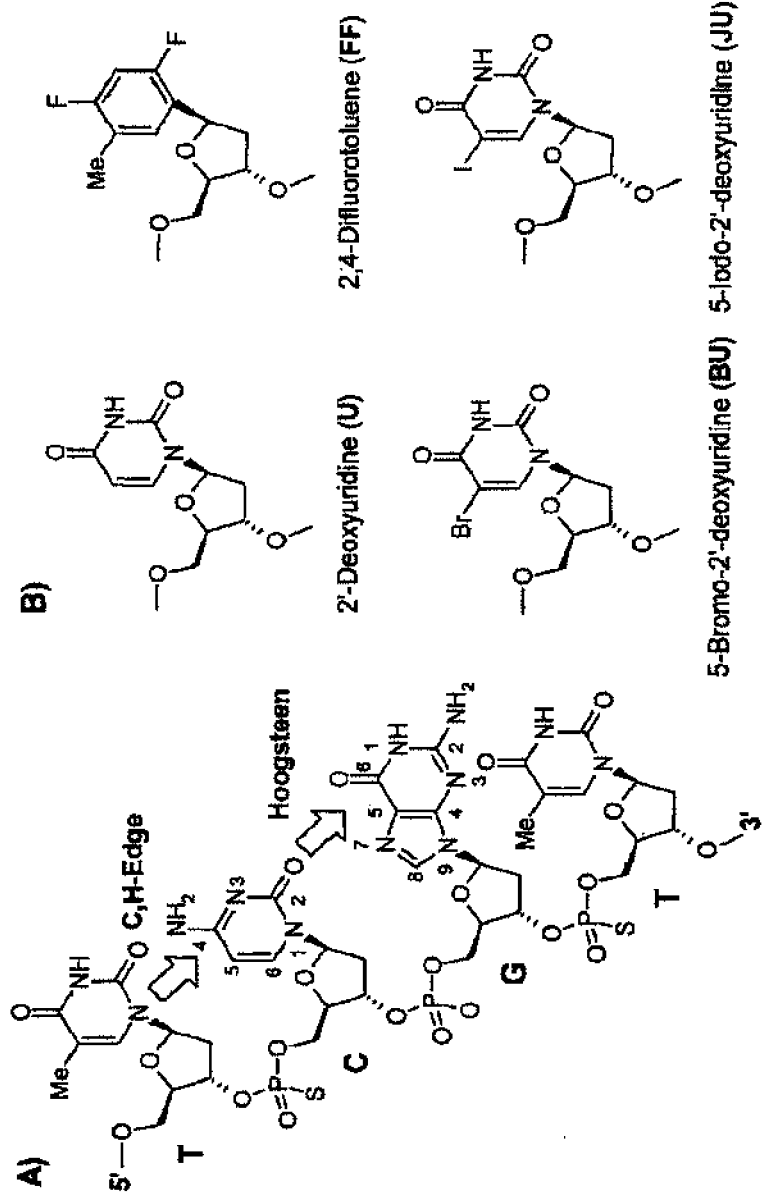
FIG. 1 is two drawings illustrating the structure of the modified bases of the invention.

The invention is based in part on CpG oligonucleotides that show enhanced immunostimulatory capacity. CpG oligonucleotides are known to stimulate the immune system, for example through interaction with toll-like receptor 9 (TLR9). Stimulation of TLR9 has many effects including stimulation of a Th1 biased immune response, NK cell activation and B cell activation. The invention is related in some aspects to the identification of immunostimulatory oligonucleotides with altered structure that affects their interaction with TLR9. It was discovered by the inventors that oligonucleotides with lipophilic substituted nucleotide analogs outside the CpG motif have enhanced ability to stimulate interferon-α (IFN-α) production and induce TLR9 activation. This effect has been observed in all classes of immunostimulatory oligonucleotides tested. These modified oligonucleotides with enhanced stimulatory capacity have been termed B class oligonucleotide.

The E class modified oligonucleotides of the instant invention have in some instances enhanced capacity for inducing an immune response. An induction of an immune response refers to any increase in number or activity of an immune cell, or am increase in expression or absolute levels of an immune factor, such as a cytokine. Immune cells include, but are not limited to, NK cells, CD4+ T lymphocytes, CD8+ T lymphocytes, B cells, dendritic cells, macrophage and other antigen-presenting cells. Cytokines include, but are not limited to, interleukins, TNF-α, IFN-α,β and γ, Flt-ligand, and costimulatory molecules.

It is known that oligonucleotides containing unmethylated CpG motifs are able to stimulate immune responses through the Toll-like receptor 9 (TLR9) pathway. The induction of many cytokines correlates with TLR9 activation. Thus induction increases as TLR9 stimulation increases. However there is generally inverse correlation between TLR9 and IFN-α induction for CpG ODN. It was discovered that some of the modifications of the invention can produce a modified signaling pattern such that a more direct correlation, rather than an inverse correlation between TLR9 activation and IFN-α is observed.

The inventors set out to investigate the impact of the lipophilic residues in region surrounding the CpG motif. As described in the examples below several different types of lipophilic substituted nucleotide analogs, such as 2,4-difluorotoluene, 5-bromouracil and 5-iodouracil were incorporated into a CpG oligonucleotide on either the 5' or 3' side of the CpG motif. Unexpectedly, incorporation of these lipophilic substituted nucleotide analogs led to a unusually strong increase in hTLR9 activity a well as IFN-α induction in human PBMC's. Substitution with a non-lipophilic nucleotide such as a uracil residue (which is structurally similar to a thymine but lacking a methyl group) produced a strong decrease in hTLR9 stimulation. In the oligonucleotide tested, the increase in TLR9 stimulation appeared to be better if the lipophilic substituted nucleotide analog is positioned 5' to the CpG motif than when it was positioned 3' to the motif. Double substitution (i.e. a 5' and 3' lipophilic substituted nucleotide analog substitution) resulted in most potent stimulation of those tested. In contrast, substitution of guanine or cytosine by 2,4-difluorotoluene at the CpG motif led in both cases to a strong decrease of the TLR9 stimulation index.

The lipophilic substituted nucleotide analogs modification resulted in a strong enhancement of IFN-α induction. Especially, for the 5-bromouracil and 5-iodouracil modified ODN, there appeared to be a good correlation between TLR9 stimulation and IFN-α induction. As mentioned above, this observation was unexpected, since (i) the parent molecule 21317 is virtually inactive in inducing IFN-α and (ii) there is usually a inverse correlation between TLR9 and IFN-α induction for CpG ODN which do not contain these modifications.

In some aspects of the invention the oligomicleotide has the sequence $R_1YZR_2$. The oligonucleotide may be include one or more such motifs. $R_1$ and $R_2$ are independently any one of lipophilic substituted nucleotide analog (L), a nucleotide, or a linkage. It is preferred, however, that at least one of $R_1$ ad $R_2$ is a lipophilic substituted nucleotide analog (L). In some instances $R_1$ and $R_3$ are both L. As shown in the examples section below oligonucleotides having an L both 5' ad 3' to the CpG motif were particularly stimulatory. However sometime only one R is a L. For instance $R_1$ may be L and $R_2$ is a nucleotide or vice versa. Alternatively $R_1$ may be a L and $R_2$ may be a linkage, such that the oligonucleotide comprise a structure 5' $R_1CG$ 3'.

In some instances the oligonucleotide has the sequence $R_1N_1YZN_2R_2$ wherein $N_1$ and $N_2$ are nucleotides of 0-3 nucleotides in length. Other possible variations include structures such as 5' $R_1N_1R_1YZN_2$ 3', 5'$R_3R_1YZ$ 3 and $R_1ZN_2R_2$.

Y is a pyrimidine nucleotide. Z is a purine, a pyrimidine, or an abasic residue. In some embodiments Z is preferably a purine.

L is a lipophilic substituted nucleotide analog which may be, for instance, a 5- or 6-membered ring nucleobase analog. An example of a 5- or 6-membered ring nucleobase analog is shown in the following group of formula I.

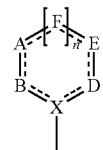

Formula I

A, B, X, D, F, and F are independently any one of C (carbon) or N (nitrogen) optionally bearing hydrogen or a substituent such as for instance, but not limited to, F, Cl, Br, I, alkyl, alkenyl, alkinyl, halogenated alkyl, halogenated alkenyl, cycloalkyl, O-alkyl, O-alkenyl, —NH-alkyl, —N(alkyl)$_2$; —S-alkyl, —SO-alkyl, —SO$_2$-alkyl, nitro, cyano, carboxylester, phenyl, thiophenyl, benzyl, oxo, thio, hydroxy, mercapto, and imino. In some instances, at least one substituent is not oxo, thio, hydroxy, mercapto, imino, amino or methyl. n is 0 or 1. The dotted lines indicate optional double bonds. However, at least one substituent is not chosen from the group consisting of oxo, thio, hydroxy, mercapto, imino, amino, methyl and hydrogen. Additionally the total of A, B, X, D, B and F atoms is not more than 3 nitrogens (N). In some embodiments all atoms A, B, X, D, B, F are carbon (C). Alternatively, at least one, two, or three of the atoms A, B, X, D, E, F is nitrogen (N).

The compound of formula may be, for example, many of the following lipophilic substituted nucleotide analogs: a substituted pyrimidine a substituted uracil, a substituted toluene, a substituted imidazole or pyrazole, a substituted triazole, 5-chloro-uracil, 5-bromo-uracil, 5-iodo-uracil, 5-ethyl-uracil, 5-propyl-uracil, 5-propinyl-uracil, (E)-5-(2-bromovinyl)-uracil, or 2,4-difluoro-toluene.

The lipophilic substituted nucleotide analog may be separate or it may be fused with another compound. For instance is may be fused to a 3-to-6-membered aromatic or aliphatic ring system. It may also be linked to a 5- to 6-membered sugar moiety such as for instance a pentose or hexose. An example of a pentose is a furanose such as a ribose or deoxyribose and an example of a hexose is a pyranose. The pentose or hexose can optionally be substituted by F, amino, alkoxy, alkoxyethoxy, amonipropyl, alkenyl, alkinyl, or a O2,C4-alkylene bridge.

The oligonucleotide may also include a non-nucleotidic modification such as a $C_6$-$C_{48}$-polyethyleneglycol, $C_3$-$C_{20}$-alkane-diol, $C_3$-$C_{18}$-alkylamino linker, $C_3$-$C_{18}$-alkylthiol linker, cholesterol, bile acid, saturated or unsaturated fatty acid, folate, hexadecyl-glycerol, dihexadecyl-glycerol group, an octadecyl-glycerol or dioctadecyl-glycerol group or a vitamin E group.

The lipophilic substituted nucleotide analogs can be incorporated into any immunostimulatory oligonucleotide. In some embodiments of the invention the immunostimulatory oligonucleotides include immunostimulatory motifs which are "CpG dinucleotides". A CpG dinucleotide can be methylated or unmethylated. An immunostimulatory nucleic acid containing at least one unmethylated CpG dinucleotide is a nucleic acid molecule which contains an unmethylated cytosine-guanine dinucleotide sequence (i.e., an unmethylated 5' cytidine followed by 3' guanosine and linked by a phosphate bond) and which activates the immune system; such an immunostimulatory nucleic acid is a CpG nucleic acid. CpG nucleic acids have been described in a number of issued patents, published patent applications, and other publications, including U.S. Pat. Nos. 6,194,388; 6,207,646; 6,214,806; 6,218,371; 6,239,116; and 6,339,068. An immunostimulatory nucleic acid containing at least one methylated CpG dinucleotide is a nucleic acid which contains a methylated cytosine-guanine dinucleotide sequence (i.e., a methylated 5' cytidine followed by a 3' guanosine and linked by a phosphate bond) and which activates the immune system. In other embodiments the immunostimulatory oligonucleotides are free of CpG dinucleotides. These oligonucleotides which we free of CpG dinucleotides are referred to as non-CpG oligonucleotides, and they have non-CpG immunostimulatory motifs. Preferably these are T-rich ODN, such as ODN having at to least 80% T.

The E class ODNs of the invention may include motifs and properties of other CpG ODN classes such as A class, B call, C class, T class and P class as long as they include lipophilic substituted nucleotide analogs 5' and/or 3' of a YGZ motif.

"A class" CpG immunostimulatory nucleic acids have been described in U.S. Non-Provisional patent application Ser. No. 09/672,126 and published PCT application PCT/US00/26527 (WO 01/22990), both filed on Sep. 27, 2000. These nucleic acids are characterized by the ability to induce high levels of interferon-alpha while having minimal effects on B cell activation. The A class CpG immunostimulatory nucleic acid do not necessarily contain a hexamer palindrome GACGTC, AGCGCT, or AACGTT described by Yamamoto and colleagues. Yamanoto S at al. *J Immunol* 148:4072-6 (1992).

Exemplary sequences of A class immunostimulatory nucleic acids are described in U.S. Non-Provisional patent application Ser. No. 09/672,126 and published PCT application PCT/US00/26527 (WO 01/22990), both filed on Sep. 27, 2000.

"B class" ODN are potent at activating B cells but are relatively weak in inducing IFN-α and NK cell activation. The B class CpG nucleic acids typically are fully stabilized and include ma unmethylated CpG dinucleotide within certain preferred base contexts. See, e.g., U.S. Pat. Nos. 6,194, 388; 6,207,646; 6,214,806; 6,218,371; 6,239,116; and 6,339, 068. Another class is potent for inducing IFN-α and NK cell activation but is relatively weak at stimulating B cells; this class has been termed the "A class". The A class CpG nucleic acids typically have stabilized poly-G sequences at 5' and 3' ends and a palindromic phosphodiester CpG dinucleotide-containing sequence of at least 6 nucleotides. See, for example, published patent application PCT/US00/26527

Yet another class of CpG nucleic acids activates B cells and NK cells and induces IFN-α this class has been trmed the C-class. The "C class" immunostimulatory nucleic acids contain at least two distinct motifs have unique and desirable stimulatory effects on cells of the immune system. Some of these ODN have both a traditional "stimulatory" CpG sequence and a "GC-rich" or "B-cell naturalizing" motif. These combination motif nucleic acids have immune stimulating effects that fall somewhere between those effects associated with traditional "class B" CpG ODN, which are strong inducers of B cell activation and dendritic cell (DC) activation, and those effects associated with a more to recently described class of immune stimulatory nucleic acids ("class A" CpG ODN) which are strong inducers of IFN-α and natural killer (NK) cell activation but relatively poor inducers of B-cell and DC activation. Krieg A M et al. (1995) *Nature* 374:546-9; Ballas Z K et al. (1996) *J Immunol* 157:1840-5; Yamamoto S et al. (1992) *J Immunol* 148:4072-6. While preferred class B CpG ODN often have phosphorothioate backbones and preferred class A CpG ODN have mixed or chimeric backbones, the C class of combination motif immune stimulatory nucleic acids may have either stabilized, e.g., phosphorthioate, chimeric, or phosphodiester backbones, and in some preferred embodiments, they have semi-soft backbones. This class has been described in U.S. patent application Ser. No. 10/224,523 filed on Aug. 19, 2002, the entire contents of which is incorporated herein by reference.

The "P class" immunostimulatory oligonucleotides have several domains, including a 5'TLR activation domain, 2 duplex forming regions and an optional spacer and 3' tail. This class of oligonucleotides has the ability in some instances to induce much higher levels of IPN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously so described classes of CpG oligonucleotides. Cross-linking of TLR9 receptors may induce activation of stronger IFN-α secretion through the type I IFNR feedback loop in plasmacytoid dendritic cells. P class oligonucleotide are described at least in U.S. application Ser. No. 11/706,561.

The "T class" oligonucleotides induce secretion of lower levels of IFN-alpha when not modified a in the ODNs of the invention and IFN-related cytokines and chemokines than B class or C class oligonucleotides, while retaining the ability to induce levels of IL-10 similar to B class oligonucleotides. T class oligonucleotides are described at least in U.S. patent application Ser. No. 11/099,683, the entire contents of which are hereby incorporated by reference.

In one embodiment the immunostimulatory ODN of the invention is advantageously combined with a cationic lipid. In one embodiment the cationic lipid is DOTAP (N-[1-(2,3-dioleoyloxy)propy-1]-N,N,N-trimethylammonium methylsulfate). Other agents with similar properties including trafficking to the endosomal compartment can be used in place of or in addition to DOTAP. Other lipid formulations include, for example, as EFFECTNE™ (a non-liposomal lipid with a special DNA condensing enhancer) and SUPERFECT™ (a novel acting dendrimeric technology). Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

In other embodiments the immunostimulatory ODN are not formulated in cationic liposomes. Tue to the lipophilic nature of the modified analogs within the ODN even short ODN such as 3 nucleotides in length may not require formulation to efficiently function in vivo.

In one embodiment the immunostimulatory ODN of the invention are in the form of covalently closed, dumbbell-shaped molecules with both primary and secondary structure. In one embodiment such cyclic oligoribonucleotides include two single-stranded loops connected by an intervening double-stranded segment. In one embodiment at least one single-stranded loop includes an immunostimulatory DNA motif of the invention. Other covalently closed, dumbbell-shaped molecules of the invention include chimeric DNA-RNA molecules in which, for example, the double-stranded segment is at least partially DNA (e.g., either homodimeric dsDNA or heterodimeric DNA:RNA) and at least one single-stranded loop includes an immunostimulatory DNA motif of the invention. Alternatively, the double stranded segment of the chimeric molecule is DNA.

In certain embodiments the immunostimulatory ODN is isolated. An isolated molecule is a molecule that is substantially pure and is free of other substances with which it is ordinarily found in nature or in in vivo systems to an extent practical and appropriate for its intended use. In particular, the immunostimulatory ODN are sufficiently pure and are sufficiently free from other biological constituents of cells so as to be useful in, for example, producing pharmaceutical preparations. Because an isolated immunostimulatory ODN of the invention may be admixed with a pharmaceutically acceptable carrier in a pharmaceutical preparation, the immunostimulatory ODN may comprise only a small percentage by weight of the preparation. The immunostimulatory ODN is nonetheless substantially pure in that it has been substantially separated from the substances with which it may be associated in living systems.

The immunostimulatory nucleic acid molecules may have a chimeric backbone. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vio degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation: peptide, alkyl, dephospho, and others as described above.

Modified backbone such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann B et al. (1990) *Chem Rev* 90:544; Goodchild J (1990) *Bioconjugate Chem* 1:165. Methods for preparing chimeric oligonucleotides are also known. For instance patents issued to Uhlmann et al have described such techniques.

Mixed backbone modified ODN may be synthesized using a commercially available DNA synthesizer and standard phosphoramidite chemistry. (F. B. Eckstein, "Oligonucleotides and Analogs—A Practical Approach" IRL Press, Oxford, UK, 1991, and M. D. Matteuci and M. H. Caruthers, *Tetrahedron Lett.* 21, 719 (1980)) After coupling, PS linkages are introduced by sulfurization using the Beaucage reagent (R. P. Iyer, W. Egan, J. B. Regan and S. L. Beuacage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofuran (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide the intermediate phosphorous-III is oxidized by treatment with a solution of iodine in water/pyridine. After cleavage from the solid support and final deprotection by treatment with concentrated ammonia (15 hrs at 50° C.), the ODN are analyzed by HPLC on a Gen-Pak Fax column (Millipore-Waters) using a NaCl-gradient (e.g. buffer A: 10 mM $NaH_2PO_4$ in acetonitril-water=1:4/v:v pH 6.8; buffer B: 10 mM $NaH_2PO_4$, 1.5 M NaCl in acetonitril-water=1:4/v:v; 5 to 60% B in 30 minute at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The nucleic acids of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In some embodiments the oligonucleotides may be soft or semi-soft oligonucleotides. A soft oligonucleotide is an immunostimulatory oligonucleotide having a partially stabilized backbone, in which phosphodiester or phosphodiester-like internucleotide linkages occur only within and immediately adjacent to at least one is internal pyrimidine-purine dinucleotide (YZ). Preferably YZ is YG, a pyrimidine-guanosine (YG) dinucleotide. The at least one internal YZ dinucleotide itself has a phosphodiester or phosphodiester-like internucleotide linkage A phosphodiester or phosphodiester-like internucleotide linkage occurring immediately adjacent to the at least one internal YZ dinucleotide can be 5', 3', or both 5' and 3' to the at least one internal YZ dinucleotide.

In particular, phosphodiester or phosphodiester-like internucleotide linkages involve "internal dinucleotides". An internal dinucleotide in general shall mea any pair of adjacent nucleotides connected by an internucleotide linkage, in which neither nucleotide in the pair of nucleotides is a terminal nucleotide, i.e., neither nucleotide in the pair of nucleotides is a nucleotide defining the 5' or 3' end of the oligonucleotide. Thus a linear oligonucleotide that is n nucleotides long has a total of n-1 dinucleotides and only n-3 internal dinucleotides. Each internucleotide linkage in an internal dinucleotide is an internal internucleotide linkage. Thus a linear oligonucleotide that is n nucleotides long has a total of n-1 Internucleotide linkages and only n-3 internal internucleotide linkages. The strategically placed phosphodiester or phosphodiester-like internucleotide linkages, therefore, refer to phosphodiester or phosphodiester-like internucleotide linkages positioned between any pair of nucleotides in the nucleic acid sequence. In some embodiments the phosphodiester or phosphodiester-like internucleotide linkages are not positioned between either pair of nucleotides closest to the 5' or 3' end.

Preferably a phosphodiester or phosphodiester-like internucleotide linkage occurring immediately adjacent to the at least one internal YZ dinucleotide is itself an internal internucleotide linkage. Thus for a sequence $N_1YZN_2$, wherein $N_1$ and $N_2$ are each, independent of the other, any single nucleotide, the YZ dinucleotide has a phosphodiester or phosphodiester-like internucleotide linkage, and in addition (a) $N_1$ and Y are linked by a phosphodiester or phosphodiester-like internucleotide linkage when $N_1$ is an internal nucleotide, (b) Z and $N_2$ are linked by a phosphodiester or phosphodiester-like internucleotide linkage when $N_2$ is an internal nucleotide, or (c) $N_1$ and Y are linked by a phosphodiester or phosphodiester-like internucleotide linkage when $N_1$ is an internal nucleotide and Z and $N_2$ are linked by a phosphodiester or phosphodiester-like internucleotide linkage when $N_2$ is an internal nucleotide.

In the oligonucleotide of the invention at least one YZ of $R_1YZR_2$ may have a phosphodiester linkage. Alternatively the YZ of $R_1YZR_2$ may have a phosphorothioate linkage. In some embodiments the $R_1Y$ and or $ZR_2$ of $R_1YZR_2$ have a phosphorothioate linkage.

Soft oligonucleotides according to the instant invention are believed to be relatively susceptible to nuclease cleavage compared to completely stabilized oligonucleotides. Without meaning to be bound to a particular theory or mechanism, it is believed that soft oligonucleotides of the invention are cleavable to fragments with reduced or no immunostimulatory activity relative to full-length soft olignucleotide. Incorporation of at least one nuclease-sensitive internucleotide linkage, particularly near the middle of the oligonucleotide, is believed to provide an "off switch" which alters the pharmacokinetics of the oligonucleotide so as to reduce the duration of maximal immunostimulatory activity of the oligonucleotide. This can be of particular value in tissues and in clinical applications in which it is desirable to avoid injury related to chronic local inflammation or immunostimulation, e.g., the kidney.

A semi-soft oligonucleotide is an immunostimulatory oligonucleotide having a partially stabilized backbone, in which phosphodiester or phosphodiester-like internucleotide linkages occur only within at least one internal pyrimidine-purine (YZ) dinucleotide. Semi-soft oligonucleotide generally possess increased immunostimulatory potency relative to corresponding fully stabilized immunostimulatory oligonucleotides. Due to the greater potency of semi-soft oligonucleotides, semi-soft oligonucleotides may be used, in some instances, at lower effective concentrations and have lower effective domes than conventional fully stabilized immunostimulatory oligonucleotides in order to achieve a desired biological effect.

It is believed that the foregoing properties of semi-soft oligonucleotides generally increase with increasing "dose" of phosphodiester or phosphodiester-like internucleotide linkages involving internal YZ dinucleotides. Thus it is believed, for example, that generally for a given oligonucleotide sequence with five internal YZ dinucleotides, an oligonucleotide with five internal phosphodiester or phosphodiester-like YZ internucleotide linkages is more immunostimulatory than an oligonucleotide with four internal phosphodiester or phosphodiester-like YG internucleotide linkages, which in turn is more immunostimulatory than an oligonucleotide with three internal phosphodiester or phosphodiester-like YZ internucleotide linkages, which in turn is more immunostimulatory than an oligonucleotide with two internal phosphodiester or phosphodiester-like YZ internucleotide linkages, which in turn is more immunostimulatory than an oligonucleotide with one internal phosphodiester or phosphodiester-like YZ internucleotide linkage. Importantly, inclusion of even one internal phosphodiester or phosphodiester-like YZ internucleotide linkage is believed to be advantageous over no internal phosphodiester or phosphodiester-like YZ internucleotide linkage. In addition to the number of phosphodiester or phosphodiester-like internucleotide linkages, the position along the length of the nucleic acid can also affect potency.

The soft and semi-soft oligonucleotides will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end.

A phosphodiester internucleotide linkage is the type of linkage characteristic of nucleic acids found in nature. The phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAs H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. Nos. 5,177,198; 5,859,231; 6,160,109; 6,207,819; Sergueev et al., (1998) *J Am Chem Soc* 120:9417-27. In another preferred embodiment the phosphodiester-like internucleotide linkage is diasteromerically pure Rp phosphorothioate. It is believed that diasteromerically pure Rp phosphorothioate is more susceptible to nuclease digestion and is better at activating RNAase H than mixed or diasteromerically pure Sp phosphorothioate. Stereoisomers of CpG oligonucleotides are the subject of co-pending U.S. patent application Ser. No. 09/361,575 filed Jul. 27, 1999, and published PCT application PCT/US99/17100 (WO 00/06588). It is to be noted that for purposes of the instant invention, the term "phosphodiester-like internucleotide linkage" specifically excludes phosphorodithioate and methylphosphonate internucleotide linkages.

As described above the soft and semi-soft oligonucleotides of the invention may have phosphodiester like linkages between C and G. One example of a phosphodiester-like linkage is a phosphorothioate linkage in an Rp conformation. Oligonucleotide p-chirality can have apparently opposite effects on the immune activity of a CpG oligonucleotide, depending upon the time point at which activity is measured. At an early time point of 40 minutes, the $R_p$ but not the $S_p$ stereoisomer of phosphorothioate CpG oligonucleotide induces JNK phosphorylation in mouse spleen cells. In contrast, when assayed at a late time point of 44 hr, the $S_p$ but not the $R_p$ stereoisomer is active in stimulating spleen cell proliferation. This difference in the kinetics and bioactivity of the $R_p$ and $S_p$ stereoisomers does not result from any difference in cell uptake, but rather most likely is due to two opposing biologic roles of the p-chirality. First, the enhanced activity of the Rp stereoisomer compared to the Sp for stimulating immune cells at early time points indicates that the Rp may be more effective at interacting with the CpG receptor, TLR9, or inducing the downstream signaling pathways. On the other hand, the faster degradation of the Rp PS-oligonucleotides compared to the Sp results in a much shorter duration of signaling, so that the Sp PS-oligonucleotides appear to be more biologically active when tested at later time points.

A surprisingly strong effect is achieved by the p-chirality at the CpG dinucleotide itself. In comparison to a stereo-random CpG oligonucleotide the congener in which the single CpG dinucleotide was linked in Rp was slightly more active, while the congener containing an Sp linkage was nearly inactive for inducing spleen cell proliferation.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases).

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted unsubstituted aromatic moieties. Other such modifications are well known to those of skill in the art.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann B at al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Ann Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an olignucleotide of the same sequence which is composed of natural DNA or RNA.

For example, the invention relates to an oligonucleotide which may comprise one or more modifications and wherein each modification is independently selected from a) the replacement of a phosphodiester internucleotide bridge located at the 3' and/or the 5' end of a nucleotide by a modified internucleotide bridge, b) the replacement of phosphodiester bridge located at the 3' and/or the 5' end of a nucleotide by a dephospho bridge, c) the replacement of a sugar phosphate unit from the sugar phosphate backbone by another unit, d) the replacement of a β-D-ribose unit by a modified sugar unit, and e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoroamidate, boranophosphate, α-hydroxybenzyl phosphonate, phosphate-($C_1$-$C_{21}$)—O-alkyl ester, phosphate-[($C_6$-$C_{12}$)aryl-($C_1$-$C_{21}$)—O-alkyl]ester, ($C_1$-$C_8$)alkylphosphonate and/or ($C_6$-$C_{12}$) arylphosphonate bridges, ($C_7$-$C_{12}$)-α-hydroxymethyl-aryl (e.g., disclosed in WO 95/01363), wherein ($C_6$-$C_{12}$)aryl, ($C_6$-$C_{20}$)aryl and ($C_6$-$C_{14}$)aryl are optionally substituted by halogen, alkyl, alkoxy, nitro, cyano, and where $R^1$ and $R^2$ are, in independently of each other, hydrogen, ($C_1$-$C_{18}$)-alkyl, ($C_6$-$C_{20}$)-aryl, ($C_6$-$C_{14}$)-aryl-($C_1$-$C_8$)-alkyl preferably hydrogen, ($C_1$-$G_8$)-alkyl, preferably ($C_1$-$C_4$)-alkyl and/or methoxyethyl, or $R^1$ and $R^2$ form, together with the nitrogen atom carrying than, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethylhydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate waits) can be replaced by another unit, wherein the other unit is for example suitable to build up a "morpholino-derivative" oligomer (a described, for example, in Stirchak EP et al. (1989) *Nucleic Acids Res* 17:6129-41), that is, e.g., the replacement by a morpholino-derivative unit; or to build up a polyamide nucleic acid ("PNA"; as described for example, in Nielsen PE et al. (1994) *Bioconjug Cherm* 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—($C_1$-$C_6$)alkyl-ribose, preferably 2'-O—($C_1$-$C_6$) alkyl-ribose is 2'-O-methylribose, 2'-O—(C2-C4)alkenyl-ribose, 2-[(O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) Helv Chin Acta 76:481).

In some preferred embodiments the sugar is 2'-O-methylribose, particularly for one or both nucleotides linked by a phosphodiester or phosphodiester-like internucleotide linkage.

Nucleic acids also include substituted purines and pyrimidines such as C-5 propyne pyrimidine and 7-deaza-7-substituted purine modified bases Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring base. The modified nucleotide base may be, for example, selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 55-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytdine, e.g., N4-ethyldeoxycytidne, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

In particular formulas described herein a set of modified base is defined. For instance the letter Y is used to refer to pyrimidine and in some embodiment a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyluracil, 4-thio-uracil, 5-hydroxy-uracil, 5-propynyl-uracil). Some of the preferred cytosine include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

The letter Z is used to refer to a purine, pyrimidine, or abasic and in some embodiments a guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

The oligonucleotides may have one or more accessible 5' ends. It is possible to create modified oligonucleotides having two such 5' ends. Thia may be achieved, for instance by attaching two oligonucleotide through a 3'-3' linkage to generate an oligonucleotide having one or two accessible 5' ends. The 3'3'-linkage may be a phosphodiester, phosphorothioate or any other modified internucleotide bridge. Methods for accomplishing such linkages are known in the art. For instance, such linkages have been described in Seliger, H.; et al., Oligonucleotide analogs with terminal 3'-3- and 5-5'-internucleotide linkages as antisense inhibitors of viral gene expression, Nucleotides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked nucleic acids where the linkage between the 3'-terminal nucleotides is not a phosphodiester, phosphorothioate or other modified bridge, can be prepared using an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence at al., Sterical recognition by T4 polynucleotide kinase of non-nucleotidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

The oligonucleotides are partially resistant to degradation (e.g., are stabilized). A "stabilized oligonucleotide molecule" shall mean an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucletide from degradation by intracellular exo- and endo-nucleases. Other modified oligonucleotides include phosphodiester modified nucleic acids, combinations of phosphodiester and phosphorothioate nucleic acid, methylphosphonate, methylphosphorothioate, phosphorodithioate, p-ethoxy, and combinations thereof.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In some embodiments the oligonucleotide comprises one or more palindromic sequences. As used herein, "palindrome" and, equivalently, "palindromic sequence" shall refer to an inverted repeat, i.e., a sequence such as ABCDEE'D'C'B'A' in which A and A', B and B', etc., are bases capable of forming the usual Watson-Crick base pairs. In some cases the palindrome is GC-rich. A GC-rich palindrome is a palindrome having a base composition of at least two-thirds G's and C's. In some embodiments the GC-rich domain is preferably 3' to the "B cell stimulatory domain". In the case of a 10-base long GC-rich palindrome, the palindrome thus contains at least 8 G's and C's. In the case of a 12-base long GC-rich palindrome, the palindrome also contains at least 8 G's and C's. In the case of a 14-mer GC-rich palindrome, at least ten bases of the palindrome are G's and C's. In some embodiments the GC-rich palindrome is made up exclusively of G's and C's. In some embodiments the oligonucleotide contain more than one palindromic sequence.

DNA is a polymer of deoxyribonucleotides joined through 3'-5' phosphodiester linkages. Units of the polymer of the invention can also be joined through 3'-5' phosphodiester linkages. However, the invention also encompasses polymers having unusual internucleotide linkages, including specifically 5'-5', 3'-3', 2'-2', 2'-3', and 2'-5' internucleotide linkages. In one embodiment such unusual linkages we excluded from the immunostimulatory DNA motif, even though one or more of such linkages may occur elsewhere within the polymer. For polymers having free ends, inclusion of one 3'-3' internucleotide linkage can result in a polymer having two fee 5' ends. Conversely, for polymers having free ends, inclusion of one 5'-5' internucleotide linkage can result in a polymer having two fee 3' ends.

An immunostimulatory composition of this invention can contain two or more immunostimulatory DNA motifs which can be linked through a branching unit. The internucleotide linkages can be 3'-5', 5'-5, 3'-3, 2'-2', 2'-3', or 2'-5' linkages. Thereby, the nomenclature 2'-5' is chosen according to the carbon atom of deoxyribose. However, if unnatural sugar moieties are employed, such a ring-expanded sugar analogs (e.g., hexanose, cylohexene or pyranose) or bi- or tricyclic sugar analogs, then this nomenclature changes according to the nomenclature of the monomer. The unusual internucleotide linkage can be a phosphodiester linkage, but it can alternatively be modified as phosphorothioate or any other modified linkage as described herein. Formula IV shows a general structure for branched DNA oligomers and modified oligoribonucleotide analogs of the invention via a nucleotidic branching unit. Thereby $Nu_1$, $Nu_2$, and $Nu_3$ can be linked through 3'-5', 5'-5', 3'-3', 2'-2', 2'-3', or 2'-5'-linkages. Branching of DNA oligomers can also involve the use of non-nucleotidic linkers and abasic spacers. In one embodiment, $Nu_1$, $Nu_2$, and $Nu_3$ represent identical or different immunostimulatory DNA motifs.

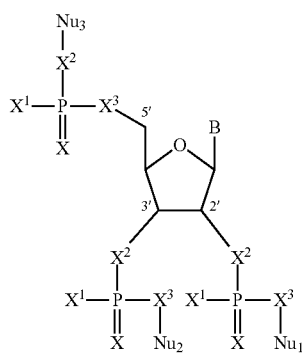

Formula IV

The modified oligoribonucleotide analog may contain a doubler at trebler unit (Glen Research, Sterling, Va.), in particular those modified oligodeoxyribonucleotide analogs with a 3'-3' linkage. A doubler unit in one embodiment can be based on 1,3-bis-[5-(4,4'-dimethoxytrityloxy)pentylamido] prop-2-[(2-cyanoethyl)-(N,N-diisopropyl)]-phosphoramidite. A trebler unit in one embodiment can be based on incorporation of Tris-2,2,2-[3-(4,4'-dimethoxytrityloxy) propyloxymethyl]ethyl-[(2-cyanoethyl)-(N,N-diisopropyl)]-phosphoramidite. Branching of the modified oligoribonucleotide analogs by multiple doubler, trebler, or other multiplier units leads to dendrimers which are a further embodiment of this invention. Branched modified oligoribonucleotide analogs may lead to crosslinking of receptors particularly for combinations of immunostimulatory RNA and DNA such as TLR3, TLR7, TLR8, and TLR9 with distinct immune effects compared to non-branched forms of the analogs. In addition, the synthesis of branched or otherwise multimeric analogs may stabilize DNA against degradation and may enable weak or partially effective DNA sequences to exert a therapeutically useful level of immune activity. The modified oligodeoxyribonucleotide analogs may also contain linker units resulting from peptide modifying reagents or oligonucleotide modifying reagents (Glen Research). Furthermore, the modified oligodeoxyribonucleotide analogs may contain one or more natural or unnatural amino acid residues which are connected to the polymer by peptide (amide) linkages.

The 3'-5', 5'-5',3'-3', 2'-2', 2'-3', and 2'-5'-internucleotide linkages can be direct or indirect. Direct linkages in this context refers to a phosphate or modified phosphate linkage as disclosed herein, without an intervening linker moiety. An intervening linker moiety is an organic moiety distinct from a phosphate or modified phosphate linkage as disclosed herein, which can include, for example, polyethylene glycol, triethylene glycol, hexaethylene glycol, dSpacer (i.e., an abasic deoxynucleotide), doubler unit, or trebler unit.

The linkages are preferably composed of C, H, N, O, S, B, P, and Halogen, containing 3 to 300 atoms. An example with 3 atoms is an acetal linkage (ODNI-3'-O—CH$_2$—O-3'-ODN2) connecting e.g. the 3'-hydroxy group of one nucleotide to the 3'-hydroxy group of a second oligonucleotide. An example with about 300 atoms is PEG-40 (tetraconta polyethyleneglycol). Preferred linkages are phosphodiester, phosphorothioate, methylphosphonate, phosphormidate, boranophosphonate, amide, ether, thioether, acetal, thioacetal, urea, thiourea, sulfonamide, Schiff Base and disulfide linkages. It is also possible to use the Solulink BioConjugation System i.e., (www.trilinkbiotech.com.

If the oligonucleotide is composed of two or more sequence parts, these parts can be identical or different. Thus, in an oligonucleotide with a 3'3'-linkage, the sequences can be identical 5'-ODN1-3'3'-ODN1-5' or different 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides. Preferred are linked oligonucleotides which have two or more unlinked 5'-ends.

The oligonucleotide partial sequences may also be linked by non-nucleotidic linkers. A "non-nucleotidic linker" as used herein refers to any linker element that is not a nucleotide or polymer thereof (i.e., a polynucleotide), wherein a nucleotide includes a purine or pyrimidine nucleobase and a sugar phosphate, in particular abasic linkers (dSpacers), triethylene glycol units or hexaethylene glycol units. Further preferred linkers are alkylamino linkers, such as C3, C6, C12 aminolinkers, and also alkylthiol linkers, such as C3 or C6 thiol linkers. The oligonucleotides can also be linked by aromatic residues which may be further substituted by alkyl or substituted alkyl groups.

For facilitating uptake into cells, the immunostimulatory oligonucleotides are in some embodiments in the range of 3 to 100 bases in length. In some embodiments the oligonucleotides are 7-100 bases in length. Typically, nucleic acids of any size greater than 6 nucleotides (even many kb long) are capable of inducing an immune response according to the invention if sufficient immunostimulatory motifs are present. However, the improved immunostimulatory capacity of the modified oligonucleotides of the invention provides for immunostimulatory molecules of much shorter length. In some embodiments the immunostimulatory oligonucleotides are 3-6 bases in length.

The CpG immunostimulatory oligonucleotides are useful in some aspects of the invention as a vaccine for the treatment of a subject at risk of developing allergy or asthma, an infection with an infectious organism or a cancer in which a specific cancer antigen has been identified. The CpG immunostimulatory oligonucleotides can also be given without the antigen or allergen for protection against infection, allergy or cancer, and in this case repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing allergy or asthma includes those subjects that have been identified as having an allergy or asthma but that don't have the active disease during the CpG immunostimulatory oligonucleotide treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a CpG immunostimulatory oligonucleotide, the subject may be able to kill the cancer cells as they develop. If a tumor begins to form in the subject, the subject will develop a specific immune response against the tumor antigen.

In addition to the use of the CpG immunostimulatory oligonucleotides for prophylactic treatment, the invention also encompasses the use of the CpG immunostimulatory oligonucleotides for the treatment of a subject having an infection, an allergy, asthma, or a cancer.

A subject having an infection is a subject that has been exposed to an infectious pathogen and has acute or chronic detectable levels of the pathogen in the body. The CpG immunostimulatory oligonucleotides can be used with or without an antigen to mount an antigen specific systemic or mucosal immune response that is capable of reducing the level of or eradicating the infectious pathogen. An infectious disease as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide can be administered to a subject to treat or prevent asthma and allergy.

Thus, the CpG immunostimulatory oligonucleotides have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

A subject having a cancer is a subject that has detectable cancerous cells. The cancer may be a malignant or non-malignant cancer. Cancers or tumors include but are not limited to biliary tract cancer; brain cancer; breast cancer; cervical cancer, choriocarcinoma; colon cancer; endometrial cancer; esophageal cancer; gastric cancer; intraepithelial neoplasms; lymphomas; liver cancer, lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or col carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, and allergy/asthma in non human subjects. Cancer is one of the leading causes of death in companion animals (i.e., cats and dogs).

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

In the instances when the CpG oligonucleotide is administered with an antigen, the subject may be exposed to the antigen. As used herein, the term exposed to refers to either the active step of contacting the subject with an antigen or the passive exposure of the subject to the antigen in vivo. Methods far the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the CpG immunostimulatory oligonucleotide. For instance, in a subject at risk of developing a cancer or an in infectious disease or an allergic or asthmatic response, the subject may be administered the CpG immunostimulatory olignucleotide on a regular basis when that risk is greatest, i.e., during allergy season or after exposure to a cancer causing agent. Additionally the CpG immunostimulatory oligonucleotide may be administered to travelers before they travel to foreign lands where they are at risk of exposure to infection agents. Likewise the CpG immunostimulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganisms. A compound is similar to a natural microorganism antigen if it induces an immune response (humoral and/or cellular) to a natural microorganism antigen. Such antigens are used routinely in the art and are well known to those of ordinary skill in the art.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. DNA viruses include Pox, Herpes, Adeno, Papova, Parvo, and Hepadna. RNA viruses include Picorna, Calici, Astro, Toga, Flavi, Corona, Paramyxo, Orthomyxo, Bunya, Arena, Rhabdo, Filo, Borsa, Reo, and Retro. In some aspects, the invention also intends to treat diseases in which prioas are implicated in disease proression such as for example bovine spongifbm encephalopathy (i.e., mad cow disease, BSB) or scrapie infection in animals, or CreuzfeldtJakob disease in humans.

Viruses include, but are not limited to, enteroviruses (including, but not limited to, viruses that the family picornaviridae, such as polio virus, Coxackie virus, echo virus) rotaviruses, adenovirus, and hepatitis virus, such a hepatitis A, B, C D and E. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine cephalitis viruses, rubela vimuses); Flavivirdae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyroviridae (e.g., influenza viruses); Bunyaviridae (e.g., Hantaan viruses, bunya viruses, phlebovirses and Nairo viruses); Arenaviridae (hemorrhagic fever viruses); Reoviridae (e.g., reoviruses, orbiviruses and rotaviruses); Birnavirdae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola vinruses, vaccinia viruses, pox viruses); Iridoviridae (e.g., African swine fever virus); and other viruses acute laryngotracheobronchitis virus, Alphavirus, Kaposi's sarcoma-associated herpesvirus, Newcastle disease virus, Nipah virus, Norwalk virus, Papillomavirus, parainfluenza virus, avian influenza, SARs virus, West Nile virus.

The methods of the invention are particularly useful, in some embodiments, for the treatment of Human immunodeficiency virus (HIV) and hepatitis virus. HIV, a species of retrovirus also known as human T-cell lymphotropic virus III (HTLV III), is responsible for causing the deterioration resulting in the disorder known as AIDS. HIV infects and destroys T-cells, upsetting the overall balance of the immune system, resulting in a loss in the patients ability to combat other infections and predisposing the patient to opportunistic infections which frequently prove fatal.

Viral hepatitis is an inflammation of the liver which may produce swelling, tenderness, and sometimes permanent damage to the liver. If the inflammation of the liver continues at least six months or longer, it is referred to as chronic hepatitis. There are at least five different viruses known to cause viral hepatitis, include hepatitis A, B, C D and B. Hepatitis A is generally communicated through food or drinking water contaminated with human feces. Hepatitis B generally is spread through bodily fluids such as blood. For instance, it may be spread from mother to child at birth, through sexual contact, contaminated blood transfusions and needles. Hepatitis C is quite common and like Hepatitis B is often spread through blood transfusions and contaminated needles. Hepatitis D is found most often in IV drug users who are carriers of the hepatitis B virus with which it co-associates. Hepatitis E is similar to viral hepatitis A and is generally associated with poor sanitation.

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but we not limited to, *Escherichia coli, Pseudomonas* species, and *Salmonella* species. Specific examples of infectious bacteria include but are not limited to, *Helicobacter pyloris, Borella burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus aglactiae* (Group B Streptococcus), *Streptococcus* (viridans group). *Streptococcus faecalis, Streptococcus bovis, Streptococcus* (anaerobic sps.), *Streptococcus pneumoniae*, pathogenic *Campylobacter* sp., *Enterococcus* sp. *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia,* and *Actinomyces israelli.*

Examples of fungi include *Cryptococcus neoformans, Histoplasma capsulatum, Coccidoides immitis, Blastomyces dermatitidis, Chlamydia trachomatis, Candida albicans.*

Other infectious organisms (i.e., protists) include *Plasmodium* spp. such as *Plasmodium falciparum, Plasmodium malariae, Plasmodium ovale,* and *Plasmodium vivax* and *Toxoplasma gondii.* Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.*

Other medically relevant microorganisms have been described extensively in the literature, e.g., see C. G. A Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia arteniisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucosa*); *Quercus* (*Quercus alba*); *Oleo* (*Olea europa*); *Artemisia* (*Artemisia vulgaris*); *Plantago* (e.g. *Plantago lanceolata*); *Parietaria* (eg. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The term substantially purified as used herein refers to a polypeptide which is substantially free of other proteins, lipids, carbohydrates or other materials with which it is naturally associated. One skilled in the at can purify viral or bacterial polypeptides using standard techniques for protein purification. The substantially pure polypeptide will often yield a single major band on a non-reducing polyacrylamide gel. In the case of partially glycosylated polypeptides or those that have several start codon, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are included within the invention.

The oligonucleotides of the invention may be administered to a subject with an anti-microbial agent. An anti-microbial agent as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meaning to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticolds, halofantrine iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethamine-sulfdoxine, quinacrine HCl, quinine sulfate, quinidine gluconate, spiramycin, stibogluconate sodium (sodium antimony gluconate), suramin, tetracycline, doxycycline, thiabendazole, tinidazole, trimethoprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogs), maturation of new virus proteins (e.g. protease inhibitors), and budding and release of the virus.

Nucleotide analogs are synthetic compounds which are similar to nucleotides, but which have an incomplete or abnormal deoxyribose or ribose group. Once the nucleotide analogs are in the cell, they are phosphorylated, producing the triphosphate formed which competes with normal nucleotides far incorporation into the viral DNA or RNA. Once the triphosphate form of the nucleotide analog is incorporated into the growing nucleic acid chain, it causes irreversible association with the viral polymerase and thus chain termination. Nucleotide analogs include, but are not limited to, acyclovir (used for the treatment of herpes simplex virus and varicella-zoster virus), gancyclovir (useful for the treatment of cytomegalovirus), idoxuridine ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant farms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogs, and protease inhibitors. Specific examples of anti-virals include but are not limited to Acemannan; Acyclovir, Acyclovir Sodium; Adefovir; Alovudine; Alvircept Sudotox; Amantadine Hydrochloride; Aranotin; Arildone; Atevirdine Mesylate; Avridine; Cidofovir, Cipamfylline; Cytarabine Hydrochloride; Delavirdine Mesylate; Desciclovir, Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir, Ganciclovir Sodium; Idoxuridine; Kethoxal; Lamivudine; Lobucavir; Memotine Hydrochloride; Methisazone; Nevirapine; Penciclovir, Pirodavir Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate, Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fugal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

CpG immunostimulatory oligonucleotides can be combined with other therapeutic agents such as adjuvants to enhance immune responses. The CpG immunostimulatory oligonucleotide and other therapeutic agent may be administered simultaneously or sequentially. When the other therapeutic agents are administered simultaneously they can be administered in the same or separate formulations, but are administered at the same time. The other therapeutic agents are adminstered sequentially with one another and with CpG immunostimulatory oligonucleotide, when the administration of the other therapeutic agents and the CpG immunostimulatory oligonucleotide is temporally separated. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the CpG immunostimulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The CpG immunostimulatory oligonucleotides are also useful as mucosal adjuvants. It has previously been discovered that both systemic and mucosal immunity are induced by mucosal delivery of CpG nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow at al., 1997; Geissler et al., 1997; Iwasaki et al., 1997; Kim et al., 1997) or B-7 co-stimulatory molecules (Iwasaki et al., 1997; Tsuji et al., 1997) with the CpG immunostimulatory oligonucleotides. The term cytokine is used as a generic name for a diverse group of soluble proteins and peptides which c as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokine include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-$\gamma$ ($\gamma$-IFN), IFN-$\alpha$, tumor necrosis factor (TNF), TGF-$\beta$, FLT-3 ligand, and CD40 ligand.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g. by inducing monocytic cells and other cells to produce Th1 cytokines, including IL-12, IFN-γ and GM-CSF). The redirection or rebalance of the immune response from a T2 to a Th1 response is particularly useful for the treatment or prevention of asthma. For instance, an effective amount for treating asthma can be that mount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The CpG immunostimulatory oligonucleotides of the invention cause an increase in Th1 cytokines which helps to rebalance the immune system, preventing or reducing the adverse effects associated with a predominately Th2 immune response.

The oligonucleotides of the invention may also be useful for treating airway remodeling. Airway remodeling results from smooth muscle cell proliferation and/or submucosal thickening in the airways, and ultimately causes narrowing of the airways leading to restricted airflow. The oligonucleotides of the invention may prevent further remodeling and possibly even reduce tissue build up resulting from the remodeling process.

The oligonucleotide are also useful for improving survival, differentiation, activation and maturation of dendritic cells. The CpG immunostimulatory oligonucleotides have the unique capability to promote cell survival, differentiation, activation and maturation of dendritic cells.

CpG immunostimulatory oligonucleotides also increase natural killer cell lytic activity and antibody dependent cellular cytotoxicity (ADCC). ADCC can be performed using a CpG immunostimulatory oligonucleotide in combination with an antibody specific for a cellular target, such as a cancer cell. When the CpG immunostimulatory oligonucleotide is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art ad many are commercially available.

The CpG immunostimulatory oligonucleotides may also be administered in conjunction with an anti-cancer therapy. Anti-cancer therapies include cancer medicaments, radiation and surgical procedures. As used herein, a "cancer medicament" refer to a agent which is administered to a subject for the purpose of treating a cancer. As used herein, "treating cancer" includes preventing the development of a cancer, reducing the symptoms of cancer, and/or inhibiting the growth of an established cancer. In other aspects the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the CpG immunostimulatory oligonucleotides. As an example, where appropriate, the CpG immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected form the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitoxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitane, Furtulon/Doxifluridine, Cyclopax/oral paclitaxel, Oral Taxcoid, SPU-077/Cisplatin, HMR 1275/Flavopirldol, CP 358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, lodine seeds, CDK4 and CDK2 inhibitors, PARP inhibitors, D4809/Dexifosmaide, Ifes/Mesnes/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nirosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analog), Lomustine (CCNU), Mechlorethamine HCl (nitrogen mustartd) Mercaptopurine, Mesna, Mitotane (o.p.'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyly-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

The cancer vaccine may be selected from the group consisting of EGF, Anti-idiotypic cancer vaccinges, Gp75 antigen, GMK melanoma vaccine, MGV ganglioside conjugate vaccine, Her2/neu, Ovarex, M-Vax, O-Vasx, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmnuCyst/TheraCys, but it is not so limited.

The use of CpG immunostimulatory oligonucleotides in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic ad fetal antigens. Other cancer antigens are encoded by mutant cellular genes, such as oncogens (e.g., activated as oncogene), suppressor genes (e.g., mutant p53), fusion proteins resulting from internal deletions or chromosomal translocations. Still other cancer antigens can be encoded by viral genes such as those carried on RNA and DNA tumor viruses.

The CpG immunostimulatory olignucleotides are also useful for treating and preventing autoimmune disease. Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatold arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytapenic purpura, sclerodema with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the CpG immunostimulatory nucleic acids be administered with self antigens, particularly those that are the targets of the autoimmune disorder.

In other instances, the CpG immunostimulatory nucleic acids may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

The invention also includes a method for inducing antigen non-specific innate immune activation and broad spectrum resistance to infectious challenge using the CpG immunostimulatory oligonucleotides. The term antigen non-specific innate immune activation a used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such a travelers.

The CpG immunostimulatory oligonucleotides may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell. Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the olignucleotide is released in a functional form.

Delivery vehicles or delivery devices for delivering antigen and olignucleotide to surfaces have been described. The CpG immunostimulatory oligonucleotide and/or the antigen and/or other therapeutics may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus calmatte-guerin, Shigella, Lactobacillus*); Live vial vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below in the discussion of vectors.

The term effective amount of a CpG immunostimulatory oligonucleotide refers to the amount necessary or sufficient to realize a desired biologic effect. For example, an effective amount of a CpG immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG immunostimulatory oligonucleotide being administered the size of the subject, or the severity of the disease or condition. One of ordinary skill in the art can empirically determine the effective amount of a particular CpG immunostimulatory oligonucleotide and/or antigen and/or other therapeutic agent without necessitating undue experimentation.

Subject doses of the compounds described herein for mucosal or local delivery typically range from about 0.1 μg to 10 mg per administration, which depending on the application could be given daily, weekly, or monthly and any other amount of time therebetween. More typically mucosal or local doses range from about 10 μg to 5 mg per administration, and most typically from about 100 μg to 1 mg, with 2-4 administrations being spaced days or weeks part. More typically, immune stimulant doses range from 1 μg to 10 mg per administration, and most typically 10 μg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the CpG immunostimulatory oligonucleotides are administered in combination with other therapeutic agents or in specialized delivery vehicles typically range from about 0.1 μg to 10 mg per administration, which depending on the application could be given daily, weekly, or monthly and any other amount of time therebetween. More typically parenteral doses for these purposes range from about 10 μg to 5 mg per administration, and most typically from about 100 μg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based an the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide can be administered to a subject by any mode that delivers the oligonucleotide to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., CpG immunostimulatory oligonucleotides, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cares. Suitable excipients are, in particular, fillers such as sugars, including lactose, sucrose, mannitol, or sorbitol; cellulose preparations such as for example, maize starch, wheat starch, rice starch, potato starch, gelatin, gum tragacanth, methyl cellulose, hydroxypropylmethyl-cellulose sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, caboxymethyl cellulose, dextran, polyvinyl alcohol, polyvinyl pyrrolidone and polyproline Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage as indicated above, are polyethylene glycol moieties.

For the component (or derivative) the location of release may be the stomach, the small intestine (the duodenum, the jejunum, or the ileum), or the large intestine. One skilled in the art has available formulation which will not dissolve in the stomach, yet will release the material in the duodenum or elsewhere in the intestine. Preferably, the release will avoid the deleterious effects of the stomach environment, either by protection of the oligonucleotide (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings ca also be used on tablets, which are not intended for protection against the stomach. This can include sugar coatings, or coatings which make the tablet easier to swallow. Capsules may consist of a hard shell (such as gelatin) for delivery of dry therapeutic i.e. powder, for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly comprised plugs or even as tablets. The therapeutic could be prepared by compression.

Colorants and flavoring agents may all be included. For example, the oligonucleotide (or derivative) may be formulated (such as by liposome or microsphere encapsulation) and then further contained within a edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used a fillers including calcium triphosphate, magnesium carbonate and sodium chloride. Some commercially available diluents are Fast-Flo, Emdex STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange maim. Powdered gums may be used a disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent slicking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such a sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starh, talc, pyrogenic silica and hydrated silicoaluminate.

To aid dissolution of the therapeutic into the aqueous environment a surfactant might be added as a wetting agent. Surfacants may include anionic detergents such a sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the oligonucleotide or derivative either alone or as a mixture in different ratios.

Pharmaceutical preparations which can be used orally include push-fit capsules made of gelatin, as well as soft, sealed capsules made of gelatin and a plasticizer, such a glyceol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the oligonucleotides (or derivatives thereof). The oligonucleotide (or derivative) is delivered to the lungs of a mammal while inhaling and traverses across the lung epithelial lining to the blood stream. Other reports of inhaled molecules include Adjei et al., 1990, Pharmaceutical Research, 7:565-569, Adjei et al., 1990, International Journal of Pharmaceutical, 63:135-144 (leuprolide acetate); Baquet et al., 1989, Journal of Cardiovascular Pharmacology, 13(suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al, U.S. Pat. No. 5,284,656 (granulocyte colony stimulating factor). A method ad composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizes, metered dose inhalers, and powder inhalers, all of which are familiar to those skilled in the art.

Some specific examples of commercially available devices suitable for the practice of this invention are the Ultravent nebulizer manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other type of camera is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide (or derivative) dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder containing the oligonucleotide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide (or derivative) and may also include a bulking agent, such as lactose, sorbitol, sucrose, or mannitol in amounts which facilitate dispersal of the powder from the device, e.g., 50 to 90% by weight of the formulation. The oligonucleotide (or derivative) should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The CpG immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other so therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also as capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Oligodeoxynucleotides (ODN) and Reagents

All ODN were synthesized following standard phosphoramidite chemistry protocols and controlled for identity and purity by Coley Pharmaceutical GmbH and had undetectable endotoxin levels (<0.1 EU/ml) measured by the Limulus assay (BioWhittaker, Verviers, Belgium). ODN were suspended in sterile, endotoxin-free Tris-EDTA (Sigma, Deisenhofen, Germany), and stored and handled under aseptic conditions to prevent both microbial and endotoxin contamination. All dilutions were carried out using endotoxin-free Tris-EDTA.

TLR Assays

HEK293 cells were transfected by electroporation with vectors expressing the respective human TLR and a 6×NF-κB-luciferase reporter plasmid. Stable transfectants ($3 \times 10^4$ cells/well) were incubated indicated amounts of ODN for 16 h at 37° C. in a humidified incubator. Each data point was done in triplicate. Cells were lysed and assayed for luciferase gene activity (using the BriteLite kit from Parkin-Elmer, Zaventem, Belgium). Stimulation indices were calculated in reference to reporter gene activity of medium without addition of ODN.

Cell Purification

Peripheral blood buffy coat preparations from healthy human donors were obtained from the Blood Bank of the University of Düsseldorf (Germany) and PBMC were purified by centrifugation over Ficoll-Hypaque (Sigma). Cells were cultured in a humidified incubator at 37° C. in RPMI 1640 medium supplemented with 5% (v/v) heat inactivated human AB serum (BioWhittaker) or 10% (v/v) heat inactivated FCS, 2 mM L-glutamine, 100 U/ml penicillin and 100 µg/ml streptomycin (all from Sigma).

Cytokine Detection and Flow Cytometric Analysis

PBMC were resuspended at a concentration of $5 \times 10^6$ cells/ml and added to 96 well round-bottomed plates (250 µl/well). PBMC were incubated with ODN and culture supernatants (SN) were collected after the indicated time points. If not used immediately, SN were stored at −20° C. until required.

Amounts of cytokines in the SN were assessed using an in-house ELISA for IFN-α developed using commercially available antibody (PBL, New Brunswick, N.J., USA) or on the Luminex multiplex system (Luminex Corporation, 12212 Technology Boulevard, Austin, Tex. 78727-6115).

Animals

Female BALB/c mice (6-8 weeks of age) were purchased from Charles River Canada (Quebec, Canada) and housed in micro-isolators in the Animal Care Facility at Coley Pharmaceutical Group Canada. All studies were conducted in accordance with the Animal Care Committee of Coley Canada under the guidance of the Canadian Council on Animal Care. All animals were naïve to CpG ODNs.

SAIN tumor model: Female A/J mice (10 per group) were injected SC with $5 \times 10^5$ SaI/N tumor cells on day 0. Mice were treated with 100 µg ODN or PBS alone given SC once weekly starting as day 8 post tumor induction. Animals were monitored for survival and tumor volume. Tumor size (the length and the width) was measured using a digital vernier caliper. Tumor volume was calculated by using the formula Tumor volume=(0.4)(ab2), where a=large diameter and b=smaller diameter.

In Vitro Assays

Naïve BALB/c mouse splenocytes (from pools of 3-5 animals) were used for in vitro assays. Animals were anaesthetized with isoflurane and euthanized by cervical dislocation. Spleens were removed under aseptic conditions and placed in PBS+0.2% bovine serum albumin (Sigma Chemical Company). Spleens were then homogenized and splenocytes were re-suspended in RPMI 1640 (Life Technologies, Grand Island, N.Y.) tissue culture medium supplemented with 2% normal mouse serum (Cedarlane Laboratories, Ontario, Canada) penicillin-streptomycin solution (final concentration of 1000 U/ml and 1 mg/ml respectively, Sigma Chemical Company), and 5×10-5 M b-mercaptoethanol (Sigma Chemical Company).

B Cell Proliferation Assays

Caboxy-florescein diacetate, succimidyl eater (CFSE) (Invitrogen, Eugene, Oreg., USA) stained BALB/c mouse splenocytes ($4 \times 10^5$/well) were incubated with different concentrations of ODN in a humidified 5% $CO_2$ incubator at 37° C. for 5 days. Cells were then stained with PE conjugated anti-CD19 antibody (BD Pharmingen, San Diego, Calif., USA) for CD19 and B-cell proliferation was determined by FACS followed by analysis by ModFit Software V3.0 (Verity Software House Inc., Topsham, Me., USA).

Example 1

Investigation of Structure Activity Relationship at the CpG Motif

It is known that oligonucleotides containing unmethylated CpG motifs are able to stimulate immune responses through the Toll-like receptor 9 (TLR9) pathway. In order to identify oligonucleotides with the greatest ability to stimulate the TLR9 pathway, comprehensive structure activity relationship (SAR) study at the CpG motif was performed. The results showed that substitution of guanine by hypoxanthine and 6-thioguanine leads to a similar activity in hTLR9 assay, while purine, 2-aminopurine, 2,6-diaminopurine, 8-oxo-7,8-dihydroguanine and 7-deazaguanine substitution resulted in a 40-80% reduction in hTLR9 stimulation. Further, modification at C5 and N4 resulted in no stimulation of the hTLR9 pathway. These observations resulted in a SAR model in which guanine is recognized via the Hoogsteen site while cytosine binds at the C,H-Edge to the TLR9 receptor (see FIG. 1a). Thus, no modification at the Hoogsteen recognition site of guanine as well as the C,H-edge of the cytosine was possible without significant loss in hTLR9 activity. None of the investigated base modifications at the dinucleotide motif was more active than the unmodified CpG motif.

Example 2

The Effect of Hydrophobic Thymine Base Shape Analogs Near the CpG Motif

Figure 2:
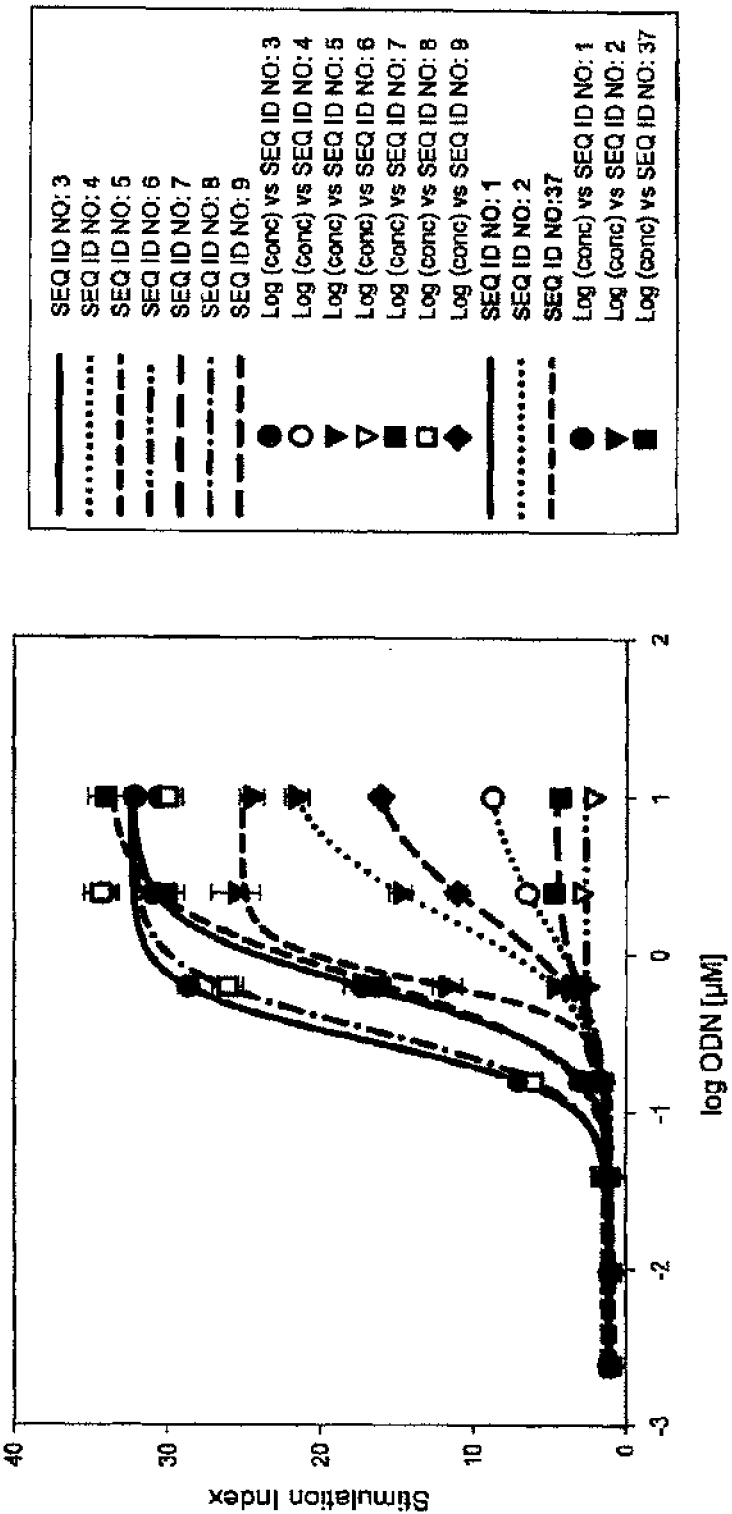
FIG. 2 is a graph showing results of a luciferase assay with B-class oligonucleotides (ODN) modified with thymine shape analog 2,4-difluorotoluene (FF). The activity of FF-modified ODN (SEQ ID NO:3-9) was compared to that of the unmodified B-class parent sequence (SEQ ID NO:1), fully PS parent sequence (SEQ ID NO:2), and a third unmodified B-class ODN (SEQ ID NO:37). hTLR9-LUC-293 cells were stimulated with indicated amounts of ODN and NF-κB stimulation was determined by measuring luciferase activity 16 h later. The x-axis is log ODN concentration in μM and the y-axis is the relative stimulation index.
Figure 3:
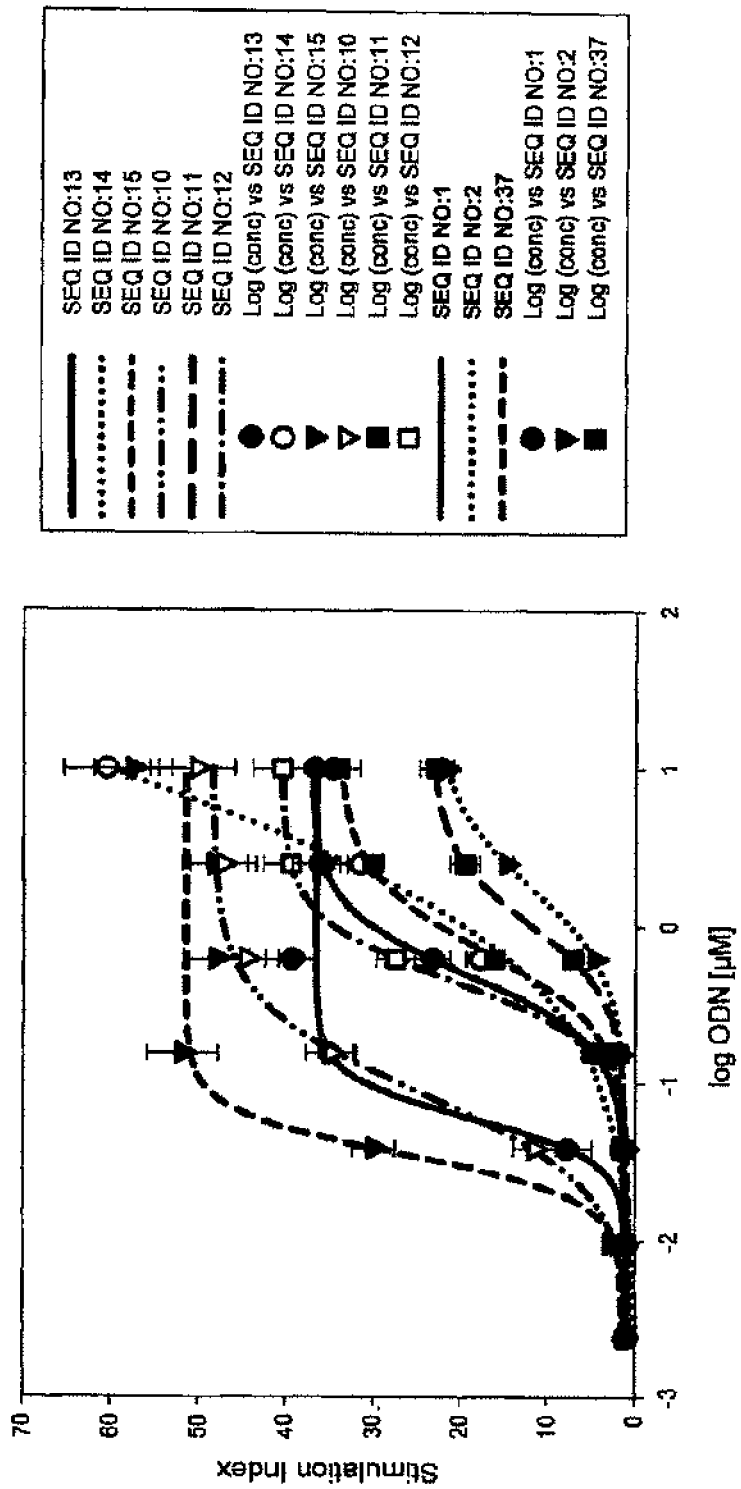
FIG. 3 is a graph demonstrating the results of a luciferase assay with modified B-class ODN. Thymidine (T) was substituted with 5-bromo-2'-deoxyuridine (BU) (SEQ ID NO:10-12) and 5-iodo-2'-deoxyuridine (JU) (SEQ ID NO:13-15). Their activity was compared to that of the unmodified B-class parent sequence (SEQ ID NO:1), fully PS parent sequence (SEQ ID NO:2), and a third unmodified B-class ODN (SEQ ID NO:37). hTLR9-LUC-293 cells were stimulated with indicated amounts of ODN and NF-κB stimulation was determined by measuring Luciferase activity 16 h later. The x-axis is log ODN concentration in μM and the y-axis is the relative stimulation index.
Figure 4:
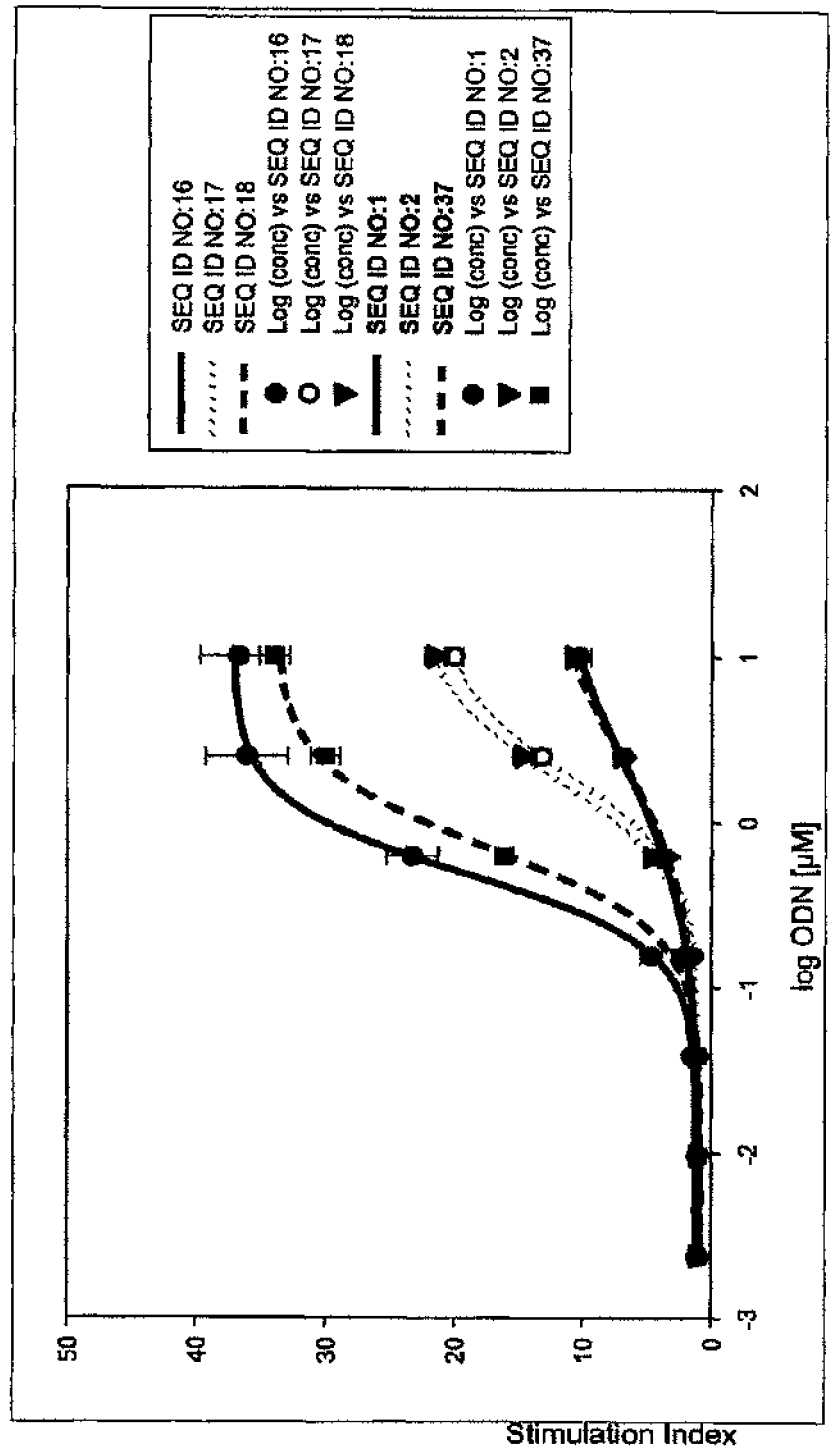
FIG. 4 is a graph demonstrating the results of a luciferase may with modified B-class ODN. 2'-deoxythymidine (T) was substituted with 2'-deoxyuridine (U) (SEQ ID NO:16-18). The activity of the U-modified ODN was compared to that of the unmodified B-class parent sequence (SEQ ID NO:1), fully PS parent sequence (SEQ ID NO:2), and a third unmodified B-class ODN (SEQ ID NO:37). hTLR9-LUC-293 cells were stimulated with indicated amounts of ODN and NF-κB stimulation was determined by measuring Luciferase activity 16 h later. The x-axis is log ODN concentration in μM and the y-axis is the relative stimulation index.

To investigate the impact of the dT residues in neighborhood to the CpG motif, several hydrophobic thymine base shape analogs, such as 2,4-difluorotoluene (FF) (SEQ ID NO:3-9), 5-bromo-2'-deoxyuridine (BU) and 5-iodo-2'-deoxyuridine (JU), were incorporated outside of the CpG motif (see Table 1 and FIGS. 2-3). Surprisingly, incorporation of all tested hydrophobic thymine analogs led to man unusually strong increase in hTLR9 activity, while substitution by uracil residues (thymine with lacking methyl group, FIG. 4) led to a strong decrease in hTLR9 stimulation. The increase in TLR9 stimulation was pronounced when the modification was 5' to the CpG motif Double substitution with 5-iodouracil (JU) 5' and 3' of the CpG motif resulted in most potent stimulation of those tested. In contrast, substitution of guanine and cytosine by 2,4-difluorotoluene at the CpG motif led in both cases to a strong decrease of the TLR9 stimulation index.

Incorporation of hydrophobic T analogs also resulted in a strong enhancement of IFN-alpha induction in human PBMCs. Unexpectedly, modification of man ODN (SEQ ID NO:1) that is virtually inactive in inducing IFN-alpha with 5-bromouridine and 5-iodouridine in particular resulted in increased TLR9 stimulation and IFN-alpha induction. There is usually an inverse correlation between TLR9 and IFN-alpha induction for CpG ODN which do not contain these modifications.

TABLE 1

Examples of modified oligonucleotides with hydrophobic thymine base shape analogs near the CpG motif

| Seq ID No # | Oligonucleotide sequence | Description/class derived from |
|---|---|---|
| 1 | T*G*T*C-G*T*T*T*T*T*T*T*T*T*T*T*T*T*T | 1xPO of SEQ ID NO: 2 |
| 2 | T*G*T*C*G*T*T*T*T*T*T*T*T*T*T*T*T*T*T | |
| 3 | T*G*FF\*C-G*T*T*T*T*T*T*T*T*T*T*T*T*T*T | 5'FF derivative of SEQ ID NO: 1 |
| 4 | T*G*T*C-G*FF\*T*T*T*T*T*T*T*T*T*T*T*T*T | 3'FF derivative of SEQ ID NO: 1 |
| 5 | T*G*FF\*C-G*FF\*T*T*T*T*T*T*T*T*T*T*T*T*T | 3' and 5'FF derivative of SEQ ID NO: 1 |
| 6 | T*G*T*FF-G*T*T*T*T*T*T*T*T*T*T*T*T*T*T | C->FF |
| 7 | T*G*T*C-FF\*T*T*T*T*T*T*T*T*T*T*T*T*T*T | G->FF |
| 8 | T*FF\*C-G*T*T*T*T*T*T*T*T*T*T*T*T*T*T | GT->FF |
| 9 | T*G*T*C-G*T*FF\*T*T*T*T*T*T*T*T*T*T*T*T | 3'FF derivative of SEQ ID NO: 1 |
| 10 | T*G*BU\*C-G*T*T*T*T*T*T*T*T*T*T*T*T*T*T | 5'BU derivative of SEQ ID NO: 1 |
| 11 | T*G*T*C-G*BU\*T*T*T*T*T*T*T*T*T*T*T*T*T | 3'BU derivative of SEQ ID NO: 1 |
| 12 | T*G*BU\*C-G*BU\*T*T*T*T*T*T*T*T*T*T*T*T*T | 3' and 5'BU derivative of SEQ ID NO: 1 |
| 13 | T*G*JU\*C-G*T*T*T*T*T*T*T*T*T*T*T*T*T*T | 5'JU derivative of SEQ ID NO: 1 |
| 14 | T*G*T*C-G*JU\*T*T*T*T*T*T*T*T*T*T*T*T*T | 3'JU derivative of SEQ ID NO: 1 |
| 15 | T*G*JU\*C-G*JU\*T*T*T*T*T*T*T*T*T*T*T*T*T | 3' and 5'JU derivative of SEQ ID NO: 1 |

TABLE 1-continued

Examples of modified oligonucleotides with hydrophobic thymine base shape analogs near the CpG motif

| Seq ID No# | Oligonucleotide sequence | Description/class derived from |
|---|---|---|
| 16 | T*G*U\*C-G*T*T*T*T*T*T*T*T*T*T*T*T*T*T | 5'U derivative of SEQ ID NO: 1 |
| 17 | T*G*T*C-G*U\*T*T*T*T*T*T*T*T*T*T*T*T*T*T | 3'U derivative of SEQ ID NO: 1 |
| 18 | T*G*U\*C-G*U\*T*T*T*T*T*T*T*T*T*T*T*T*T*T | 3' and 5'U derivative of SEQ ID NO: 1 |

*phosphorothioate internucleotide linkage
-phosphodiester internucleotide linkage

Example 3

Activation of TLR9 with Lipophilic Base Shape Substitutions

Figure 5B:
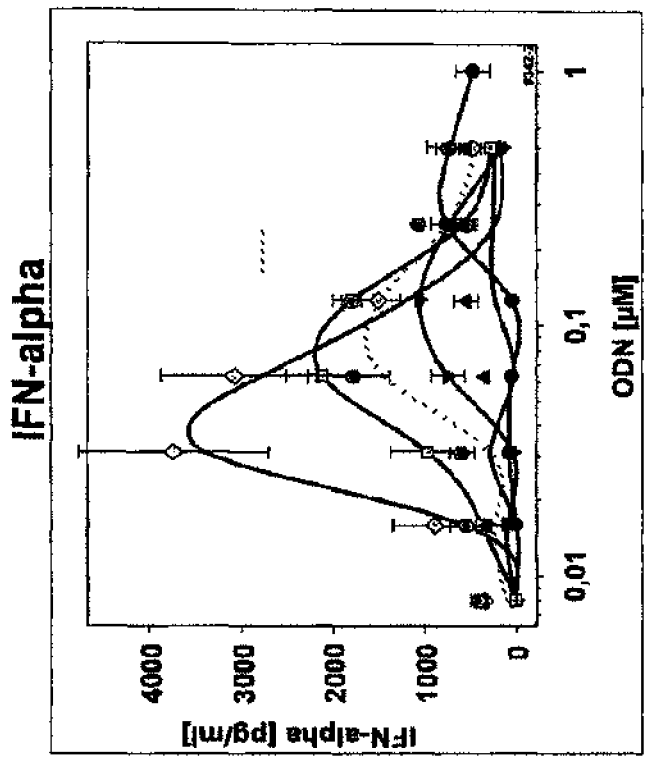
FIG. 5a shows TLR9 activity and FIG. 5b shows IFN-alpha production. Shown is the mean+/−SEM of three donors. The x-axes are ODN concentration in μM and the y-axes are the relative stimulation index (FIG. 5a) or IFN-alpha concentration in pg/ml (FIG. 5b).

Since different types of lipophilic substitution of the base 5' to the CpG motif caused significant increases in stimulation of hTLR9, other base analogs, such as 5-chloro-uracil, 5-trifluoromethyl-uracil, phenyl, aryl and substituted aryl residues were investigated for their ability to stimulate hTLR9 (Table 3). To investigate activation of human TLR9 by B-class oligonucleotides modified with various lipophilic base analogs, B-class ODN SEQ ID NO:1 was modified with 5-Chloro-2'-deoxyuridine (CU), 5-Bromo-2'-deoxyuridine (BU), 5-Iodo-2'-deoxyuridine (JU) and 5-Ethyl-2'-deoxyuridine (EU). hTLR9-NFkB-293 cells were incubated with the indicated ODN (FIG. 5a) for 16 hours. Cells were than lysed and luciferase activity was determined. CU-modified (SEQ ID NO:41), BU-modified (SEQ ID NO:10) JU-modified (SEQ ID NO:13) and EU-modified (SEQ ID NO:42) oligonucleotides all showed greater stimulation of TLR9 activity over control (SEQ ID NO:1). SEQ ID NO:16 with uridine modification showed dramatically decreased activity. In a second experiment IFN-alpha production was measured (FIG. 5b). Human PBMC were incubated with the modified ODN as indicated for 24 h, after which the supernatants we tested by ELISA. JU-modified, BU-modified, and EU-modified ODN resulted in the greatest increase in IFN-alpha over control. These data demonstrate that 5'-substitution of dU on a B-class ODN increases TLR9 activity and IFN-alpha production.

Figure 6:
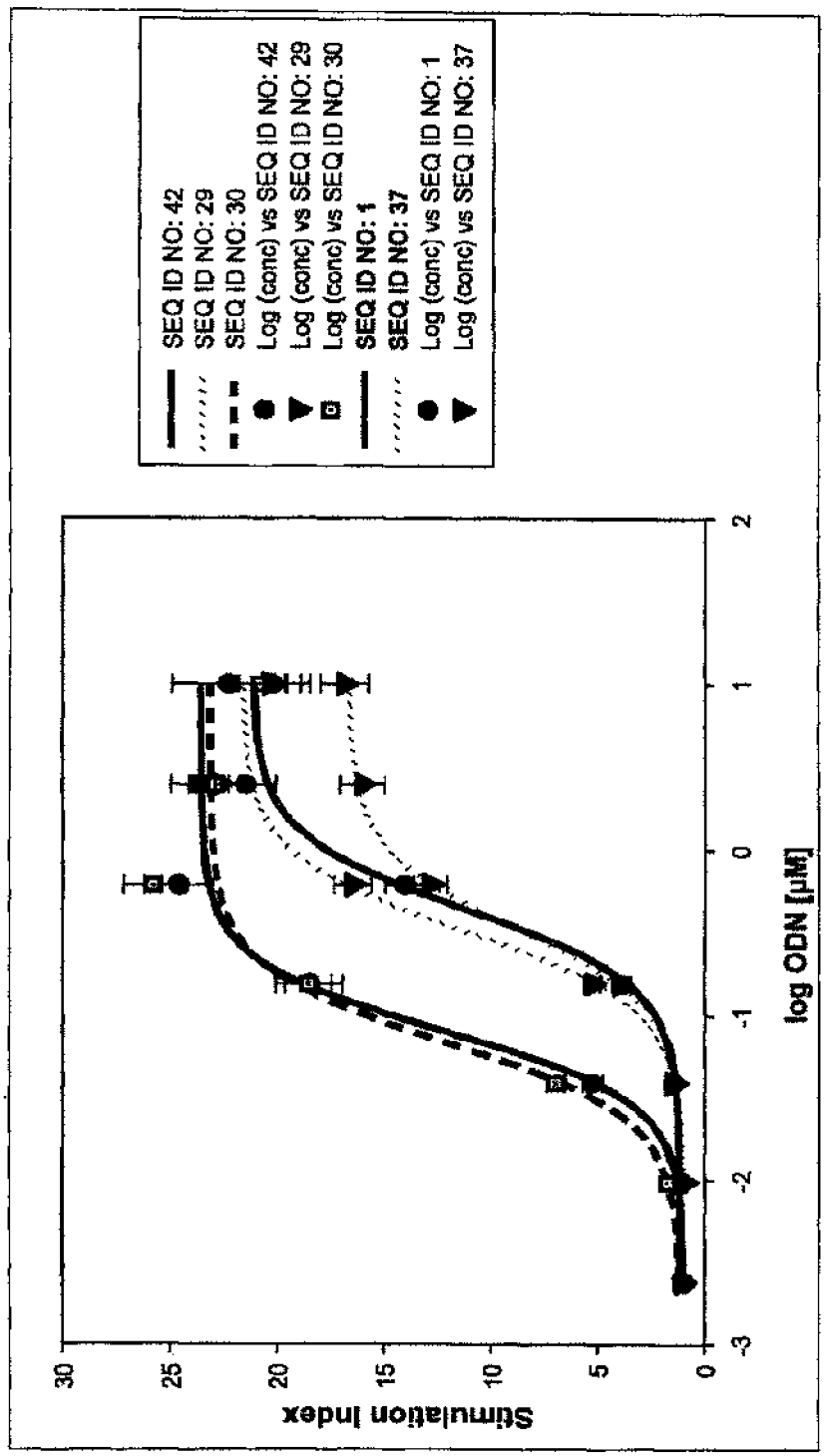
FIG. 6 is a graph demonstrating the results of a luciferase assay with BU-modified ODN. The activity of EU-modified ODN SEQ ID NO:29, 30, and 42 was compared to that of the parent sequence (SEQ ID NO:1) and another unmodified B-class ODN (SEQ ID NO:37). The x-axis is ODN concentration in μM and the y-axis is the relative stimulation index.

To further investigate the effect of EU modification on TLR9 activation, the experiment was repeated with modified oligonucleotides having EU modifications 5' of the CpG (SEQ ID NO:42), 3' of the CpG (SEQ ID NO:29), and 5' and 3' of the CpG (SEQ ID NO:30). SEQ ID NOs 42 and 30 showed a significant increase in TLR9 activation over unmodified SEQ ID NO:1 and unmodified B class ODN SEQ ID NO:37 (FIG. 6).

TABLE 2

Examples of modified oligonucleotides with lipophilic base analog substitutions

| Seq ID No# | Oligonucleotide sequence | Description/class derived from |
|---|---|---|
| 1 | T*G*T*C-G*T*T*T*T*T*T*T*T*T*T*T*T*T*T | Unmodified |
| 41 | T*G*CU\*C-G*T*T*T*T*T*T*T*T*T*T*T*T*T*T | Cl derivative of SEQ ID NO: 1 |
| 10 | T*G BU\*C-G*T*T*T*T*T*T*T*T*T*T*T*T*T*T | 5'BU derivative of SEQ ID NO: 1 |
| 13 | T*G*JU\*C-G*T*T*T*T*T*T*T*T*T*T*T*T*T*T | 5'JU derivative of SEQ ID NO: 1 |
| 16 | T*G*U*C-G*T*T*T*T*T*T*T*T*T*T*T*T*T*T | U derivative of SEQ ID NO: 1 |
| 41 | T*G*CU\*C-G*T*T*T*T*T*T*T*T*T*T*T*T*T*T | CU derivative of SEQ ID NO: 1 |
| 42 | T*G*EU\*C-G*T*T*T*T*T*T*T*T*T*T*T*T*T*T | EU derivative of SEQ ID NO: 1 |
| 29 | T*G*T*C-G*EU\*T*T*T*T*T*T*T*T*T*T*T*T*T*T | 3' EU derivative of SEQ ID NO: 1 |
| 30 | T*G*EU\*C-G*EU\*T*T*T*T*T*T*T*T*T*T*T*T*T*T | 5'3' EU derivative of SEQ ID NO: 1 |

*phosphorothioate internucleotide linkage
-phosphodiester internucleotide linkage

Example 4

Lipophilic Substitution on Oligonucleotides of A, B, C, P, and T Classes

To investigate the effects of lipophilic base analog substitution on the different classes of ODN, modifications were made on A class, B class, C class, P class, and T class oligonucleotides. Some examples of these oligonucleotides are given in Table 3.

TABLE 3

JU-modified oligonucleotides of A, B, C, P, and T class

| Seq ID No. | Modified Oligonucleotide | Oligo Class |
|---|---|---|
| 16 | T*G*U\*C-G*T*T*T*T*T*T*T*T*T*T*T*T*T*T | B |
| 17 | T*G*T*C-G*U\*T*T*T*T*T*T*T*T*T*T*T*T*T | B |
| 18 | T*G*U\*C-G*U\*T*T*T*T*T*T*T*T*T*T*T*T | B |
| 19 | JU\*C*G*T*C*G*T*T*T*T*T*C*G*G*T*C*G*T*T*T*T | B |
| 20 | T*C*G*JU\*C\*G*T*T*T*T*T*C*G*G*T*C*G*T*T*T*T | B |
| 21 | T*C*G*T*C*G*T*T*T*T*T*C*G*G*JU\*C*G*T*T*T*T | B |
| 22 | JU\*C*G*JU\*C*G*T*T*T*T*T*C*G*G*T*C*G*T*T*T*T | B |
| 23 | T*C*G*JU\*C*G*JU\*T*T*T*T*C*G*G*T*C*G*T*T*T*T | B |
| 24 | T*C*G*T*C*G*T*T*T*T*T*C*G*G*JU\*C*G*JU\*T*T*T | B |
| 25 | T*C*T*T*T*T*T*G*T*C-G*T*T*T*T*T*T*T*T*T | T |
| 26 | T*G*C*T*G*C*T*T*T*T*G*T*G*C*T*T*T*T*G*T*G*C*T*T | Non CpG ODN |
| 27 | JU\*C-G*T*C*G*T*T*T*T*A*C*G*G*C*G*C*C*G*T*G*C*C*G | C |
| 28 | T*C*G*JU\*C-G*T*T*T*T*A*C*G*G*C*G*C*C*G*T*G*C*C*G | C |
| 31 | JU\*C-G*T*C*G*A*C*G*A*T*C*G*G*C*G*C*G*C*C*G | P |
| 32 | T*C*G*JU\*C-G*A*C*G*A*T*C*G*G*C*G*C*G*C*G*C*C*G | P |
| 33 | JU\*C-G*JU\*C*G*A*C*G*A*T*C*G*G*C*G*C*G*C*G*C*C*G | P |
| 34 | JU\*C-G-A-C-G-T-C-G-T-G-G*G G*G | A |
| 35 | T*C-G-A-C-G-JU-C-G-T-G-G*G G*G | A |
| 36 | T*C-G-A-C-G-JU-C-G-JU-G-G*G G*G | A |
| 37 | T*C*G*T*C*G*T*T*T*T*T*C*G*G*T*C*G*T*T*T*T | B |
| 43 | T*C-G-A-C-G-T-C-G-T-G-G*G G*G | A |
| 44 | JU\*C-G*JU\*C*G*T*T*T*T*A*C*G*G*C*G*C*C*G*T*G*C*C*G | P |
| 45 | T*C*G*JU\*C-G*JU\*T*T*T*A*C*G*G*C*G*C*C*G*T*G*C*C*G | P |
| 46 | T*C*G*T*C-G*T*T*T*T*A*C*G*G*C*G*C*C*G*T*G*C*C*G | P |
| 47 | T*C*T*T*T*T*T*T*G*JU\*C-G*T*T*T*T*T*T*T*T*T | T |
| 48 | T*C*T*T*T*T*T*T*G*JU\*C-G*JU\*T*T*T*T*T*T*T*T | T |
| 49 | JU\*C*T*T*T*T*T*T*G*T*C-G*T*T*T*T*T*T*T*T*T | T |
| 50 | JU\*C-T*T*T*T*T*T*G*T*C-G*T*T*T*T*T*T*T*T*T | T |
| 51 | T*C*T*T*T*T*T*T*G*U\*C-G*T*T*T*T*T*T*T*T*T | T |
| 52 | T*C-G*T*C*G*A*C*G*A*T*C*G*G*C*G*C*G*C*G*C*C*G | P |

Figure 7:
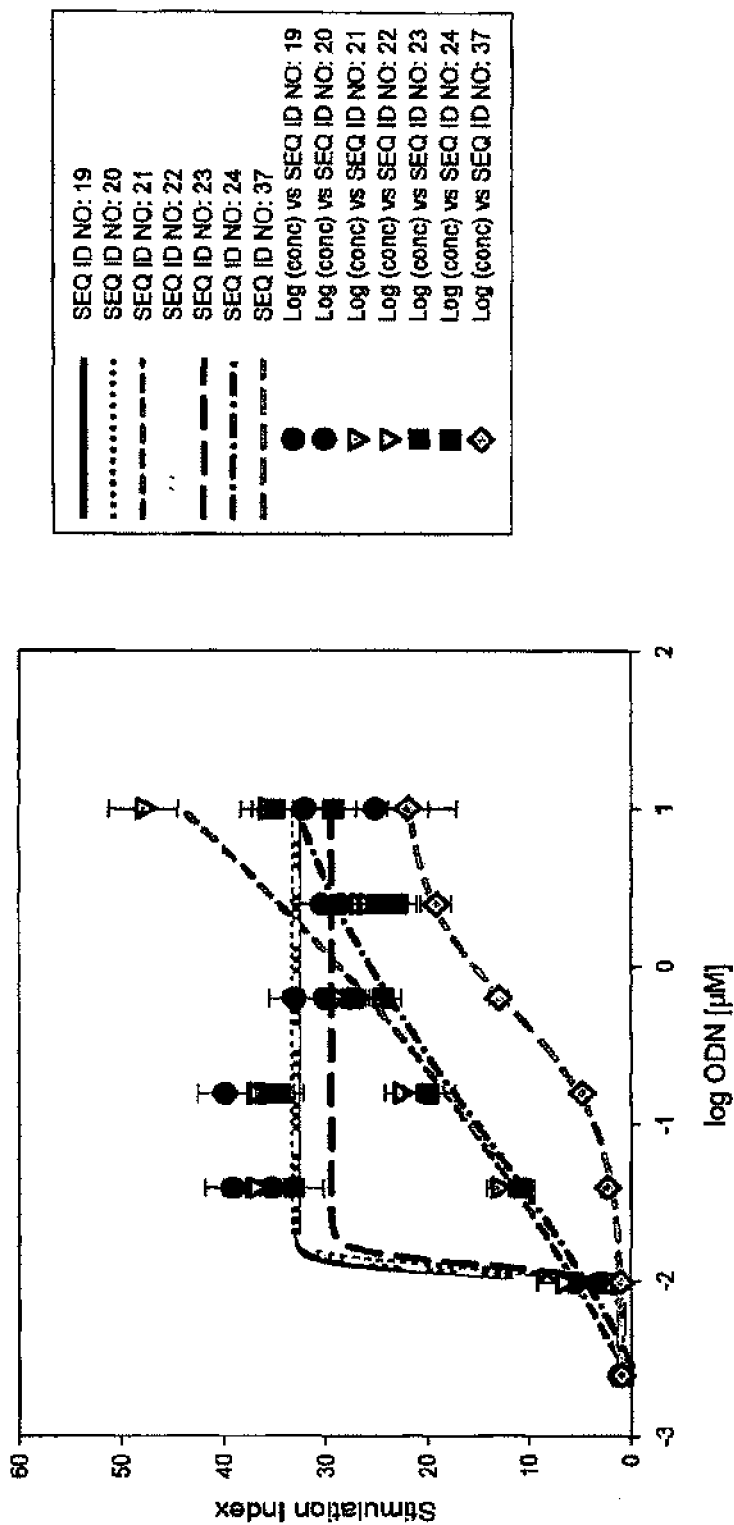
FIG. 7 is a graph demonstrating the results of a luciferase may with modified B class ODN. The activity of JU-modified SEQ ID NO:19-24 was compared to that of parent sequence SEQ ID NO:37. The x-axis is ODN concentration in μM and the y-axis is the relative stimulation index.

\*phosphorothioate internucleotide linkage  
-phosphodiester internucleotide linkage To investigate activation of human TLR9 by modified B class oligonucleotides, 5-iodo-2'-deoxyuridine-modified B-class derivatives of SEQ ID NO:37 were evaluated in a luciferase assay for their ability to activate TLR9 (see materials and methods). All modified B-class oligonucleotides showed a significant increase in TLR9 activation over unmodified SEQ ID NO:37 (FIG. 7).

Figure 5A:
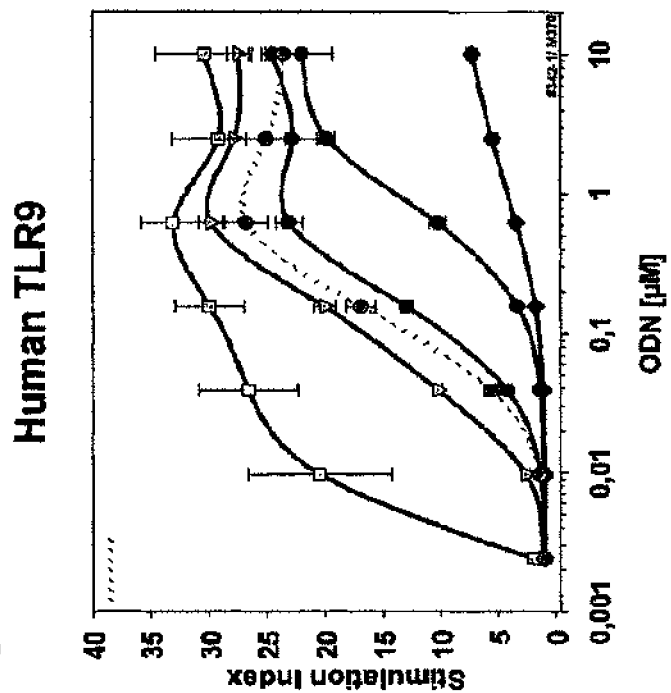
Figure 8B:
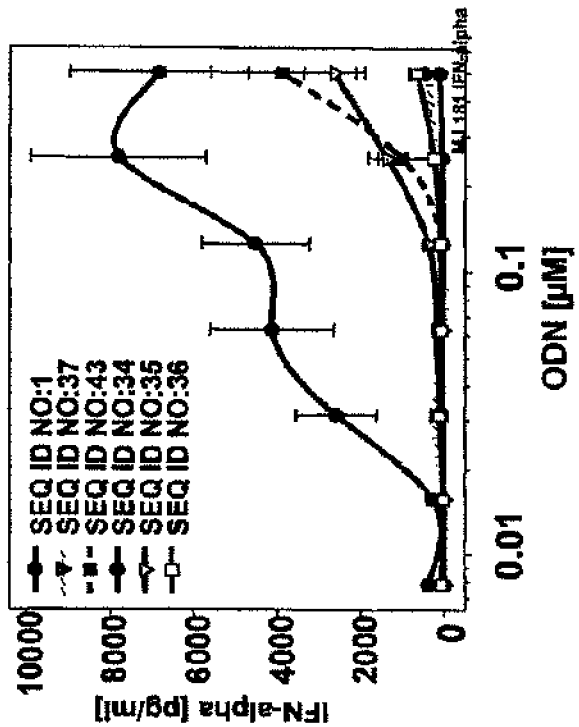
FIG. 8a shows TLR9 activity and FIG. 8b shows IFN-alpha production. Shown is the mean+/−SEM of three donors. The x-axes are log ODN concentration (FIG. 8a) or ODN concentration (FIG. 8b) in μM and the y-axes are the relative stimulation index (FIG. 8a) or IFN-alpha concentration in pg/ml (FIG. 8b).
Figure 8A:
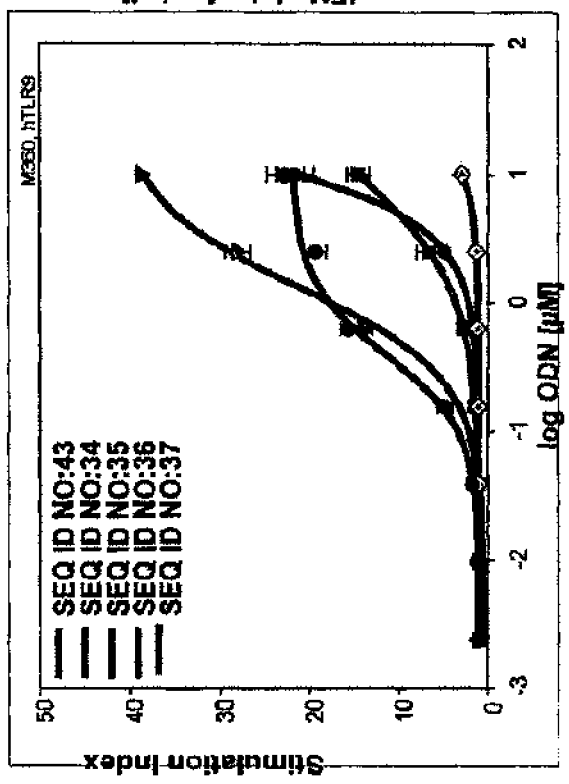

To investigate activation of human TLR9 by modified A-class oligonucleotides, 5-iodo-2'-deoxyuridine-modified A-class derivatives of SEQ ID NO:43 were tested for their ability to activate TLR9 in a luciferase assay (FIG. 5a) and a PBMC assay (FIG. 8b) as in FIG. 5. The increase in TLR9 stimulation was pronounced when the modification was 5' to the CpG motif, although double substitution with 5-iodouracil (JU) 5' and 3' of the CpG motif resulted in most potent stimulation.

Figure 9:
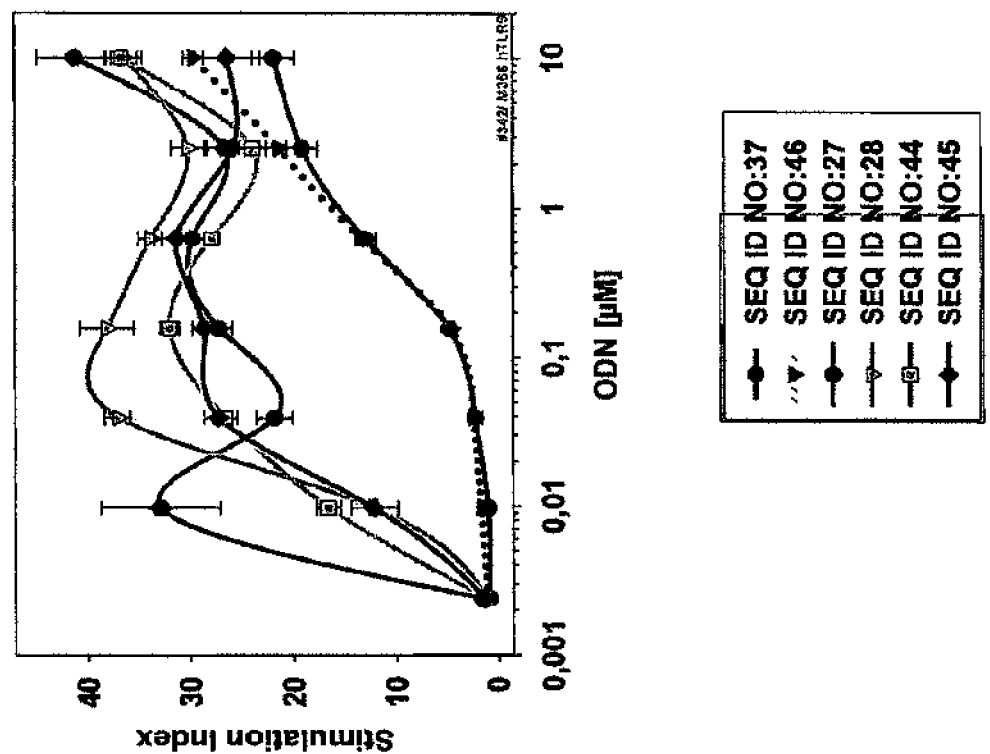
FIG. 9 is a graph demonstrating the results of a luciferase assay with modified C class ODN. The activity of JU-modified C-class ODN SEQ ID NO:27-28 and 44-45 was compared to that of the unmodified parent sequence SEQ ID NO:45 and to an unmodified B-class ODN (SEQ ID NO:37). The x-axis is ODN concentration in μM and the y-axis is the relative stimulation index.
Figure 10:
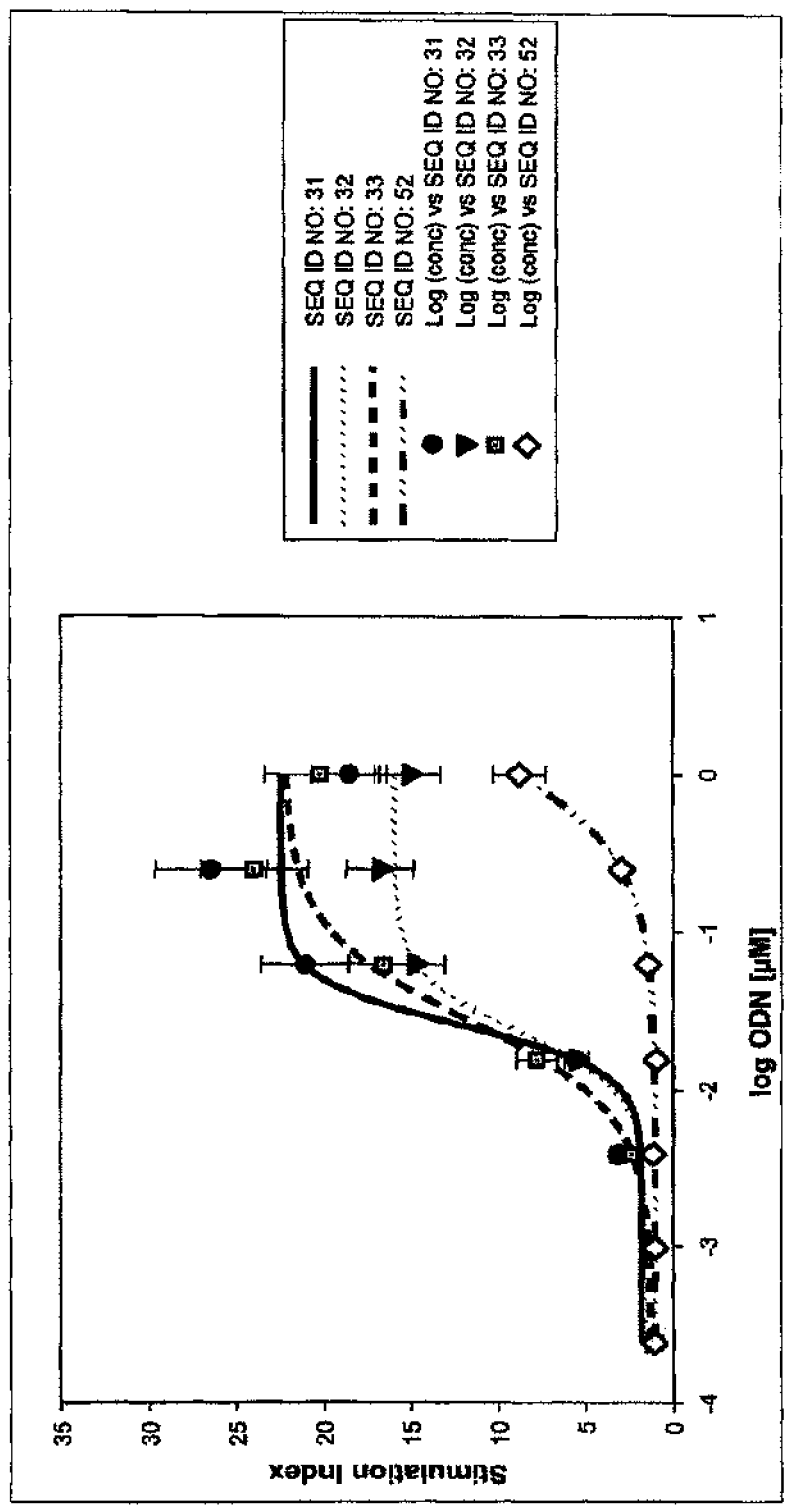
FIG. 10 is a graph demonstrating the results of a luciferase assay with modified P class ODN. The activity of JU-modified SEQ ID NO:31-33 was compared to that of the unmodified parent sequence (SEQ ID NO:52). The x-axis is log ODN concentration in μM and the y-axis is the relative stimulation index.

To investigate the activation of human TLR9 by modified C class oligonucleotides 5-iodo-2'-deoxyuridine-modified C class derivatives of SEQ ID NO:46, SEQ ID NO:44 and 45, were tested for their ability to activate TLR9. A class sequences SEQ ID NO:43 (unmodified) and SEQ ID NO:35 and 36 were tested simultaneously. As shown in FIG. 9, modified ODN SEQ ID NO:35, 36, 44, and 45 all showed increased stimulation of TLR9 above unmodified A and C class in a luciferase assay. To investigate the activation of human TLR9 by modified P class oligonucleotides, 5-iodo-2'-deoxyuridine-modified P class derivatives of SEQ ID NO:46 were tested for their ability to activate TLR9 in a luciferase assay. As shown in FIG. 10, modified ODN SEQ ID NO: 31-33 showed an increased stimulation of TLR9 over unmodified ODN.

Figure 11:
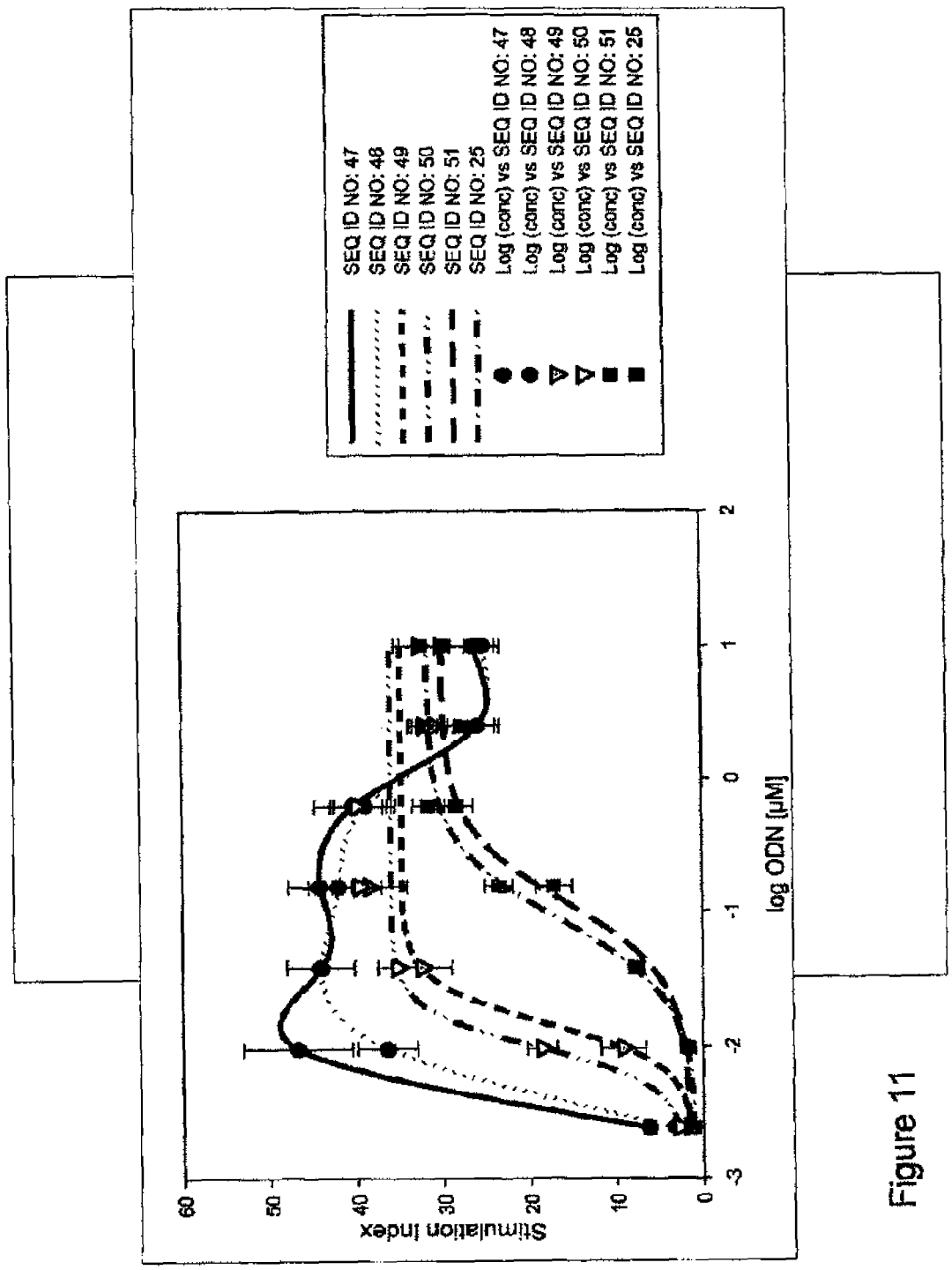
FIG. 11 is a graph demonstrating the results of a luciferase assay with modified T class ODN. The activity of JU-modified SEQ ID NO:47-50 and U-modified SEQ ID NO:51 was compared to that of unmodified parent sequence SEQ ID NO:25. The x-axis is log ODN concentration in μM and the y-axis is the relative stimulation index.

To investigate the activation of human TLR9 by modified T class oligonucleotides, 5-iodo-2'-deoxyuridine-modified T class derivatives of unmodified T class ODN SEQ ID NO:52 were tested for their ability to activate TLR9. As shown in FIG. 11, modified ODN SEQ ID NOs 47-50 showed an increased stimulation of TLR9 over unmodified T class ODN in a luciferase assay. The uridine derivative SEQ ID NO:51 showed reduced stimulation of TLR9.

As the above examples demonstrate, substitution of lipophilic T-analogs 5' to the CpG motif results in a strong increase in TLR9 activation in all classes tested, and resulted in an increased ability to induce IFN-alpha production.

Example 5

Stimulation of TLR9 by Short Modified Oligonucleotides

Figure 12A:
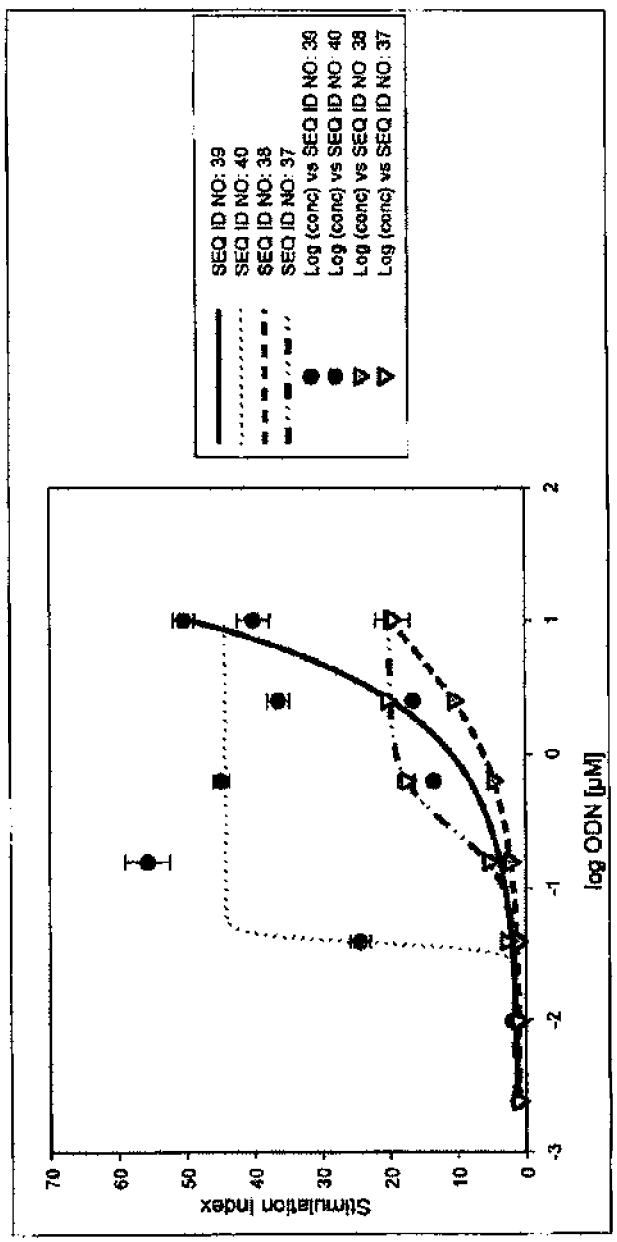
FIGS. 12a-b are graphs demonstrating the results of a luciferase assay with short ODN. The activity of JU-modified short ODN SEQ ID NO:39-40 was compared to that of the unmodified parent sequence SEQ ID NO:38 and to the B-class ODN SEQ ID NO:37. ODN were formulated with and without DOTAP. The x-axis is log ODN concentration in μM and the y-axis is the relative stimulation index.
Figure 12:
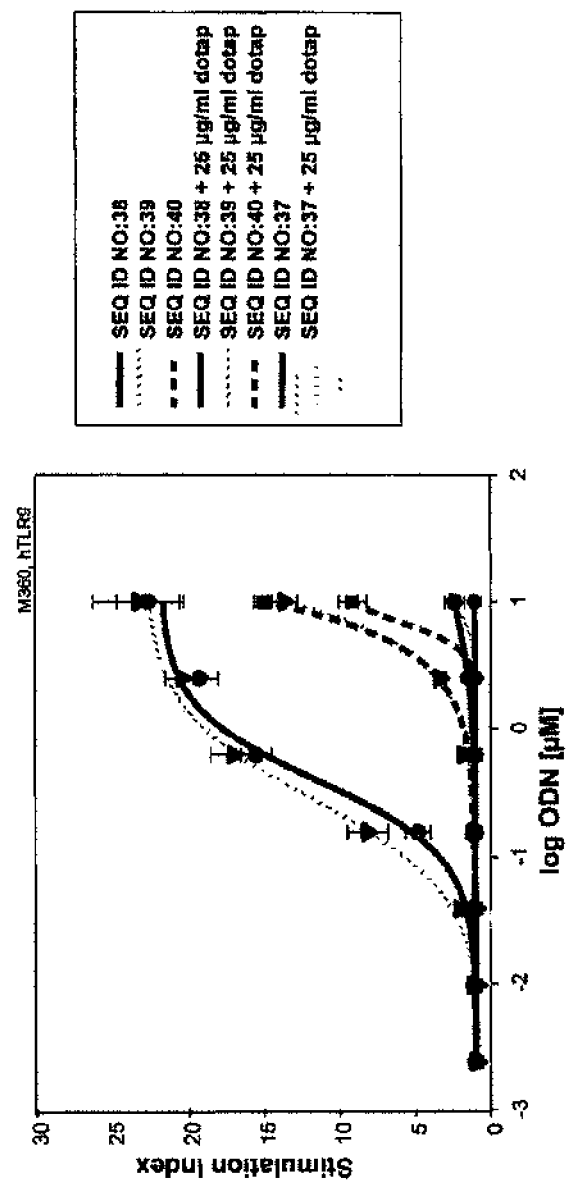

As the modified CpG ODN of 20 nucleotides in length showed an unusual affinity for TLR9 activation, very short CpG ODN were investigated for their ability to activate TLR9. Very short oligonucleotides would be a great advantage over longer oligonucleotides for use in treatment because of the increased ease in uptake by cells, as well as the potential a simpler formulation, without the use of DOTAP. Three short CpG ODN (shortmers) were investigated (Table 3): a 6-mer CpG motif hexamer (SEQ ID NO:38), a 5'JU modification of the hexamer (SEQ ID NO:39), and a 5'3' JU modification of the hexamer (SEQ ID NO:40) (Table 4). The activity of the shortmers was compared to the unmodified B class oligonucleotide SEQ ID NO:37 in a luciferase assay. As shown in FIG. 12, most particularly with SEQ ID NO:40, the use of modified shortmers shows great potential as improved immunotherapy medicament.

TABLE 4

Modified short oligonucleotides

| Seq ID No. | Shortmer sequence | Modification |
|---|---|---|
| 38 | G*T*C-G*T*T | Unmodified |
| 39 | G*JU*C-G*T*T | 5' JU |
| 40 | G*JU*C-G*JU*T | 5' and 3' JU |
| 37 | T*C*G*T*C*G*T*T*T*T*C*G*G*T*C*G*T*T*T*T | Unmodified B class |

*phosphorothioate internucleotide linkage
-phosphodiester internucleotide linkage

Example 6

Activation of TLR9 Pathway In Vivo by Modified Oligonucleotides

Figure 13:
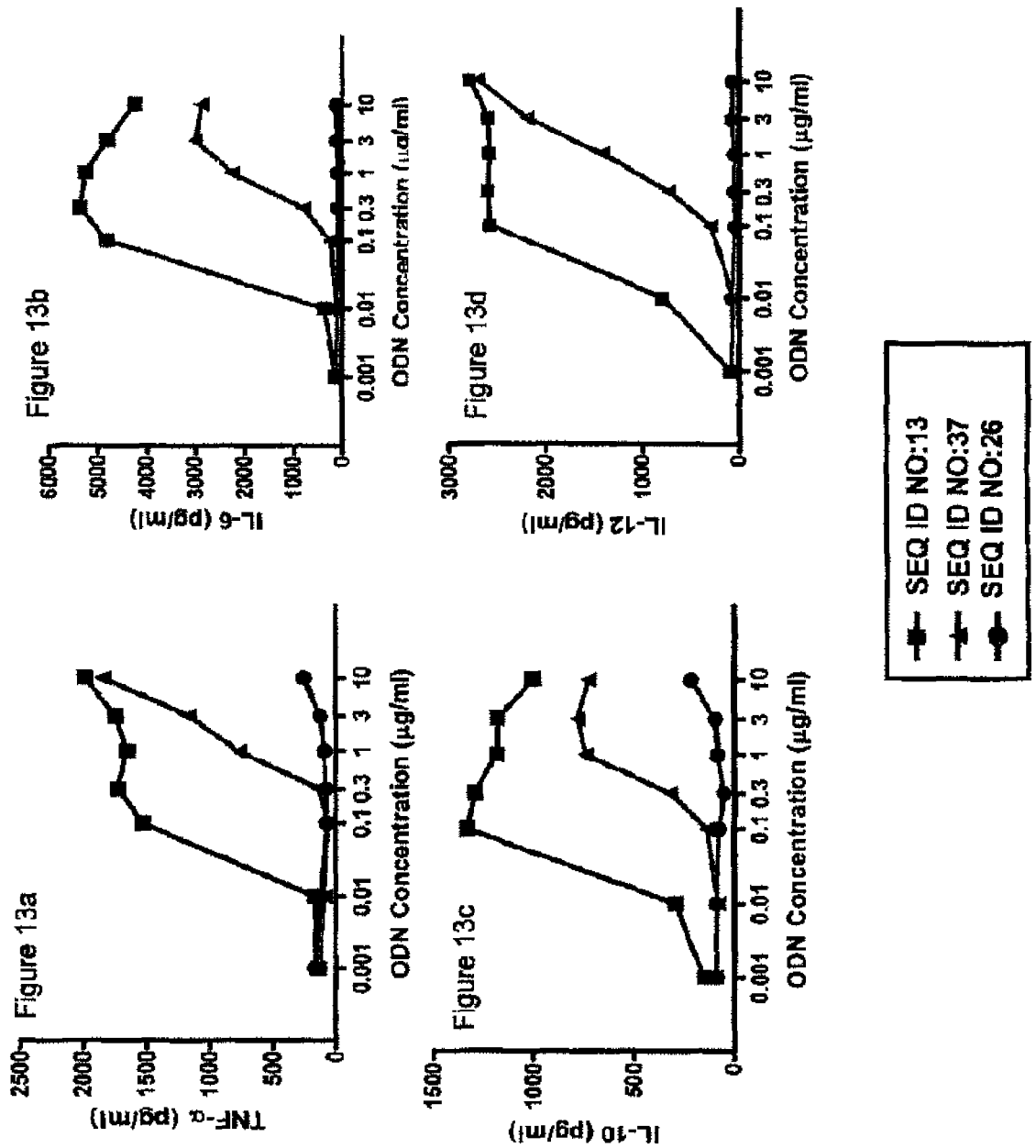
FIG. 13 is four graphs showing the results of an ELISA assay measuring cytokine concentration in splenocyte culture supernatants where BALB/c mouse splenocytes were cultured with different ODNs. Culture supernatants were harvested at 6 hr (for TNF-alpha) or 24 hr (for IL-6, IL-10 and IL-12). The activities of a JU-modified B-class ODN (SEQ ID NO: 13), an unmodified B-class ODN (SEQ ID NO:37), and a non-CpG negative control ODN (SEQ ID NO:26) were compared.

In order to determine the efficacy of the modified ODN of the invention in vivo, ODN with lipophilic T analogs were tested in isolated mouse splenocytes. BALB/c mouse splenocytes was isolated and incubated with modified B class (SEQ ID NO:13), unmodified B class (SEQ ID NO:37), and a non-CpG ODN (SEQ ID NO:26) (Table 5). Culture supernatants were collected at 6 hour (TNF-alpha) or 24 hours (IL-6, IL-10, IL-12) and cytokine concentration was measured by ELISA. As shown in FIG. 13, incubation with modified SEQ ID NO:13 resulted in dramatically increased levels of all cytokines tested.

Figure 14:
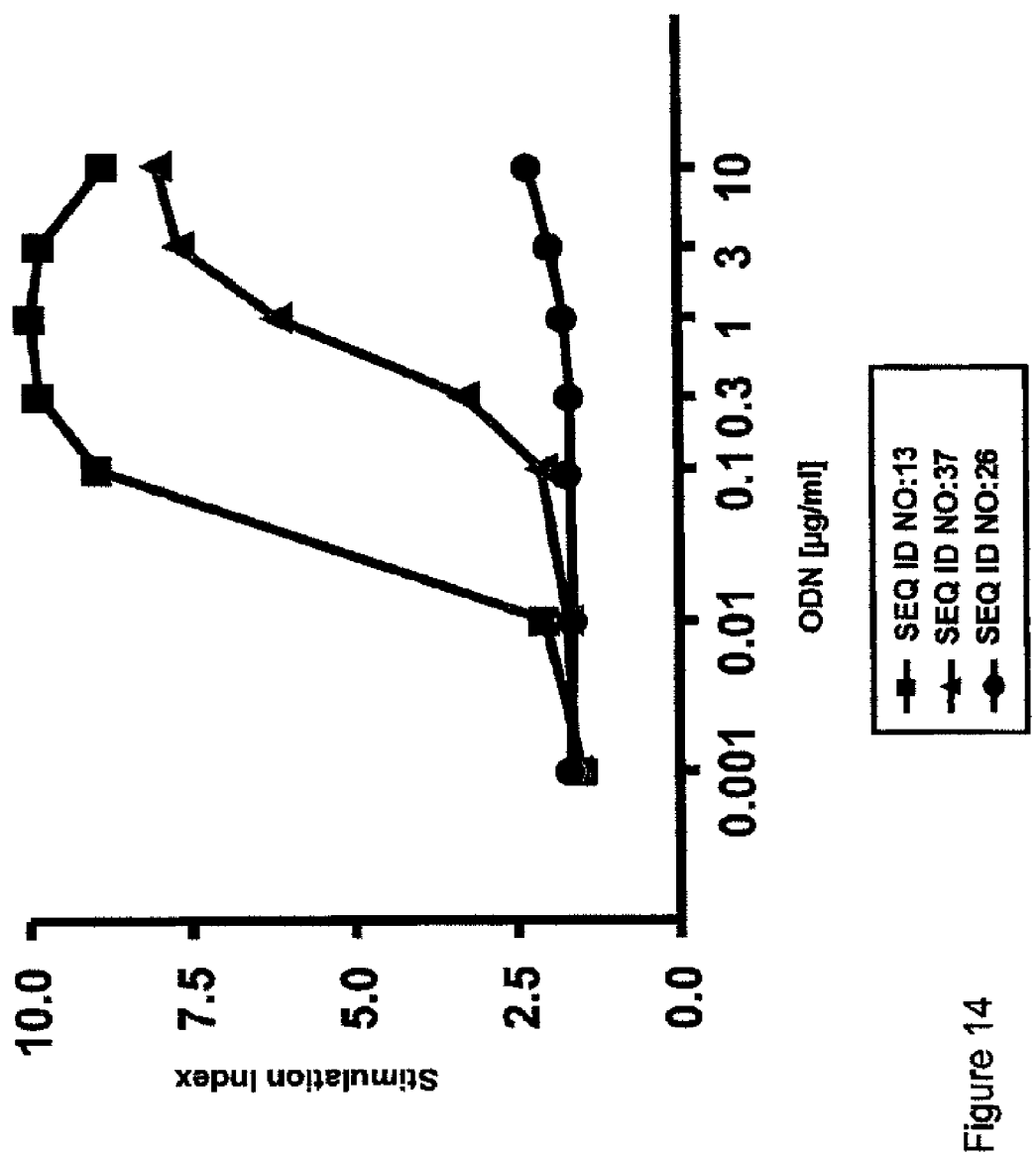
FIG. 14 is a graph showing the results of FACS analysis of B cell proliferation. CFSE stained BALB/c mouse splenocytes ($4\times10^5$/well) were incubated with 0.001, 0.01, 0.1, 0.3, 1, 3 or 10 μg/ml of ODN. At 72 hours post incubation, cells were stained for CD19 and B-cell proliferation was determined by FACS followed by analysis by ModFit Software. The activities of a JU-modified B-class ODN (SEQ ID NO:13), an unmodified B-class ODN (SEQ ID NO:37), and a non-CpG negative control ODN (SEQ ID NO:26) were compared. The x-axis is ODN concentration in μg/ml and the y-axis is 1 to relative B cell proliferation.

ODN were then tested their ability to induce B coil proliferation in splenocytes. CFSE-stained BALD/c mouse splenocytes ($4 \times 10^5$/well) were incubated with 0.001, 0.01, 0.1, 0.3, 1, 3 or 10 µg/ml of the indicated ODN (FIG. 14). At 72 hours poet-incubation, cells were stained for cell surface marker CD19 and B-cell proliferation was determined by FACS followed by analysis by ModFit Software. As shown in FIG. 14, incubation with modified SEQ ID NO:13 resulted in a marked increase in B-cell proliferation. The increase was most pronounced even at lower ODN concentration.

Figure 15A:
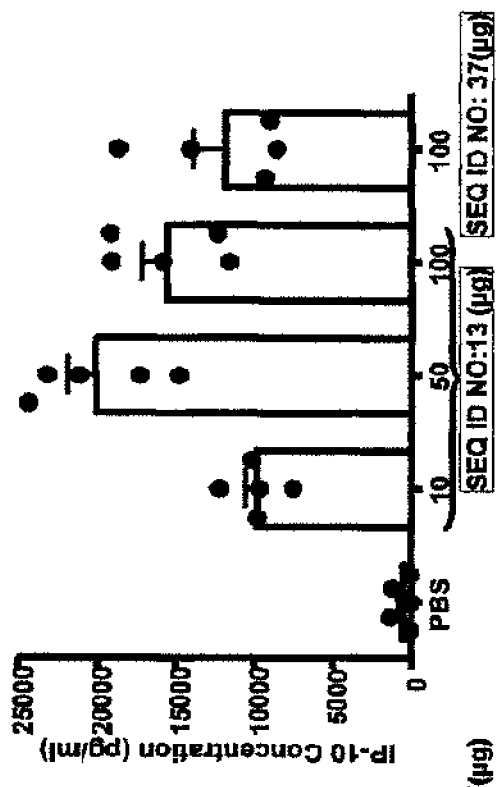
FIG. 15a shows TNF-alpha concentration and FIG. 15b shows IP-10 concentration. The x-axes are ODN dose in μg and the y-axes are cytokine concentration in pg/ml.
Figure 15B:
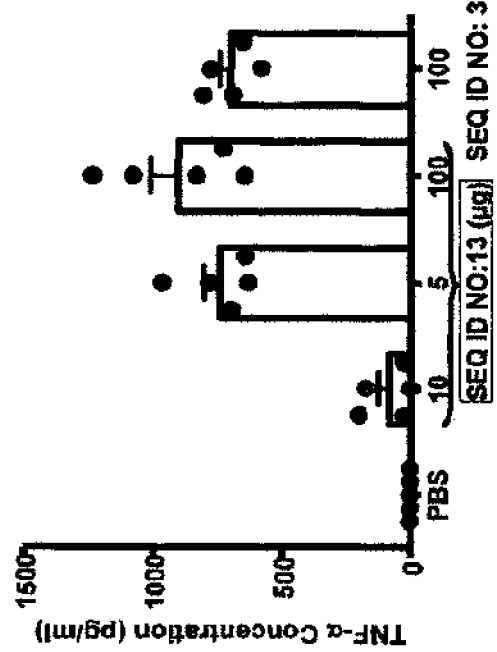
Figure 16:
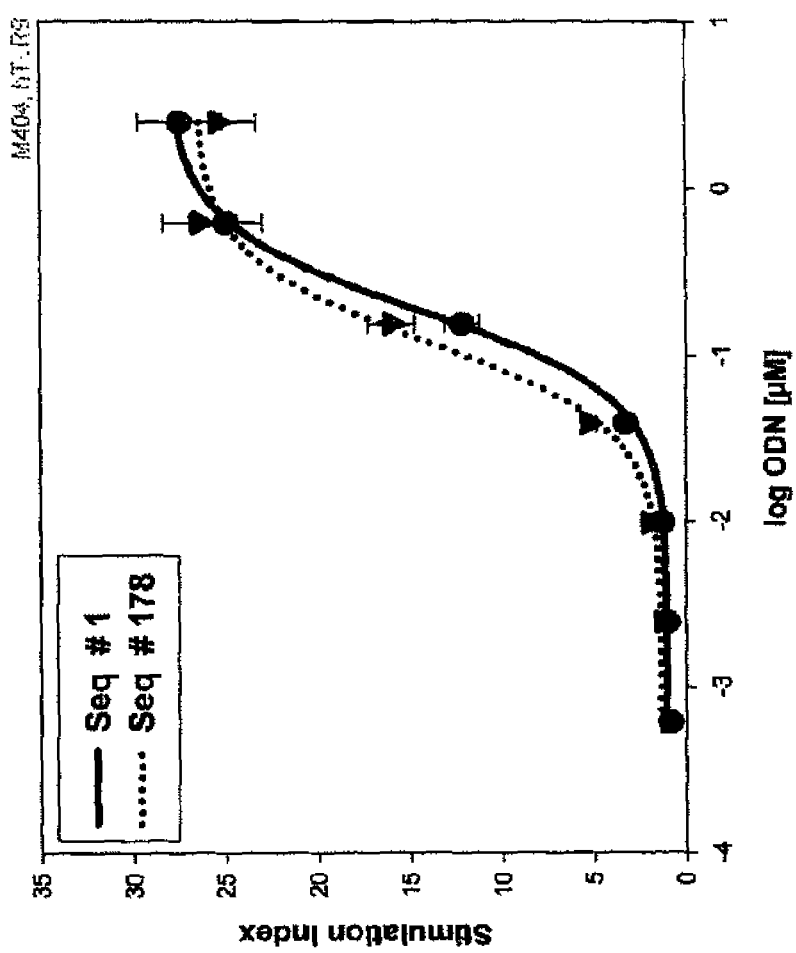
FIG. 16 is a graph showing TLR9-mediated NF-κB activation by a B-class ODN with a universal base (6-nitrobenzimidazol) (SEQ ID NO: 178) in place of thymidine in the parent sequence (SEQ ID NO: 1). hTLR9-LUC-293 cells were incubated with indicated amounts of nucleic acids and NF-κB activation was determined 16 h later by measuring luciferase activity. The x-axis is log ODN concentration in μM and the y-axis is IFN-α concentration in pg/ml.

To measure the effect of modified ODN in vivo, BALB/c mice (5 per group) were injected subcutaneously (SC) with 10, 50 or 100 µg of SEQ ID NO:13 or 100 µg of SEQ ID NO:37 in a total volume of 100 µl SC. Control group received 100 µl of PBS alone. Animals were bled by cardiac puncture at 1 hour post injection (TNF-alpha) or 3 hours post injection (IP-10). Plasma samples were assayed ELISA for TNF-alpha (FIG. 15a) and IP-10 (FIG. 15b). Injection of BALB/c mice with modified SEQ ID NO:13 resulted in higher TNF-alpha and IP-10 production than the non-modified SEQ ID NO:37, demonstrating that the lipophilic base shape substituted ODN of the invention result in greater immune stimulation in vivo than unmodified immune stimulatory ODN.

TABLE 5

Oligonucleotides tested in vivo

| Seq ID No. | Sequence | Modification |
|---|---|---|
| 13 | T*G*JU\*C-G*T*T*T*T*T*T*T*T*T*T*T*T*T*T | 5'JU derivative of SEQ ID NO: 1 |
| 37 | T*C*G*T*C*G*T*T*T*T*T*C*G*G*T*C*G*T*T*T*T | Unmodified B class |
| 26 | T*G*C*T*G*C*T*T*T*T*G*T*G*C*T*T*T*T*G*T*G*C*T*T | Non CpG control |

*phosphorothioate internucleotide linkage
-phosphodiester internucleotide linkage Example 7

Oligonucleotides with Additional Modification

ODN with lipophilic base analogs were tested for their ability to induce TLR9-mediated NF-κB activity in a luciferase assay (see materials and methods). FIGS. 16-23 show the activity of ODN with additional modifications (see table 6).

Figure 17:
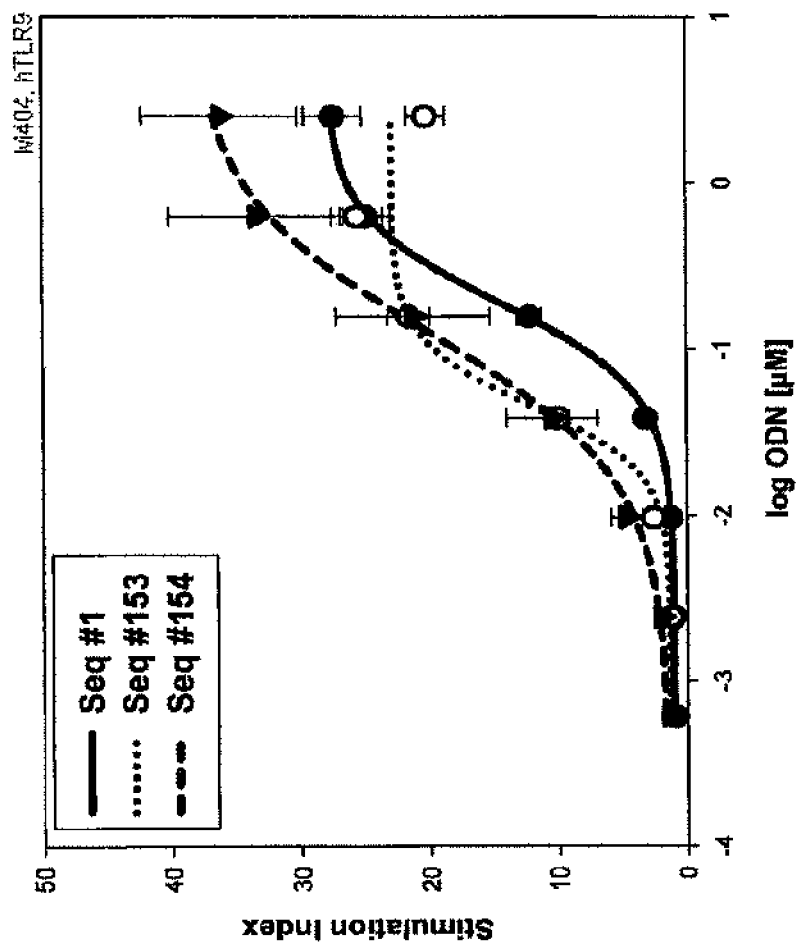
FIG. 17 is a graph showing TLR9-mediated NF-κB activation by B-class ODN with 5-(2-bromovinyl)-uridine (SEQ ID NO:153 and 154) in place of thymine in the parent sequence (SEQ ID NO:1). hTLR9-LUC-293 cells were incubated with indicated amounts of nucleic acids and NF-κB activation was determined 16 h later by measuring luciferase activity. The x-axis is log of ODN concentration in μM and the y-axis is IFN-α concentration in pg/ml.
Figure 21:
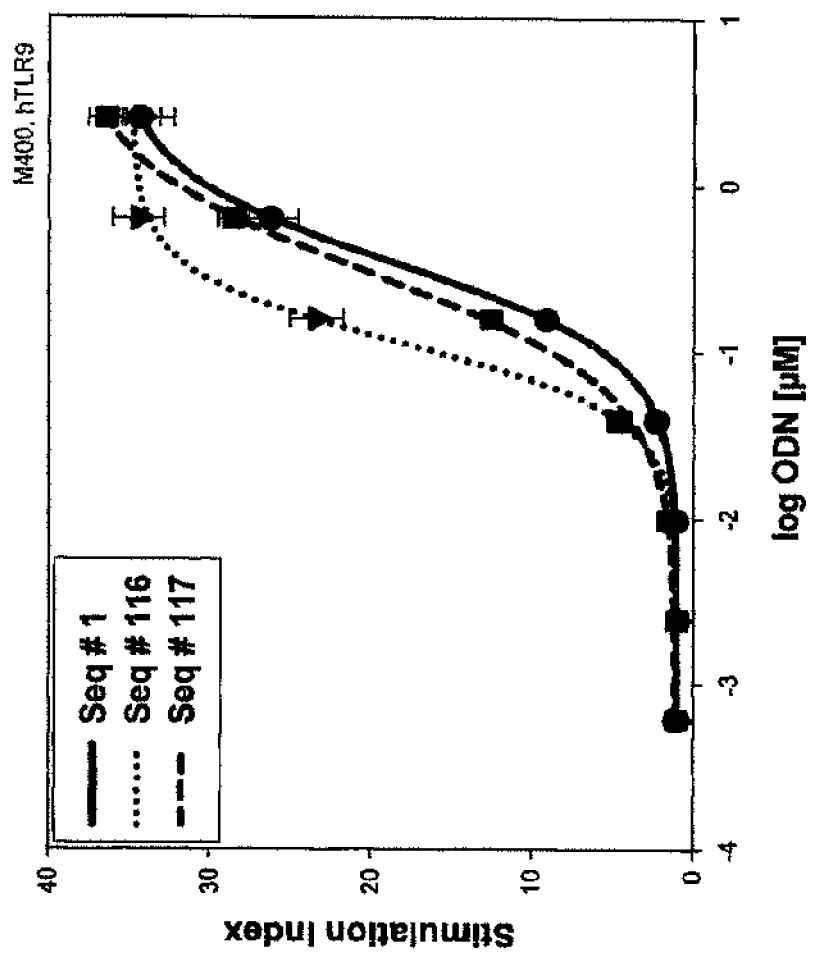
FIG. 21 is a graph showing TLR9-mediated NF-κB activation by two B-class ODN with 5-proynyl-dU (SEQ ID NO:116 and 117) in place of thymine of the parent sequence (SEQ ID NO:1). hTLR9-LUC-293 cells wee incubated with indicated amounts of nucleic acids and NF-κB activation was determined 16 h later by measuring luciferase activity. The x-axis is log of ODN concentration in μM and the y-axis is IFN-α concentration in pg/ml.

In order to test the activity of other base analogs, the activity of 6-nitro-benzimidazol (6NB)-modified ODN SEQ ID NO:178 and unmodified parent sequence SEQ ID NO:1 was compared. As shown in FIG. 12, SEQ ID NO:178 was able to activate TLR9-mediated NF-κB to a degree comparable with the unmodified parent sequence. Neat the activity of 5-(2-bromovinyl)-uridine modified ODN (SEQ ID NO:153-154) was compared to that of unmodified parent sequence SEQ ID NO:1. As shown in FIG. 17, both modified ODN were more active in the assay than the parent sequence. Next the activity of two B-class ODN with 5-proynyl-dU (SEQ ID NO:116 and 117) in place of thymidine of the parent sequence (SEQ ID NO:1). As shown in FIG. 21, both modified ODN had activity comparable to that of the parent sequence. The activity of SEQ ID NO:116, in which the modification is 5' to the CG dinucleotide, was slightly improved over the parent sequence.

Figure 18:
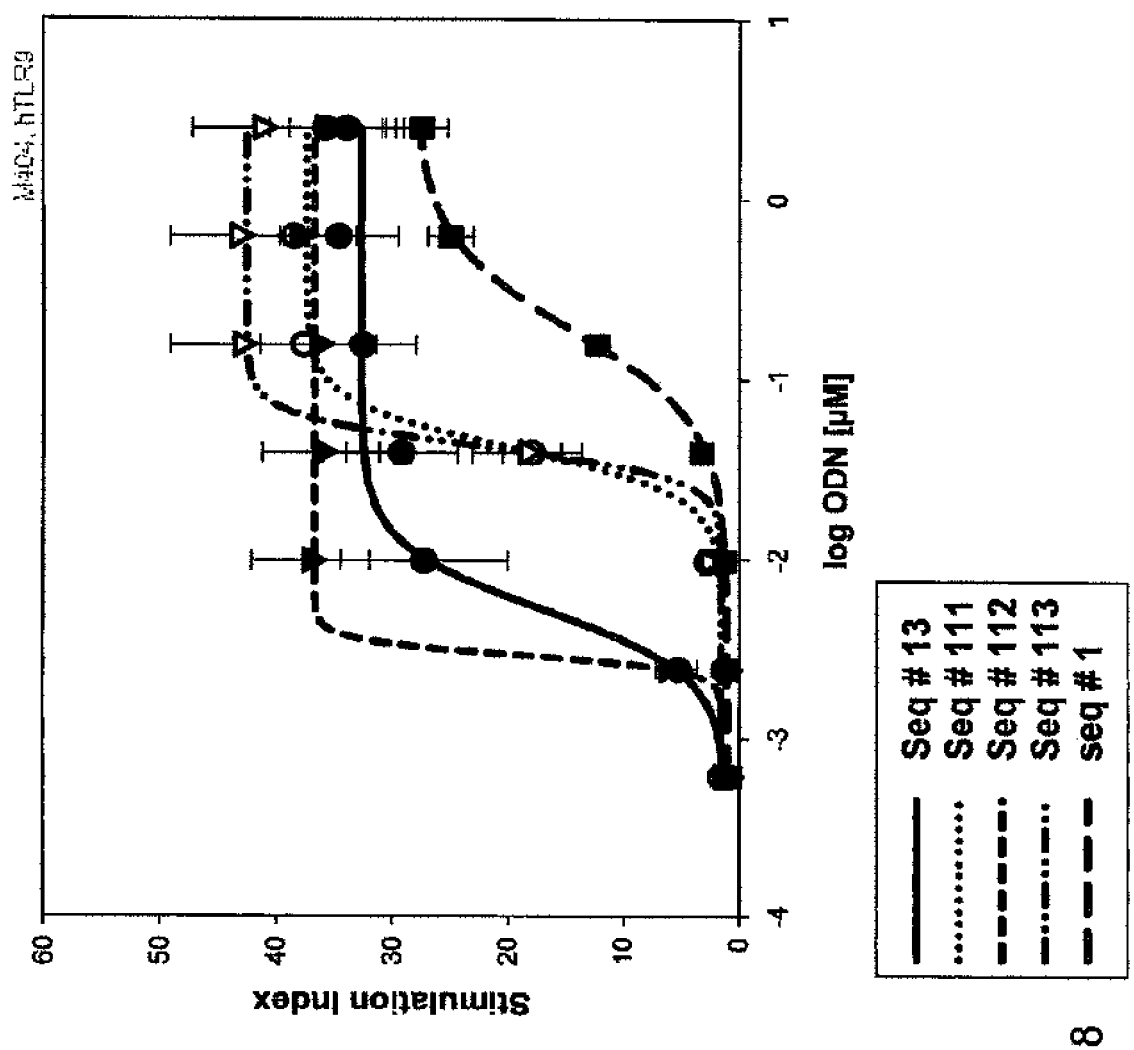
FIG. 18 is a graph showing TLR9-mediated NF-κB activation by B-class ODN with a sugar modification (2'-O-methylguanosine) in addition to a lipophilic substituted nucleotide analog (SEQ ID NO:111-113). The activity of these ODN was compared to that of the parent sequence (SEQ ID NO:1) and the same sequence with a lipophilic substituted nucleotide analog only (SEQ ID NO:13). hTLR9-LUC-293 cells were incubated with indicated amounts of nucleic acids and NF-κB activation was determined 16 h later by measuring luciferase activity. The x-axis is log of ODN concentration in μM and the y-axis is IFN-α concentration in pg/ml.

In order to test the effect of a second type of modification on JU-modified ODN, 2'O-methylguanosines were incorporated into JU-modified ODN. The activity of 2'-O-methylguanosine/JU ODN SEQ ID NO:111-113 was compared to that of parent SEQ ID NO:1 and JU only modified SEQ ID NO:13. As shown in FIG. 18, all JU-modified ODN were more active than the parent ODN. ODN with the 2'O-methylguanosine modification 3' of the CG dinucleotide (SEQ ID NO:112-113) were slightly more active than the ODN with the 2'O-methylguanosine modification 5' of the CG dinucleotide (SEQ ID NO:111) or the ODN modified with JU alone (SEQ ID NO:13).

Figure 19:
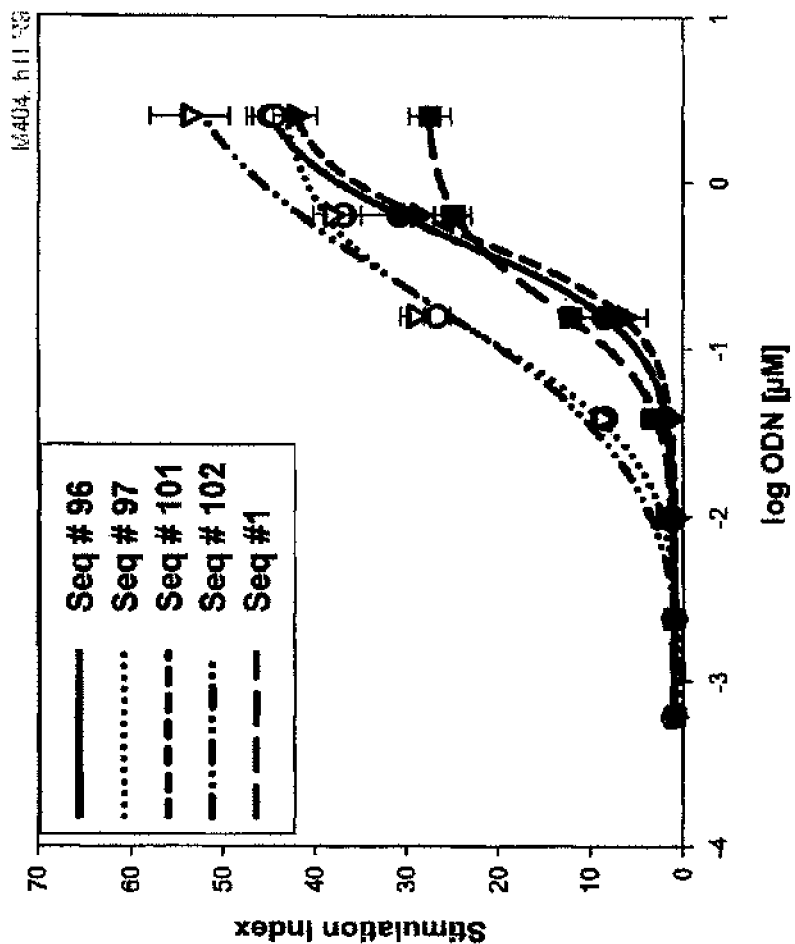
FIG. 19 is a graph showing TLR9-mediated NF-κB activation by branched B-class ODN with multiple 5' accessible ends. The activity of the ranched ODN (SEQ ID NO:96, 97, 101, and 102) was compared to that of SEQ ID NO:1. hTLR9-LUC-293 to cells were incubated with indicated amounts of nucleic acids and NF-κB activation was determined 16 h later by measuring luciferase activity. The x-axis is log of ODN concentration in μM and the y-axis is IFN-α concentration in pg/ml.

Next the activity of the JU-modified branched ODN (SEQ ID NO:96, 97, 101, and 102) was compared to that of SEQ ID NO:1. As shown in FIG. 19, the branched ODN with two accessible 5' ends were all as active or more active than the unmodified SEQ ID NO:1 in the assay. SEQ ID NO:101 and 102, with the trithylenglycol phosphate spacer, were more active than SEQ ID NO:96 AND 97 with the 3'-O-Methyl-G spacer.

Figure 20:
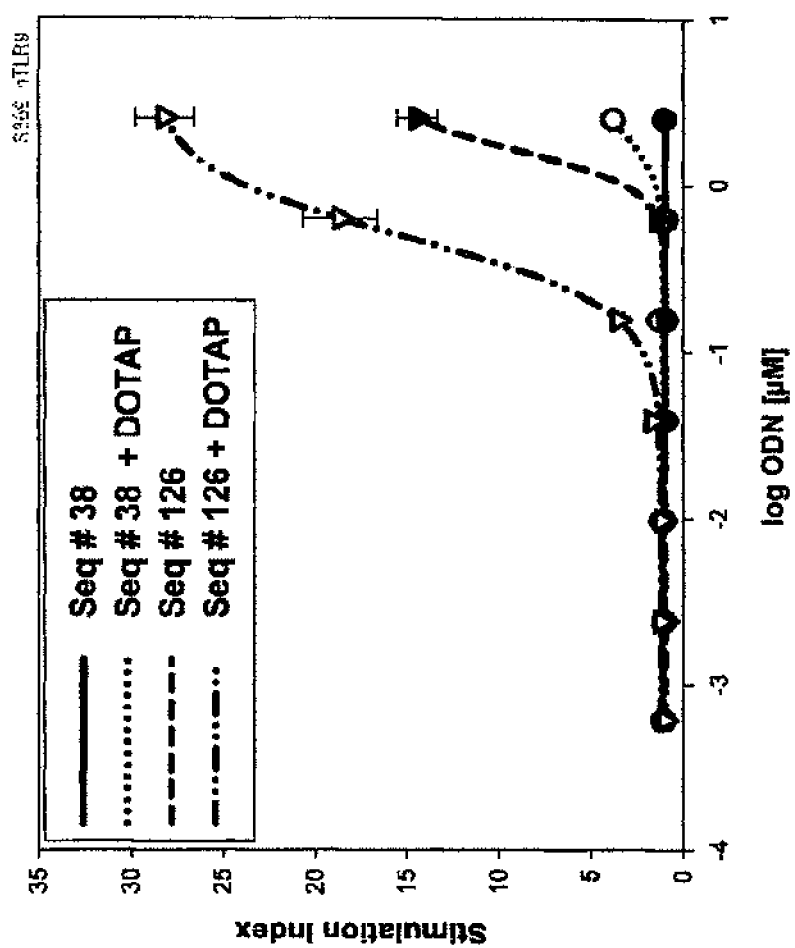
FIG. 20 is a graph showing TLR9-mediated NF-κB activation by a short unmodified B-class ODN (SEQ ID NO:38) and an ODN of the same sequence with a lipophilic substituted nucleotide analog and a lipophilic 3' tag (SEQ ID NO:126). Both we formulated with and without DOTAP. hTLR9-LUC-293 cells were incubated with indicated amounts of nucleic acids and NF-κB activation was determined 16 h later by measuring luciferase activity. The x-axis is log of ODN concentration in μM and the y-axis is IFN-α concentration in pg/ml.

Next the activity of a short unmodified B-class ODN (SEQ ID NO:38) and an ODN of the same sequence with a lipophilic substituted nucleotide analog and a lipophilic 3' tag (SEQ ID NO:126) was compared. Both were formulated with and without DOTAP. As shown in FIG. 20, the addition of the JU-modification and the lipophilic tag greatly enhanced the activity of the ODN, as did the addition of DOTAP.

Figure 22:
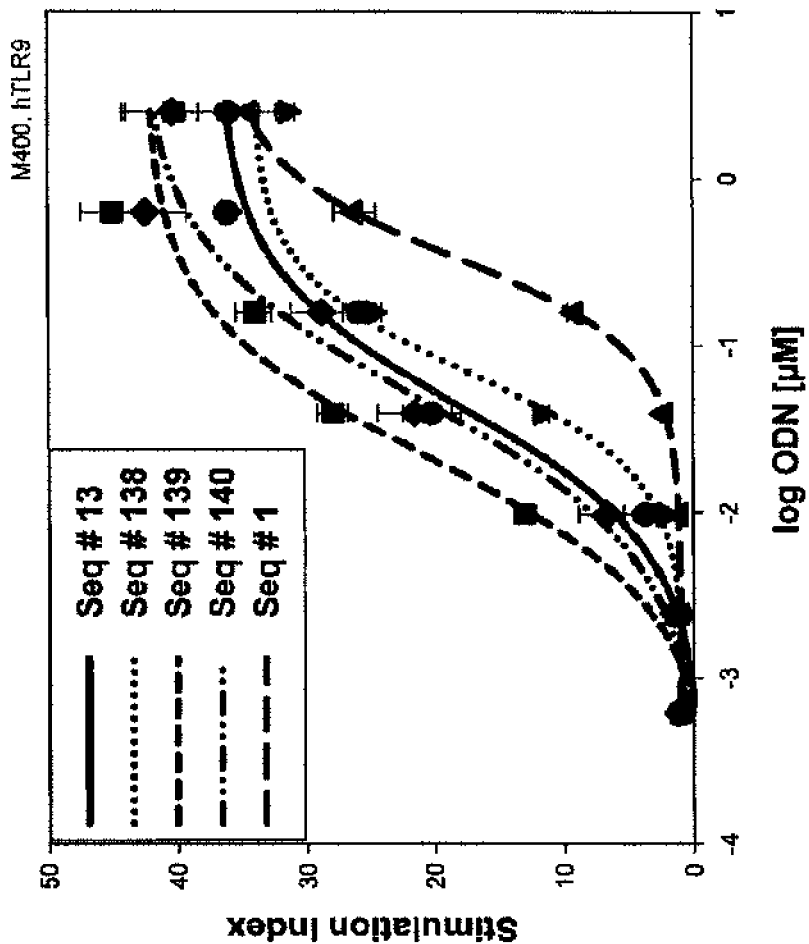
FIG. 22 is a graph showing hTLR9-mediated NF-κB activation by B-class ODN with a second nucleotide analog in addition to a lipophilic substituted nucleotide analog (SEQ ID NO:138, 7-deaza-dG; SEQ ID NO:139, inosine SEQ ID NO:140, 5-methyl-dC). The activity of the ODN was compared to that of the parent sequence (SEQ ID NO:1) and the same sequence with a lipophilic substituted nucleotide analog only (SEQ ID NO:13). hTLR9-LUC-293 cells were incubated with indicated amounts of nucleic acids and NF-κB activation was determined 16 h later by measuring luciferase activity. The x-axis is log of ODN concentration in μM and the y-axis is IFN-α concentration in pg/ml.
Figure 23:
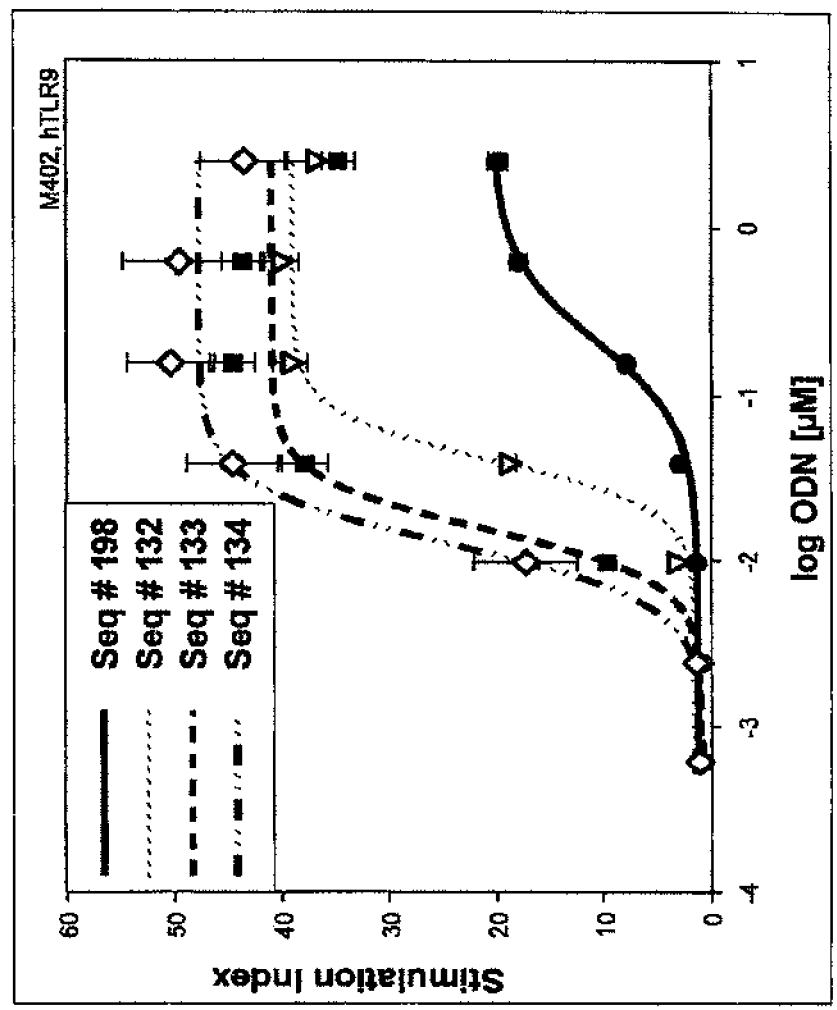
FIG. 23 is a graph showing hTLR9-mediated NF-κB activation by T-class ODN with a lipophilic substituted nucleotide analog (SEQ ID NO:132-134). The activity of these was compared to that of an immunostimulatory C-class ODN (SEQ ID NO:198). hTLR9-LUC-293 cells were incubated with indicated amounts of nucleic acids and NF-κB activation was determined 16 h later by measuring luciferase activity. The x-axis is log of ODN concentration in μM and the y-axis is IFN-α concentration in pg/ml.

Next the activity of B-lass ODN with a second nucleotide analog in addition to a lipophilic substituted nucleotide analog (SEQ ID NO:138, 7-deaza-dG; SEQ ID NO:139, inosine; SEQ ID NO:140, 5-methyl-dC) was compared to that of the parent sequence (SEQ ID NO:1) and the same sequence with a lipophilic substituted nucleotide analog only (SEQ ID NO:13). As shown in FIG. 22, all modified ODN were more active in the assay than the parent ODN Next the activity of T-class ODN with a lipophilic substituted nucleotide analog (SEQ ID NO:132-134) was compared to that of a C-class ODN (SEQ ID NO:198) so known to be immunostimulatory. As shown in FIG. 23, all modified ODN showed much greater activity in the assay than the unmodified C-class ODN.

TABLE 6

Lipophilic substituted oligonucleotides with additional modifications

| Seq ID No. | Sequence | Type and modification |
|---|---|---|
| 1 | T*G*T*C-G*T*T*T*T*T*T*T*T*T*T*T*T*T*T*T | unmodified B-class |
| 13 | T*G*JU\*C-G*T*T*T*T*T*T*T*T*T*T*T*T*T*T | B-class: 5'JU derivative of SEQ ID NO: 1 |
| 38 | G*T*C-G*T*T | Unmodified B-class |
| 95 | (T*G*JU\*C-G*T*T*L*)2doub-3mG | 3'3-branched |
| 97 | (JU\*C*G*T*T*C*G*L*)2doub-3mG | 3'3-branched |
| 101 | (T*G*JU\*C-G*T*T*L*)2doub-teg | 3'3-branched |
| 102 | (JU\*C*G*T*T*C*G*L*)2doub-teg | 3'3-branched |
| 111 | T***mG*JU**\*C-G*T*T*T*T*T*T*T*T*T*T*T*T*T*T | 2-O-methyl-modified B-class |

TABLE 6-continued

Lipophilic substituted oligonucleotides with additional modifications

| Seq ID No. | Sequence | Type and modification |
|---|---|---|
| 112 | T*G*JU*C-mG*T*T*T*T*T*T*T*T*T*T*T*T*T*T*T | 2'O-methyl-modified B-class |
| 113 | T*mG*JU*C-mG*T*T*T*T*T*T*T*T*T*T*T*T*T*T*T | 2'-O-methyl-modified B-class |
| 116 | T*G*PU*C-G*T*T*T*T*T*T*T*T*T*T*T*T*T*T*T | B-class with 5-proynyl-dU (PU) |
| 117 | T*G*T*C-G*PU*T*T*T*T*T*T*T*T*T*T*T*T*T*T | B-class with 5-proynyl-dU (PU) |
| 126 | G*JU*C-G*JU*T-hex | B-class derivative of 38 with JU and hexadecylglyceryl 3' tag |
| 132 | JU*C*T*T*T*T*T*T*T*T*C*G*T*T*T*T*T*T*T*T*T | T-class |
| 133 | T*C*T*T*T*T*T*T*T*JU*C*G*T*T*T*T*T*T*T*T*T | T-class |
| 134 | JU*C*T*T*T*T*T*T*T*JU*C*G*T*T*T*T*T*T*T*T*T | T-class |
| 138 | T*G*JU*C-E*T*T*T*T*T*T*T*T*T*T*T*T*T*T*T | B-class with 7-deaza-dG (E) |
| 139 | T*G*JU*C-I*T*T*T*T*T*T*T*T*T*T*T*T*T*T*T | B-class withe Inosine (I) |
| 140 | T*G*JU*Z-G*T*T*T*T*T*T*T*T*T*T*T*T*T*T*T | B-class withe 5-methyl-dC (Z) |
| 153 | T*G*BVU*C-G*T*T*T*T*T*T*T*T*T*T*T*T*T*T*T | B-class with 5-(2-bromo-vinyl)-uridine (BVU) |
| 154 | T*G*T*C-G*BVU*T*T*T*T*T*T*T*T*T*T*T*T*T*T | B-class with 5-(2-bromo-vinyl)-uridine (BVU) |
| 178 | T*G*6NB*C-G*T*T*T*T*T*T*T*T*T*T*T*T*T*T*T | B-class with 6-nitro-benzimidazol (6NB) |
| 198 | C*G*G*C*G*C*C*T*C*G | C-class |

*phosphorothioate internucleotide linkage
-phosphodiester internucleotide linkage Example 8

Activity of Modified P-Class Oligonucleotides

Figure 24:
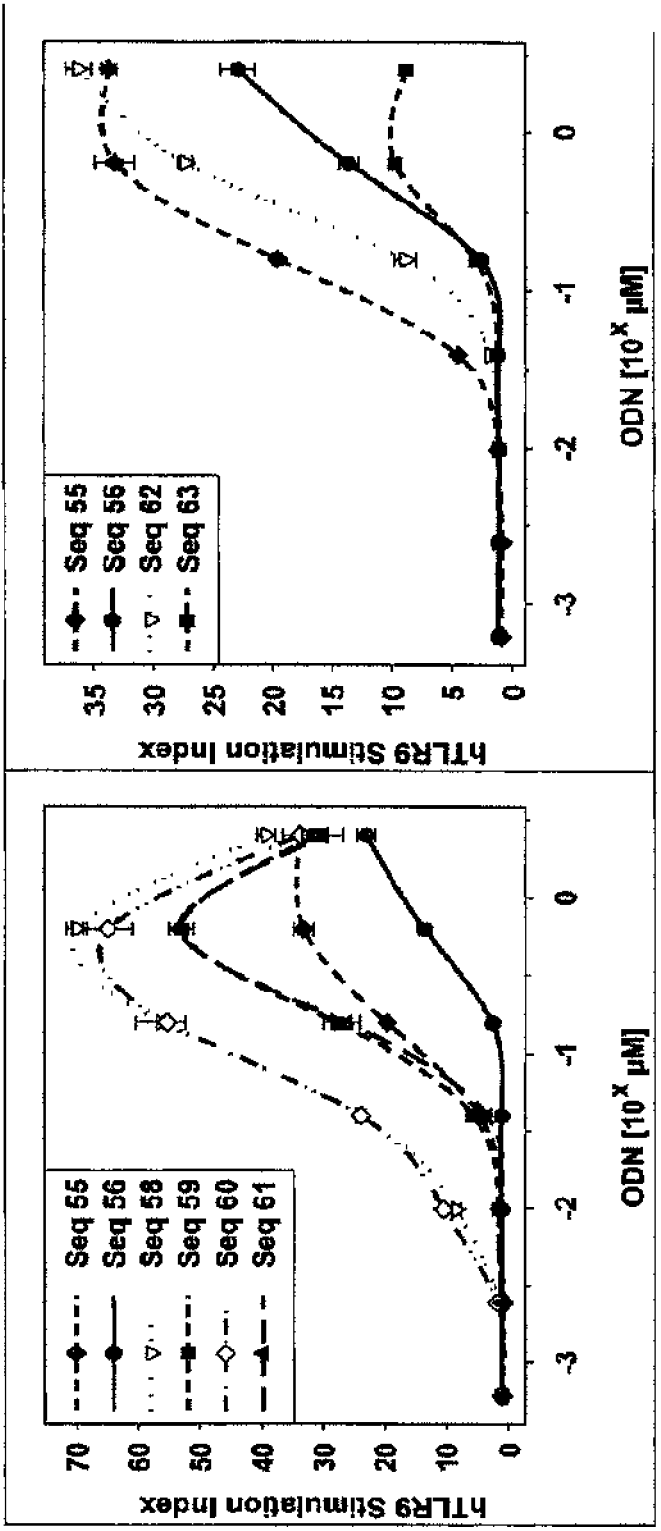
FIG. 24 is two graphs showing hTLR9-mediated NF-κB activation by P-class ODN with a lipophilic substituted nucleotide analog (SEQ ID NO:58-63).

P-class ODN with lipophilic base analogs were tested for the ability to activate the NF-κB pathway through TLR9 as measured by luciferase assay. The activity of P-class ODN with a lipophilic substituted nucleotide analog (SEQ ID NO:58-61) was compared to that of a B-class positive control (SEQ ID NO:55) and an unmodified P-class ODN (SEQ ID NO:56). As shown in FIG. 24, all modified P-class ODN showed increased TLR9 stimulation compared to the controls. FIG. 24a shows JU-modified P-class ODN and 24b shows EU-modified P-class ODN.

Figure 25:
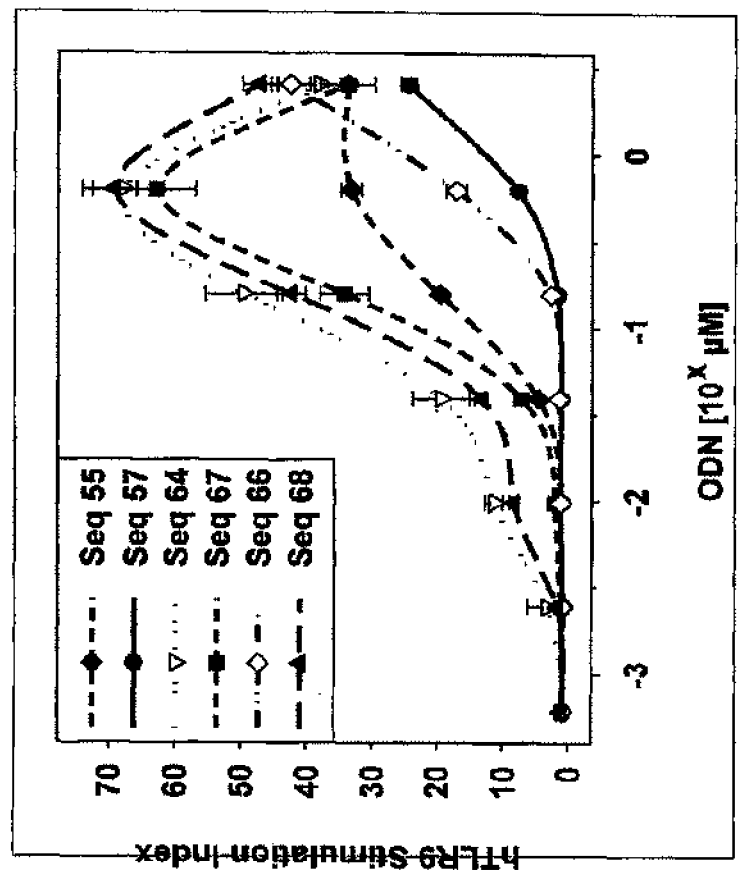
FIG. 25 is a graph showing hTLR9-mediated NF-κB activation by P-class ODN with a lipophilic substituted nucleotide analog (SEQ ID NO:64, 66-67). The activity of these is compared to that of a B-class positive control (SEQ ID NO:55), a C-class ODN (SEQ ID NO:68) and an unmodified P-class ODN (SEQ ID NO:57). hTLR9-LUC-293 cells were incubated with indicated amounts of nucleic acids and NF-κB activation was determined 16 h later by measuring luciferase activity. The x-axis is log of ODN concentration in μM and the y-axis is the relative stimulation index.

Next the activity of modified P-class ODN (SEQ ID NO:64 (EU-modified), 66-67 (JU-modified) was compared to that of a B-class positive control (SEQ ID NO:55), a C-class ODN (SEQ ID NO:68) and an unmodified P-class ODN (SEQ ID NO:57). As shown in FIG. 25, all modified ODN showed a higher degree of TLR9 stimulation than the unmodified P class ODN. SEQ ID NO:66, with the phosphodiester bond in the CG dinucleotide, showed reduced activity compared to the fully phosphorothioate SEQ ID NO:67.

Next the modified P-class ODN were tested for their ability to induce expression of IFN-alpha. The activity of P-class ODN with a lipophilic substituted nucleotide analog (SEQ ID NO:58-61) was compared to that of a B-class positive control (SEQ ID NO:55) and an unmodified P-class ODN (SEQ ID NO:56) as measured by an ELISA assay. As shown in FIG. 26, all modified P-class ODN showed a increase in IFN-alpha induction. FIG. 26a shows JU-modified P-class ODN and 26b shows EU-modified P-class ODN.

Figure 27:
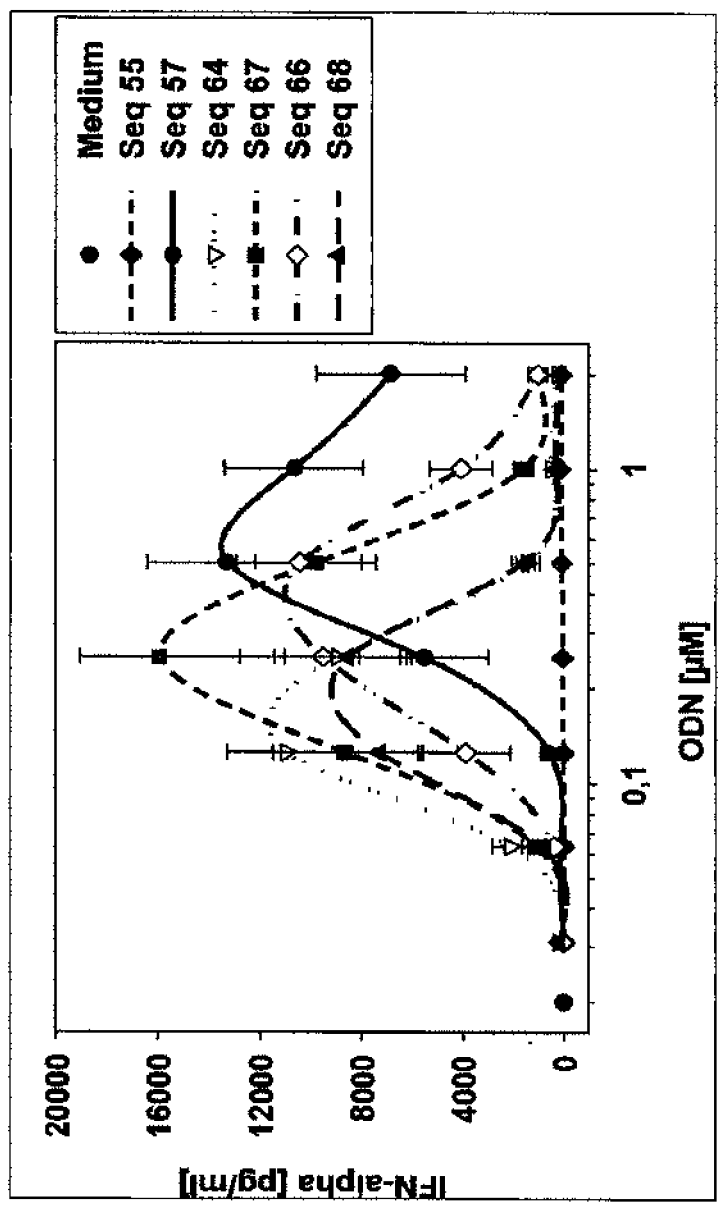
FIG. 27 is a graph showing induction of IFN-α by P-class ODN with a lipophilic substituted nucleotide analog (SEQ ID NO:64, 66-67). The activity of these is compared to that of a B-class positive control (SEQ ID NO:55), a C-class ODN (SEQ ID NO:68) and an unmodified P-class ODN (SEQ ID NO:57). Human PBMC were incubated with the indicated ODN for 48 hours. IFN-α was then determined in the cell culture supernatants by ELISA. The x-axes are ODN concentration in μM and the y-axes are IFN-α concentration in pg/ml.

Next the modified P-class ODN (EU-modified), 66-67 (JU-modified) was compared to that of a B-class positive control (SEQ ID NO:55), a C-class ODN (SEQ ID NO:68) and an unmodified P-class ODN (SEQ ID NO:57) for the ability to induce IFN-alpha as measured by an ELISA assay. As shown in FIG. 27, the modified P-class ODN showed enhanced ability to induce IFN-alpha. As in FIG. 24. SEQ ID NO:66 showed reduced activity compared to SEQ ID NO:67.

Next the modified P-class ODN were tested for the ability to induce IL-6 in human PBMC. PBMC from three donors were incubated with ODN at concentrations as indicated for 24 h, followed by luminex 25-plex analysis of the supernatants for IL-6. The activity of modified P-class ODN (SEQ ID NO:58, 60-62, FIG. 28a) (SEQ ID NO:64 and 67, FIG. 28b) was compared to that of an unmodified B-class ODN (SEQ ID NO:55), and unmodified C-class ODN (SEQ ID NO:54), a negative control ODN (SEQ ID NO:53), and an unmodified P-class ODN (SEQ ID NO:56). The JU-modified ODN (SEQ ID NO:58, 60-61 and 67) showed a slightly higher activation of IL-6 than did the EU-modified ODN (SEQ ID NO:62 and 64). All modified ODN showed increased activity compared to unmodified ODN.

Figure 29B:
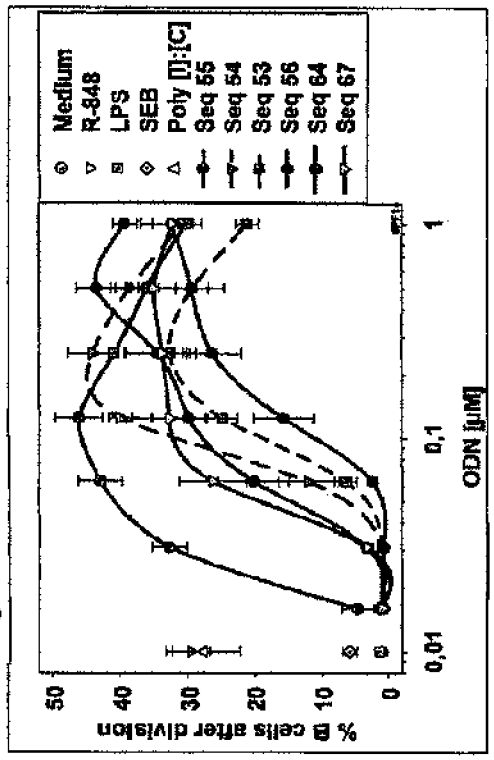
FIG. 29 is two graphs showing B-cell proliferation after treatment with P-class class ODN with a lipophilic substituted nucleotide analog (SEQ ID NO:58, 60-62, FIG. 29a) (SEQ ID NO:64 and 67, FIG. 29b). The activity was compared to that of an unmodified B-class ODN (SEQ ID NO:55), an unmodified C-class ODN (SEQ ID NO:54), a negative control ODN (SEQ ID NO:53), an unmodified P-class ODN (SEQ ID NO:56), LPS, R-848, SEB, and a poly[I]:[C] ODN. CFSE-labeled PBMC from three donors were incubated with the ODN for 5 days and then stained with a CD19 antibody. The percentage of B cells with reduced CFSE staining was determined. The x-axes are ODN concentration in μM and the y-axes are % of B cells with reduced staining aftr division.
Figure 29A:
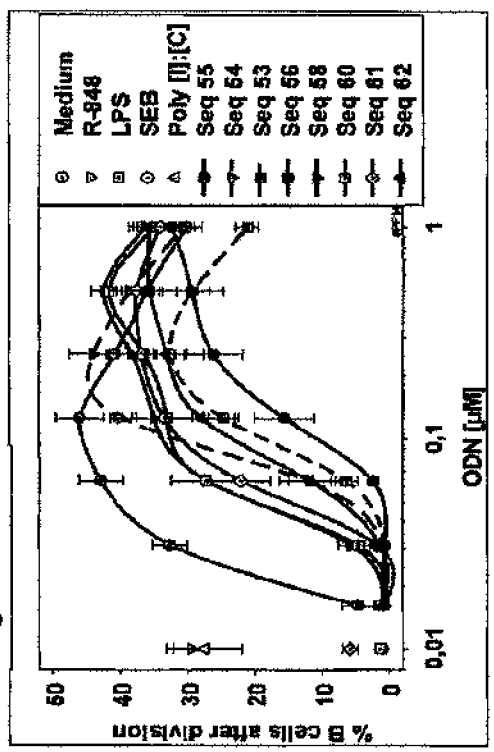

Next the activity of modified P-class class ODN (SEQ ID NO:58, 60-62, FIG. 29a) (SEQ ID NO:64 and 67, FIG. 29b) was compared to that of an unmodified B-class ODN (SEQ ID NO:55), an unmodified C-class ODN (SEQ ID NO:54), a negative control ODN (SEQ ID NO:53), an unmodified P-class ODN (SEQ ID NO:56), LPS, R-848, SEB, and a poly[I]:[C] ODN. CFSE-labeled PBMC from three donors were incubated with the ODN for 5 days and then stained with a CD19 antibody. The percentage of B cells with reduced CFSE staining was determined. Treatment with the B-class ODN resulted in the highest percentage of B cells after division. Treatment with the JU-modified ODN resulted in a higher percentage of B cells than the BU-modified ODN.

Figure 30:
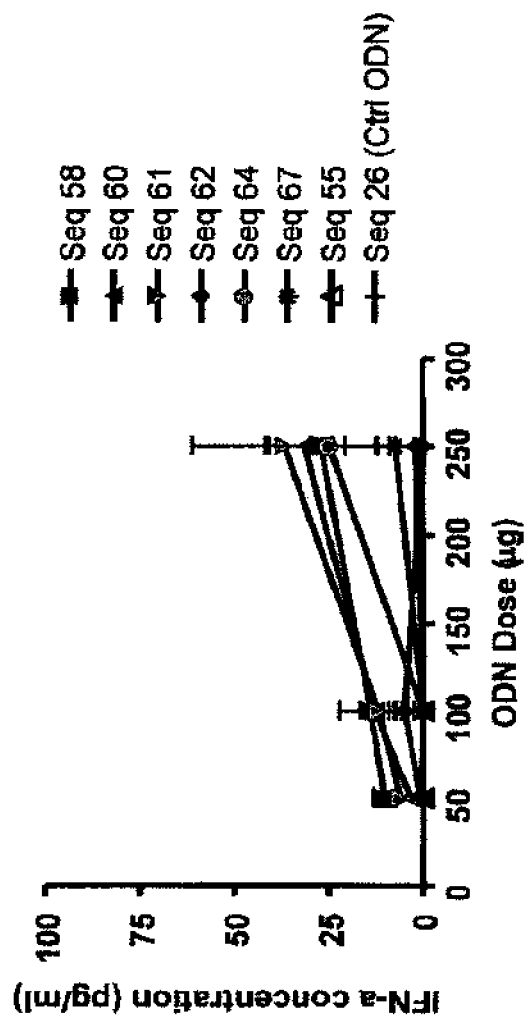
FIG. 30 is a graph showing induction of murine IFN-α by P-class ODN with a lipophilic substituted nucleotide analog (SEQ ID NO:58, 60-62, 64, and 67). The activity of these is compared to that of a B-class positive control (SEQ ID NO:55) and a negative control (SEQ ID NO:26). BALB/c mice (5 per group) were injected SC with differing doses of ODN. Animals were bled at 3 hr post injection and plasma tested for IFN-alpha by ELISA. The x axis is ODN dose in μg and the y-axis is IFN-α concentration in pg/ml.

In order to determine the effect of the modified P-class ODN in vivo, BALB/c to mice (5 per group) were injected SC with differing doses of ODN. Animals were bled at 3 hr post injection and plasma tested for IFN-alpha by ELISA. The activity of modified P-class ODN (SEQ ID NO:58, 60-62, 64, and 67) was compared to that of a B-class negative control (SEQ ID NO:55) and a negative control (SEQ ID NO:26). As shown in FIG. 30, treatment with the JU-modified ODN SEQ NO:58, 60, and 61 resulted in slightly higher IFN-alpha induction than the EU-modified ODN SEQ ID NO:64. The B-class ODN SEQ ID NO:55 did not induce much murine IFN-alpha, as expected.

Next the modified P-class ODN were evaluated for their ability to reduce tumor volume mouse SAIN tumor model. Female A/J mice (10 per group) were injected SC with 5×10⁵ SaI/N tumor cells on day 0. Mice were treated with 35 μg (FIG. 31a) or 100 μg (FIG. 31b) P-class ODN with a lipophilic substituted nucleotide analog (SEQ ID NO:60, 64, and 67), an unmodified C-class ODN, an unmodified B-class ODN (SEQ ID NO:55), or PBS alone. ODN were given SC once weekly starting on day 8 post tumor induction. Animals were monitored for survival and tumor volume. As shown in FIG. 31a, at the lower dosage treatment with the modified P-class ODN showed the greatest reduction in tumor volume, suggesting that these ODN would be effective in treating cancer. At the higher dosage in 31b, all modified P-class ODN and the C-class ODN were effective in reducing tumor volume.

TABLE 7

Modified P-class oligonucleotides

| Seq ID No. | Sequence | Type and modification |
|---|---|---|
| 53 | T*C*C*A*G*G*A*C*T*T*C*T*C*T*C*A*G*G*T*T | neg control |
| 54 | T*C*G*T*C*G*T*T*T*T*C*G*G*C*G*C*G*C*G*C*C*G | C-class |
| 55 | T*C*G*T*C*G*T*T*T*T*G*T*C*G*T*T*T*T*G*T*C*G*T*T | B-class |
| 56 | T*C-G*A*C*G*T*C*G*A*T*C*G*G*C*G*C*G*C*G*C*C*G | P-class T->A, 5' CpG PO |
| 57 | T*C-G*T*C*G*A*C*G*A*T*C*G*G*C*G*G*C*C*G*C*C*G | P-class 3' palindrome, 5' CpG PO |
| 58 | JU*C-G*A*C*G*T*C*G*A*T*C*G*G*C*G*C*G*C*G*C*C*G | P-class |
| 59 | JU*C*G*A*C*G*T*C*G*A*T*C*G*G*C*G*C*G*C*G*C*C*G | P-class |
| 60 | JU*C-G*A*C*G*T*C*G*A*T*C*G*G*C*G*C*G*C*G*C*C*G*T | P-class |
| 61 | JU*C*G*A*C*G*T*C*G*A*T*C*G*G*C*G*C*G*C*G*C*C*G*T | P-class |
| 62 | EU*C-G*A*C*G*T*C*G*A*T*C*G*G*C*G*C*G*C*G*C*C*G | P-class |
| 63 | EU*C-G*A*C*G*T*C*G*A*T*C*G*G*C*G*C*G*C*G*C*C*G | P-class |
| 64 | EU*C-G*A*C*G*T*C*G*A*T*C*G*G*C*G*C*G*C*G*C*C*G | P-class |
| 65 | EU*C*G*A*C*G*T*C*G*A*T*C*G*G*C*G*C*G*C*G*C*C*G | P-class |
| 66 | JU*C-G*T*C*G*A*C*G*A*T*C*G*G*C*G*G*C*C*G*C*C*G*T | P-class |
| 67 | JU*C*G*T*C*G*A*C*G*A*T*C*G*G*C*G*G*C*C*G*C*C*G*T | P-class |
| 68 | T*C_G*C_G*T*C_G*T*T*C_G*G*C*G*C_G*C*G*C*C*G | C-class |

*phosphorothioate internucleotide linkage
-phosphodiester internucleotide linkage A summary of Exemplary modified ODN is presented in Table 8:

TABLE 8

| Seq ID No# | Oligonucleotide sequence |
|---|---|
| 3 | T*G*FF*C-G*T*T*T*T*T*T*T*T*T*T*T*T*T*T*T*T |
| 4 | T*G*T*C-G*FF*T*T*T*T*T*T*T*T*T*T*T*T*T*T*T*T |
| 5 | T*G*FF*C-G*FF*T*T*T*T*T*T*T*T*T*T*T*T*T*T*T*T |

TABLE 8-continued

| Seq ID No# | Oligonucleotide sequence |
|---|---|
| 6 | T*G*T*FF-G*T*T*T*T*T*T*T*T*T*T*T*T*T*T*T |
| 7 | T*G*T*C-FF*T*T*T*T*T*T*T*T*T*T*T*T*T*T*T |
| 8 | T*FF*C-G*T*T*T*T*T*T*T*T*T*T*T*T*T*T*T |
| 9 | T*G*T*C-G*T*FFT*T*T*T*T*T*T*T*T*T*T*T*T |
| 10 | T*G*BUC-G*T*T*T*T*T*T*T*T*T*T*T*T*T*T*T |
| 11 | T*G*T*C-G*BUT*T*T*T*T*T*T*T*T*T*T*T*T*T |
| 12 | T*G*BUC-G*BUT*T*T*T*T*T*T*T*T*T*T*T*T*T |
| 13 | T*G*JUC-G*T*T*T*T*T*T*T*T*T*T*T*T*T*T*T |
| 14 | T*G*T*C-G*JUT*T*T*T*T*T*T*T*T*T*T*T*T*T |
| 15 | T*G*JUC-G*JUT*T*T*T*T*T*T*T*T*T*T*T*T*T |
| 16 | T*G*U*C-G*T*T*T*T*T*T*T*T*T*T*T*T*T*T*T |
| 17 | T*G*T*C-G*U*T*T*T*T*T*T*T*T*T*T*T*T*T*T |
| 18 | T*G*U*C-G*U*T*T*T*T*T*T*T*T*T*T*T*T*T*T |
| 19 | JUC*G*T*C*G*T*T*T*T*T*C*G*G*T*C*G*T*T*T*T |
| 20 | T*C*G*JUC*G*T*T*T*T*T*C*G*G*T*C*G*T*T*T*T |
| 21 | T*C*G*T*C*G*T*T*T*T*T*C*G*G*JUC*G*T*T*T*T |
| 22 | JUC*G*JUC*G*T*T*T*T*T*C*G*G*T*C*G*T*T*T*T |
| 23 | T*C*G*JUC*G*JUT*T*T*T*C*G*G*T*C*G*T*T*T*T |
| 24 | T*C*G*T*C*G*T*T*T*T*T*C*G*G*JUC*G*JUT*T*T*T |
| 27 | JUC*G*T*C*G*T*T*T*T*A*C*G*G*C*G*C*C*G*T*G*C*C*G |
| 28 | T*C*G*JUC-G*T*T*T*T*A*C*G*G*C*G*C*C*G*T*G*C*C*G |
| 29 | T*G*T*C-G*EUT*T*T*T*T*T*T*T*T*T*T*T*T*T |
| 30 | T*G*EUC-G*EUT*T*T*T*T*T*T*T*T*T*T*T*T*T |
| 31 | JUC-G*T*C*G*A*C*G*A*T*C*G*G*C*G*C*G*C*G*C*C*G |
| 32 | T*C*G*JUC-G*A*C*G*A*T*C*G*G*C*G*C*G*C*G*C*C*G |
| 33 | JUC-G*JUC*G*A*C*G*A*T*C*G*G*C*G*C*G*C*G*C*C*G |
| 34 | JUC-G-A-C-G-T-C-G-T-G-G*G*G |
| 35 | T*C-G-A-C-G-JU-C-G-T-G-G*G*G |
| 36 | T*C-G-A-C-G-JU-C-G-JU-G-G*G*G |
| 39 | G*JUC-G*T*T |
| 40 | G*JUC-G*JUT |
| 41 | T*G*CUC-G*T*T*T*T*T*T*T*T*T*T*T*T*T*T*T |
| 42 | T*G*EUC-G*T*T*T*T*T*T*T*T*T*T*T*T*T*T*T |
| 44 | JUC-G*JUC*G*T*T*T*T*A*C*G*G*C*G*C*C*G*T*G*C*C*G |
| 45 | T*C-G*JUC*G*JUT*T*T*A*C*G*G*C*G*C*C*G*T*G*C*C*G |
| 47 | T*C*T*T*T*T*T*G*JUC-G*T*T*T*T*T*T*T*T*T*T |
| 48 | T*C*T*T*T*T*T*G*JUC-G*JUT*T*T*T*T*T*T*T*T |
| 49 | JUC*T*T*T*T*T*T*G*T*C-G*T*T*T*T*T*T*T*T*T*T |
| 50 | JUC-T*T*T*T*T*T*G*T*C-G*T*T*T*T*T*T*T*T*T*T |

TABLE 8-continued

| Seq ID No# | Oligonucleotide sequence |
|---|---|
| 51 | T*C*T*T*T*T*T*T*G*U*C-G*T*T*T*T*T*T*T*T*T |
| 58 | JU\*C-G\*A\*C\*G\*T\*C\*G\*A\*T\*C\*G\*G\*C\*G\*C\*G\*C\*C\*G |
| 59 | JU\*C\*G\*A\*C\*G\*T\*C\*G\*A\*T\*C\*G\*G\*C\*G\*C\*G\*C\*C\*G |
| 60 | JU\*C-G\*A\*C\*G\*T\*C\*G\*A\*T\*C\*G\*G\*C\*G\*C\*G\*C\*C\*G\*T |
| 61 | JU\*C\*G\*A\*C\*G\*T\*C\*G\*A\*T\*C\*G\*G\*C\*G\*C\*G\*C\*C\*G\*T |
| 62 | EU\*C-G\*A\*C\*G\*T\*C\*G\*A\*T\*C\*G\*G\*C\*G\*C\*G\*C\*C\*G |
| 63 | EU\*C\*G\*A\*C\*G\*T\*C\*G\*A\*T\*C\*G\*G\*C\*G\*C\*G\*C\*C\*G |
| 64 | JU\*C-G\*T\*C\*G\*A\*C\*G\*A\*T\*C\*G\*G\*C\*G\*G\*C\*C\*G\*C\*C\*G\*T |
| 65 | JU\*C\*G\*T\*C\*G\*A\*C\*G\*A\*T\*C\*G\*G\*C\*G\*G\*C\*C\*G\*C\*C\*G\*T |
| 66 | EU\*C-G\*T\*C\*G\*A\*C\*G\*A\*T\*C\*G\*G\*C\*G\*G\*C\*C\*G\*C\*C\*G |
| 67 | JU\*C-G\*T\*C\*G\*A\*C\*G\*A\*T\*C\*G\*G\*C\*G\*G\*C\*C\*G\*C\*C\*G |
| 78 | T*G*T*C-G*FU*\*T\*T\*T\*T\*T\*T\*T\*T\*T\*T\*T\*T\*T\*T |
| 79 | T\*G\*FU\*C-G\*FU\*T\*T\*T\*T\*T\*T\*T\*T\*T\*T\*T\*T\*T\*T |
| 80 | T*G*U*C-G*U*T*T*T*T*T*T*T*T*T*T*T*T*T*T |
| 81 | T*G*T*C-6NB\*T\*T\*T\*T\*T\*T\*T\*T\*T\*T\*T\*T\*T\*T\*T |
| 82 | T\*G\*T\*6NB-G\*T\*T\*T\*T\*T\*T\*T\*T\*T\*T\*T\*T\*T\*T\*T |
| 83 | T\*G\*T\*6NB-G-T\*T\*T\*T\*T\*T\*T\*T\*T\*T\*T\*T\*T\*T\*T |
| 84 | JU\*G\*T\*C-G\*T\*T\*T\*T\*T\*T\*T\*T\*T\*T\*T\*T\*T\*T\*T |
| 85 | JU\*G\*JU\*C-G\*T\*T\*T\*T\*T\*T\*T\*T\*T\*T\*T\*T\*T\*T\*T |
| 86 | T\*G\*T\*C-G\*T\*JU\*T\*T\*T\*T\*T\*T\*T\*T\*T\*T\*T\*T\*T |
| 87 | T\*G FT\*C-G\*T\*T\*T\*T\*T\*T\*T\*T\*T\*T\*T\*T\*T\*T\*T |
| 88 | T\*G\*T\*C-G\*FT\*T\*T\*T\*T\*T\*T\*T\*T\*T\*T\*T\*T\*T\*T |
| 89 | T\*G FT\*C-G\*FT\*T\*T\*T\*T\*T\*T\*T\*T\*T\*T\*T\*T\*T\*T |
| 90 | T\*G\*CU\*C-G\*T\*T\*T\*T\*T\*T\*T\*T\*T\*T\*T\*T\*T\*T\*T |
| 91 | T\*G\*T\*C-G\*CU\*T\*T\*T\*T\*T\*T\*T\*T\*T\*T\*T\*T\*T\*T |
| 92 | T\*G\*CU\*C-G\*CU\*T\*T\*T\*T\*T\*T\*T\*T\*T\*T\*T\*T\*T\*T |
| 93 | T\*JU\*C-G\*T\*T\*T\*T\*T\*T\*T\*T\*T\*T\*T\*T\*T\*T\*T\*T |
| 94 | T\*G\*JU\*C-G\*T\*T\*T\*T |
| 95 | T\*G\*JU\*C-G\*T\*T\*T\*T\*G\*T\*C-G\*T\*T |
| 96 | (T\*G\*JU\*C-G\*T\*T\*L\*)2doub-3mG |
| 97 | (JU\*C\*G\*T\*T\*C\*G\*L\*)2doub-3mG |
| 98 | T\*T\*JU\*C-G\*T\*C-G\*T\*T\*T\*C-G\*T\*C-G\*T\*T |
| 99 | BU\*C-G-A-C-G-T-C-G-T-G-G-G\*G |
| 100 | T\*G\*JU\*G-C\*T\*T\*T\*T\*T\*T\*T\*T\*T\*T\*T\*T\*T\*T |
| 101 | (T\*G\*JU\*C-G\*T\*T\*L\*)2doub-teg |
| 102 | (JU\*C\*G\*T\*T\*C\*G\*L\*)2doub-teg |
| 103 | JU\*C-G\*T\*C\*G\*T\*T\*T\*T\*C\*G\*G\*C\*G\*C\*G\*C\*C\*G |
| 104 | T\*C\*G\*JU\*C-G\*T\*T\*T\*T\*C\*G\*G\*C\*G\*C\*G\*C\*C\*G |
| 105 | T\*C\*G\*T\*C\*G\*T\*T\*T\*JU\*C-G\*G\*C\*G\*C\*G\*C\*C\*G |

TABLE 8-continued

| Seq ID No# | Oligonucleotide sequence |
|---|---|
| 106 | JU\*C\*G\*T\*C\*G\*T\*T\*T\*T\*T\*C\*G\*G\*JU\*C\*G\*T\*T\*T\*T |
| 107 | T\*C\*G\*JU\*C\*G\*T\*T\*T\*T\*T\*C\*G\*G\*JU\*C\*G\*T\*T\*T\*T |
| 108 | T\*G\*JU\*C-G\*T\*T\*T\*T\*T\*T\*T\*T\*G\*JU\*C-G\*T\*T |
| 109 | T\*G\*JU\*C\*G\*T\*T\*T\*T\*T\*T\*T\*T\*T\*T\*T\*T\*T\*T |
| 110 | JU\*C-G-A-C-G-T-C-G-T-G-G\*E G\*G |
| 111 | T\*mG\*JU\*C-G\*T\*T\*T\*T\*T\*T\*T\*T\*T\*T\*T\*T\*T\*T\*T |
| 112 | T\*G\*JU\*C-mG\*T\*T\*T\*T\*T\*T\*T\*T\*T\*T\*T\*T\*T\*T\*T |
| 113 | T\*mG\*JU\*C-mG\*T\*T\*T\*T\*T\*T\*T\*T\*T\*T\*T\*T\*T\*T\*T |
| 114 | JU\*C-G\*JU\*C\*G\*T\*T\*T\*T\*C\*G\*G\*T\*C\*G\*T\*T\*T\*T |
| 115 | JU\*C\*G\*JU\*C-G\*T\*T\*T\*T\*T\*C\*G\*G\*T\*C\*G\*T\*T\*T\*T |
| 116 | T\*G\*PU\*C-G\*T\*T\*T\*T\*T\*T\*T\*T\*T\*T\*T\*T\*T\*T\*T |
| 117 | T\*G\*T\*C-G\*PU\*T\*T\*T\*T\*T\*T\*T\*T\*T\*T\*T\*T\*T\*T\*T |
| 118 | BU\*C-G-A-C-G-T-C-G-T-G-G\*G G\*G |
| 119 | T\*G\*JU\*C-G\*T\*T\*T\*T\*C\*G\*G\*C\*G\*C\*G\*C\*G\*C\*C\*G |
| 120 | T\*JU\*C-G\*T\*T\*T\*T\*C\*G\*G\*C\*G\*C\*G\*C\*G\*C\*C\*G\*T |
| 121 | T\*EU\*C-G\*T\*T\*T\*T\*T\*T\*T\*T\*T\*T\*T\*T\*T\*T\*T |
| 122 | T\*G\*EU\*G-C\*T\*T\*T\*T\*T\*T\*T\*T\*T\*T\*T\*T\*T\*T\*T |
| 123 | JU\*C-G\*T\*C\*G\*T\*T\*T\*T\*T\*C\*G\*G\*T\*C\*G\*T\*T\*T\*T |
| 124 | EU\*C-G\*T\*C\*G\*T\*T\*T\*T\*T\*C\*G\*G\*T\*C\*G\*T\*T\*T\*T |
| 125 | G\*JU\*C-G\*T\*T-hex |
| 126 | G\*JU\*C-G\*JU\*T-hex |
| 127 | G\*EU\*C-G\*EU\*T-hex |
| 128 | EU\*C\*G\*T\*C\*G\*T\*T\*T\*T\*A\*C\*G\*G\*C\*G\*C\*C\*G\*T\*G\*C\*C\*G |
| 129 | T\*C\*G\*EU\*C-G\*T\*T\*T\*T\*A\*C\*G\*G\*C\*G\*C\*C\*G\*T\*G\*C\*C\*G |
| 130 | EU\*C-G\*T\*C\*G\*A\*C\*G\*A\*T\*C\*G\*G\*C\*G\*C\*G\*C\*G\*C\*C\*G |
| 131 | JU\*C\*T\*T\*T\*T\*T\*T\*T\*T\*T\*T\*T\*T\*T\*T\*T |
| 132 | JU\*C\*T\*T\*T\*T\*T\*T\*T\*T\*C\*G\*T\*T\*T\*T\*T\*T\*T\*T\*T |
| 133 | T\*C\*T\*T\*T\*T\*T\*T\*T\*T\*JU\*C\*G\*T\*T\*T\*T\*T\*T\*T\*T\*T |
| 134 | JU\*C\*T\*T\*T\*T\*T\*T\*T\*JU\*C\*G\*T\*T\*T\*T\*T\*T\*T\*T\*T |
| 135 | JU\*C-G\*T\*C\*G\*T\*T\*T\*T\*C\*G\*T\*C\*G\*T\*T\*T\*T\*G\*T\*C\*G\*T\*T |
| 136 | T\*C\*G\*T\*C\*G\*T\*T\*T\*T\*C\*G\*T\*C\*G\*T\*T\*T\*T\*G\*JU\*C-G\*T\*T |
| 137 | JU\*C-G\*T\*C\*G\*T\*T\*T\*T\*C\*G\*T\*C\*G\*T\*T\*T\*T\*G\*JU\*C-G\*T\*T |
| 138 | T\*G\*JU\*C-E\*T\*T\*T\*T\*T\*T\*T\*T\*T\*T\*T\*T\*T\*T\*T |
| 139 | T\*G\*JU\*C-I\*T\*T\*T\*T\*T\*T\*T\*T\*T\*T\*T\*T\*T\*T\*T |
| 140 | T\*G\*JU\*Z-G\*T\*T\*T\*T\*T\*T\*T\*T\*T\*T\*T\*T\*T\*T\*T |
| 141 | T\*G\*T\*C-G\*T\*T\*JU\*T\*T\*T\*T\*T\*T\*T\*T\*T\*T\*T |
| 142 | T\*G\*T\*C-G\*T\*T\*T\*JU\*T\*T\*T\*T\*T\*T\*T\*T\*T\*T\*T |
| 143 | JU\*C-G\*T\*C\*G\*T\*T\*T\*T\*C\*G\*G\*C\*G\*C\*G\*C\*G\*C\*C\*G\*T |
| 144 | EU\*C\*G\*T\*C\*G\*T\*T\*T\*T\*C\*G\*G\*C\*G\*C\*G\*C\*G\*C\*C\*G\*T |

TABLE 8-continued

| Seq ID No # | Oligonucleotide sequence |
|---|---|
| 145 | T*C-G*EU\*C*G*T*T*T*T*C*G*G*C*G*C*G*C*C*G*T |
| 146 | T*C-G*T*C*G*T*T*T*JU\*C*G*G*C*G*C*G*C*C*G*T |
| 147 | T*C-G*T*C*G*T*T*T*EU\*C*G*G*C*G*C*G*C*C*G*T |
| 148 | EU\*C-G*T*C*G*T*T*T*EU\*C*G*G*C*G*C*G*C*C*G*T |
| 149 | EU\*C-G*EU\*C*G*T*T*T*T*C*G*G*C*G*C*G*C*C*G*T |
| 150 | JU\*C-G*EU\*C*G*T*T*T*T*C*G*G*C*G*C*G*C*C*G*T |
| 151 | JU\*C-G*T*C*G*T*T*T*T*G*T*C*G*T*T*T*G*T*C*G*T*T |
| 152 | EU\*C-G*T*C*G*T*T*T*T*G*T*C*G*T*T*T*G*T*C*G*T*T |
| 153 | T*G*BVU\*C-G*T*T*T*T*T*T*T*T*T*T*T*T*T*T*T |
| 154 | T*G*T*C-G*BVU\*T*T*T*T*T*T*T*T*T*T*T*T*T*T |
| 155 | JU\*C*G*G*C*G*G*C*C*G*C*C*G |
| 156 | JU\*C*G*T*C*G*T*T*T*T*A*C*G*G*C*G*C*C*G*T*G*C*C*3mG |
| 157 | EU\*C*G*T*C*G*T*T*T*T*A*C*G*G*C*G*C*C*G*T*G*C*C*3mG |
| 158 | EU\*C*G*EU\*C*G*T*T*T*T*A*C*G*G*C*G*C*C*G*T*G*C*C*3mG |
| 159 | EU\*C*G*EU\*C*G*T*T*T*T*A*C*G*G*C*G*C*C*G*T*G*C*C*3mG |
| 160 | EU\*C*G*T*C*G*T*T*T*T*A*C*G*G*C*G*C*C*G*T*G*C*C*G*iT |
| 161 | JU\*C*G*T*C*G*T*T*T*T*C*G*G*C*G*C*G*C*G*C*C*3mG |
| 162 | EU\*C*G*T*C*G*T*T*T*T*C*G*G*C*G*C*G*C*G*C*C*3mG |
| 163 | EU\*C-G*T*C*G*T*T*T*T*C*G*G*C*G*C*G*C*G*C*C*3mG |
| 164 | EU\*C*G*EU\*C*G*T*T*T*T*C*G*G*C*G*C*G*C*G*C*C*3mG |
| 165 | EU\*C-G*EU\*C*G*T*T*T*T*C*G*G*C*G*C*G*C*G*C*C*3mG |
| 166 | EU\*C*G*T*C*G*T*T*T*EU\*C*G*G*C*G*C*G*C*G*C*C*3mG |
| 167 | JU\*C*G*T*C*G*T*T*T*JU\*C\*G*G*C*G*C*G*C*G*C*C*3mG |
| 168 | EU\*C*G*T*C*G*T*T*T*T*C*G*G*C*G*C*G*C*G*C*C*G*IT |
| 169 | JU\*C*G*T*C*G*T*T*T*T*C*G*G*C*G*C*G*C*G*C*C*G*IT |
| 170 | EU\*C*G*T*C*G*A*C*G*T*T*C*G*G*C*G*C*C*G*T*G*C*C*3mG |
| 171 | JU\*C*G*T*C*G*A*C*G*T*T*C*G*G*C*G*C*C*G*T*G*C*C*  3mG |
| 172 | JU\*C*G*T*C*G*A*C*G*A*T*C*G*G*C*G*C*G*C*G*C*C*3mG |
| 173 | EU\*C*G*T*C*G*A*C*G*A*T*C*G*G*C*G*C*G*C*G*C*C*3mG |
| 174 | EU\*C*G*T*C*G*A*C*G*T*T*C*G*G*C*G*C*C*G*T*G*C*C*G*IT |
| 175 | EU\*C*G*T*C*G*A*C*G*A*T*C*G*G*C*G*C*G*C*G*C*C*G*IT |
| 176 | T*G*NI\*C-G*T*T*T*T*T*T*T*T*T*T*T*T*T*T*T |
| 177 | T*G*NP\*C-G*T*T*T*T*T*T*T*T*T*T*T*T*T*T*T |
| 178 | T*G*6NB\*C-G*T*T*T*T*T*T*T*T*T*T*T*T*T*T*T |
| 179 | EU\*C*G*T*C*G*T*T*T*T*T*C*G*G*T*C*G*T*T*T*T |
| 180 | JU\*C*G*T*C*G*A*C*G*A*T*G*G*C*G*C*G*C*C*G*C*C |
| 181 | EU\*C*G*T*C*G*A*C*G*A*T*G*G*C*G*C*G*C*C*G*C*C |
| 182 | T*T*C-G*T*T*T*T*C*G*G*C*G*C*G*C*G*C*C*G*T |
| 183 | T*EU\*C-G*T*T*T*T*C*G*G*C*G*C*G*C*G*C*C*G*T |

TABLE 8-continued

Seq ID No#Oligonucleotide sequence

| | |
|---|---|
| 184 | JU\*C-G\*T\*T\*T\*T\*C\*G\*G\*C\*G\*C\*G\*C\*G\*C\*C\*G\*T |
| 185 | **JU\*JU**\*C-G\*T\*T\*T\*T\*C\*G\*G\*C\*G\*C\*G\*C\*G\*C\*C\*G\*T |
| 186 | T\*JU\*C\*G\*T\*T\*T\*T\*C\*G\*G\*C\*G\*C\*G\*C\*G\*C\*C\*G\*T |
| 187 | EU\*C\*G\*T\*C\*G\*T\*T\*T\*T\*A\*C\*G\*G\*C\*G\*C\*C\*G\*T\*G\*C\*C\*G\*T |
| 188 | T\*EU\*C\*G\*T\*T\*T\*T\*A\*C\*G\*G\*C\*G\*C\*C\*G\*T\*G\*C\*C\*G\*T |
| 189 | T\*JU\*C\*G\*T\*T\*T\*T\*A\*C\*G\*G\*C\*G\*C\*C\*G\*T\*G\*C\*C\*G\*T |
| 190 | JU\*C\*G\*T\*C\*G\*T\*T\*T\*T\*rG\*rU\*rU\*rG\*rU\*rG\*rU |
| 191 | EU\*C-G\*T\*C\*G\*A\*C\*G\*A\*T\*C\*G\*G\*C\*G\*G\*C\*C\*G\*C\*C\*G\*T |
| 192 | EU\*C\*G\*T\*C\*G\*A\*C\*G\*A\*T\*C\*G\*G\*C\*G\*G\*C\*C\*G\*C\*C\*G\*T |
| 193 | EU-C-G\*A\*C\*G\*T\*C\*G\*A\*T\*C\*G\*G\*C\*G\*C\*G\*C\*G\*C\*C\*G |
| 194 | EU-C\*G\*A\*C\*G\*T\*C\*G\*A\*T\*C\*G\*G\*C\*G\*C\*G\*C\*G\*C\*C\*G |
| 195 | T\*G\*U\*C-G\*T\*T\*T\*T\*T\*T\*T\*T\*T\*T\*T\*T\*T\*T |
| 196 | T\*G\*T\*C-G\*U\*T\*T\*T\*T\*T\*T\*T\*T\*T\*T\*T\*T\*T\*T |

```
key
*phosphorothioate internucleotide linkage
-phosphodiester internucleotide linkage
teg Spacer 9 (triethylenglycol phosphate)
hex hexadecylglyceryl
3mG 3'-O-Methyl-rG
IT inverse nucleotide (3' and 5' switched)
2doub Doubler2 (Chemgenes)
FF 2,4-difluorotoluene
BU 5-bromo-2'-deoxyuridine
JU 5-Iodo-2'-deoxyuridine
U Uridine
CU 5-chloro-2'-deoxyuridine
FU 5-fluoro-dU
EU 5-ethyl-2'-deoxyuridine
6NB 6-nitro-benzimidazol
PU 5-proynyl-dU
I inosine
Z 5-methyl-dC
E 7-deaza-dG
FT a,a,a-trifluoro-dT
BVU 5-(d-bromo-vinyl)-uridine
NI nitroindol
NP nitropyrrol
F 5-fluoro-dU
L Spacer 18 (hexaethylenglycol phosphate)
```

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. An oligonucleotide comprising the sequence JU*C-G*JU*C*G*A*C*G*A*T*C*G*G*C*G*C*G*C*G*C*-C*G (SEQ ID NO: 33), wherein the JU is 5-iodo-2'-deoxyuridine, the * is phosphorothioate internucleotide linkage, and the—is phosphodiester internucleotide linkage.

2. An oligonucleotide comprising the sequence JU*C-G*T*C*G*A*C*G*A*T*C*G*G*C*G*C*G*C*G*C*-C*G (SEQ ID NO: 31), wherein the JU is 5-iodo-2'-deoxyuridine, the * is phosphorothioate internucleotide linkage, and the—is phosphodiester internucleotide linkage.

3. An oligonucleotide comprising the sequence T*C-G*JU*C*G*A*C*G*A*T*C*G*G*C*G*C*G*C*G*C*-C*G (SEQ ID NO: 32), wherein the JU is 5-iodo-2'-deoxyuridine, the * is phosphorothioate internucleotide linkage, and the—is phosphodiester internucleotide linkage.

4. An oligonucleotide comprising the sequence JU*C-G*A*C*G*T*C*G*A*T*C*G*G*C*G*C*G*C*G*C*-C*G (SEQ ID NO: 58), or the sequence JU*C*G*A*C*G*T*C*G*A*T*C*G*G*C*G*C*G*C*-G*C*C*G (SEQ ID NO: 59), wherein the JU is 5-iodo-2'-deoxyuridine, the * is phosphorothioate internucleotide linkage, and the—is phosphodiester internucleotide linkage.

5. An oligonucleotide comprising the sequence EU*C-G*A*C*G*T*C*G*A*T*C*G*G*C*G*C*G*C*G*C*-C*G (SEQ ID NO: 62), wherein the EU is 5-iodo-2'-deoxyuridine, the * is phosphorothioate internucleotide linkage, and the—is phosphodiester internucleotide linkage.

6. A pharmaceutical composition comprising the oligonucleotide of any one of claims 1 to 5, said composition further comprising an antigen.

7. A pharmaceutical composition comprising the oligonucleotide of any one of claims 1 to 5, said composition further comprising a pharmaceutically acceptable carrier.

8. A pharmaceutical composition comprising the oligonucleotide of any one of claims 1 to 5, said composition further comprising an antigen and a pharmaceutically acceptable carrier.

* * * * *